(12) United States Patent
Pericas-Brondo et al.

(10) Patent No.: US 8,362,011 B2
(45) Date of Patent: Jan. 29, 2013

(54) TRICYCLIC TRIAZOLIC COMPOUNDS

(75) Inventors: Miguel Angel Pericas-Brondo, Barcelona (ES); Antoni Torrens-Jover, Barcelona (ES); Félix Cuevas-Cordobes, Barcelona (ES); Susana Yenes-Minguez, Barcelona (ES)

(73) Assignee: Laboratories del Dr. Esteve, S.A., Barcelona (ES)

( * ) Notice: Subject to any disclaimer, the term of this patent is extended or adjusted under 35 U.S.C. 154(b) by 224 days.

(21) Appl. No.: 12/746,635

(22) PCT Filed: Dec. 5, 2008

(86) PCT No.: PCT/EP2008/066876
§ 371 (c)(1),
(2), (4) Date: Jul. 16, 2010

(87) PCT Pub. No.: WO2009/071657
PCT Pub. Date: Jun. 11, 2009

(65) Prior Publication Data
US 2010/0298309 A1    Nov. 25, 2010

(30) Foreign Application Priority Data

Dec. 7, 2007   (EP) .................................... 07380343

(51) Int. Cl.
*C07D 498/14*  (2006.01)
*A61K 31/5383*  (2006.01)
(52) U.S. Cl. ..................................... 514/230.2; 544/101
(58) Field of Classification Search .................. 544/101; 514/230.2
See application file for complete search history.

(56) References Cited

FOREIGN PATENT DOCUMENTS

| EP | 1 849 772 A1 | 10/2007 |
|---|---|---|
| WO | WO 2006/021463 | 3/2006 |
| WO | WO 2006/024517 | 3/2006 |

OTHER PUBLICATIONS

Walker, J.M. et al., *Pharmacological Reviews*, 1990, 42, 355.
Snyder, S.H., *J. Neuropsychiatry* 1989, 1, 7.
G .Ronsisvalle et al., *Pure Appl. Chem.* 73,1499-1509; 2001.
Kaiser et al. (1991) *Neurotransmissions* 7 (1): 1-5.
Bowen W.D. (2000) *Pharmaceutica Acta Helvetiae* 74: 211-218.
Quirion, R. et al. *Trends Pharmacol. Sci.*, 1992, 13: 85-86.
Hanner, M. et al. *Proc. Natl. Acad. Sci.*, 1996, 93: 8072-8077.
*J. Am. Chem. Soc.*; 2006, 128, 6376-6390.
*J. Org. Chem.* 1997, 62, 4197-4199.
IASP, *Classification of chronic pain*, 2nd Edition, IASP Press (2002), 210.
DeHaven-Hudkins, D.L., 1992, *Eur. J. Pharmacol.* 227, 371-378.

*Primary Examiner* — Kahsay T Habte
(74) *Attorney, Agent, or Firm* — Ostrolenk Faber LLP

(57) ABSTRACT

The present invention relates to new tricyclic triazolic compounds having a high affinity for sigma-1 receptor as well as to the process for the preparation thereof, to composition comprising them and to their use as medicaments according to compounds of formula (I), Wherein $R_1$ and $R_2$ are as defined in the description.

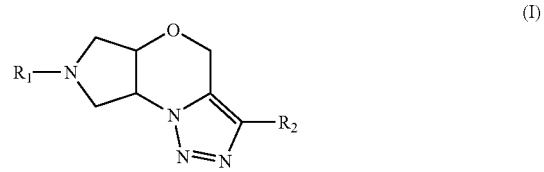

(I)

21 Claims, No Drawings

TRICYCLIC TRIAZOLIC COMPOUNDS

CROSS-REFERENCE TO RELATED APPLICATIONS

The present application is a 35 U.S.C. §§371 national phase conversion of PCT/EP2008/066876, filed Dec. 5, 2008, which claims priority of European Patent Application No. 07380343.9, filed Dec. 7, 2007, the disclosure of which is incorporated herein by reference. The PCT International Application was published in the English language.

FIELD OF THE INVENTION

The present invention relates to new tricyclic triazolic compounds having a great affinity for sigma receptors, especially sigma-1 receptors, as well as to the process for the preparation thereof, to compositions comprising them, and to their use as medicaments.

BACKGROUND OF THE INVENTION

The search for new therapeutic agents has been greatly aided in recent years by better understanding of the structure of proteins and other biomolecules associated with target diseases. One important class of these proteins are the sigma (σ) receptors, cell surface receptors of the central nervous system (CNS) which may be related to the dysphoric, hallucinogenic and cardiac stimulant effects of opioids. From studies of the biology and function of sigma receptors, evidence has been presented that sigma receptor ligands may be useful in the treatment of psychosis and movement disorders such as dystonia and tardive dyskinesia, and motor disturbances associated with Huntington's chorea or Tourette's syndrome and in Parkinson's disease (Walker, J. M. et al, Pharmacological Reviews, 1990, 42, 355). It has been reported that the known sigma receptor ligand rimcazole clinically shows effects in the treatment of psychosis (Snyder, S. H., Largent, B. L. J. Neuropsychiatry 1989, 1, 7). The sigma binding sites have preferential affinity for the dextrorotatory isomers of certain opiate benzomorphans, such as (+)SKF 10047, (+)cyclazocine, and (+)pentazocine and also for some narcoleptics such as haloperidol.

"The sigma receptor's" as used in this application is/are well known and defined using the following citation: This binding site represents a typical protein different from opioid, NMDA, dopaminergic, and other known neurotransmitter or hormone receptor families (G. Ronsisvalle et al. Pure Appl. Chem. 73, 1499-1509 (2001)).

The sigma receptor has at least two subtypes, which may be discriminated by stereoselective isomers of these pharmacoactive drugs. SKF 10047 has nanomolar affinity for the sigma 1 (σ-1) site, and has micromolar affinity for the sigma 2 (σ-2) site. Haloperidol has similar affinities for both subtypes.

The Sigma-1 receptor is a non-opiaceous type receptor expressed in numerous adult mammal tissues (e.g. central nervous system, ovary, testicle, placenta, adrenal gland, spleen, liver, kidney, gastrointestinal tract) as well as in embryo development from its earliest stages, and is apparently involved in a large number of physiological functions. Its high affinity for various pharmaceuticals has been described, such as for SKF-10047, (+)-pentazocine, haloperidol and rimcazole, among others, known ligands with analgesic, anxiolytic, antidepressive, antiamnesic, antipsychotic and neuroprotective activity. Sigma-1 receptor is of great interest in pharmacology in view of its possible physiological role in processes related to analgesia, anxiety, addiction, amnesia, depression, schizophrenia, stress, neuroprotection and psychosis [Kaiser et al (1991) Neurotransmissions 7 (1): 1-5], [Walker, J. M. et al, Pharmacological Reviews, 1990, 42, 355] and [Bowen W. D. (2000) Pharmaceutica Acta Helvetiae 74: 211-218].

The Sigma-2 receptor is also expressed in numerous adult mammal tissues (e.g. nervous system, immune system, endocrine system, liver, kidney). Sigma-2 receptors can be components in a new apoptosis route that may play an important role in regulating cell proliferation or in cell development. This route seems to consist of Sigma-2 receptors joined to intracellular membranes, located in organelles storing calcium, such as the endoplasmic reticulum and mitochondria, which also have the ability to release calcium from these organelles. The calcium signals can be used in the signaling route for normal cells and/or in induction of apoptosis.

Agonists of Sigma-2 receptors induce changes in cell morphology, apoptosis in several types of cell lines and regulate the expression of p-glycoprotein mRNA, so that they are potentially useful as antineoplasic agents for treatment of cancer. In fact, Sigma-2 receptor agonists have been observed to induce apoptosis in mammary tumour cell lines resistant to common antineoplasic agents that damage DNA. In addition, agonists of Sigma-2 receptors enhance the cytotoxic effects of these antineoplasic agents at concentrations in which the agonist is not cytotoxic. Thus, agonists of Sigma-2 receptors can be used as antineoplasic agents at doses inducing apoptosis or at sub-toxic doses in combination with other antineoplasic agents to revert the resistance to the drug, thereby allowing using lower doses of the antineoplasic agent and considerably reducing its adverse effects.

Antagonists of Sigma-2 receptors can prevent the irreversible motor side effects caused by typical neuroleptic agents. In fact, it has been found that antagonists of Sigma-2 receptors can be useful as agents for improving the weakening effects of delayed dyskinesia appearing in patients due to chronic treatment of psychosis with typical antipsychotic drugs, such as haloperidol. Sigma-2 receptors also seem to play a role in certain degenerative disorders in which blocking these receptors could be useful.

Endogenous sigma ligands are not known, although progesterone has been suggested to be one of them. Possible sigma-site-mediated drug effects include modulation of glutamate receptor function, neurotransmitter response, neuroprotection, behavior, and cognition (Quirion, R. et al. Trends Pharmacol. Sci., 1992, 13:85-86). Most studies have implied that sigma binding sites (receptors) are plasmalemmal elements of the signal transduction cascade. Drugs reported to be selective sigma ligands have been evaluated as antipsychotics (Hanner, M. et al. Proc. Natl. Acad. Sci., 1996, 93:8072-8077). The existence of sigma receptors in the CNS, immune and endocrine systems have suggested a likelihood that it may serve as link between the three systems.

In view of the potential therapeutic applications of agonists or antagonists of the sigma receptor, a great effort has been directed to find selective ligands. Thus, the prior art discloses different sigma receptor ligands.

For instance, the international patent application WO2007/098961 describes 4,5,6,7 tetrahydrobenzo[b]thiophene derivatives having pharmacological activity towards the sigma receptor.

Spiro[benzopyran] or spiro[benzofuran] derivatives were also disclosed in EP1847542 as well as pyrazole derivatives (EP1634873) with pharmacological activity on sigma receptors.

Nevertheless, there is still a need to find compounds having pharmacological activity towards the sigma receptor, being both effective and selective, and having good "drugability"

properties, i.e. good pharmaceutical properties related to administration, distribution, metabolism and excretion.

SUMMARY OF THE INVENTION

The present invention discloses novel compounds with great affinity to sigma receptors which might be used for the treatment of sigma related disorders or diseases.

Specifically, it is an object of the present invention novel tricyclic triazolic compounds of general formula (I):

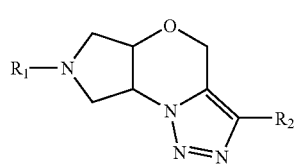

(I)

It is also an object of the invention different processes for their preparation, including a process for preparing enantiomerically pure compounds of formula (I).

Another object of the invention refers to the use of such compounds of general formula I for the manufacture of a medicament for the treatment or prophylaxis of sigma receptor mediated diseases or conditions, especially sigma-1 mediated diseases or conditions. Within the group of diseases or conditions mediated by sigma receptor for which the compounds of the invention are effective diarrhea, lipoprotein disorders, hyperlipidemia, hypertriglyceridemia, hypercholesterolemia, obesity, migraine, arthritis, hypertension, arrhythmia, ulcer, glaucoma, learning, memory and attention deficits, cognition disorders, neurodegenerative diseases, demyelinating diseases, addiction to drugs and chemical substances including cocaine, amphetamine, ethanol and nicotine; tardive dyskinesia, ischemic stroke, epilepsy, stroke, stress, cancer, psychotic conditions, in particular depression, anxiety or schizophrenia; inflammation or autoimmune diseases, may be cited. Compounds of the invention are very good anxiolytic and immunosuppressant and are especially useful in the treatment and prophylaxis t is also an object of the invention pharmaceutical compositions comprising one or more compounds of general formula (I) with at least one pharmaceutically acceptable excipient. The pharmaceutical compositions in accordance with the invention can be adapted in order to be administered by any route of administration, be it orally or parenterally, such as pulmonarily, nasally, rectally and/or intravenously. Therefore, the formulation in accordance with the invention may be adapted for topical or systemic application, particularly for dermal, subcutaneous, intramuscular, intra-articular, intraperitoneal, pulmonary, buccal, sublingual, nasal, percutaneous, vaginal, oral or parenteral application.

DETAILED DESCRIPTION OF THE INVENTION

The invention first relates to compounds of general formula (I)

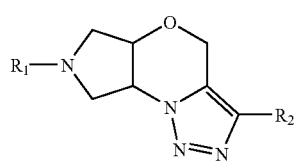

(I)

wherein
$R_1$ represents an hydrogen atom; —$COR_3$, —$C(O)OR_3$, —$C(O)NR_3R_4$, —$C=NR_3$, —CN, —$OR_3$, —$OC(O)R_3$, —$S(O)_n$—$R_3$, —$NR_3R_4$, —$NR_3C(O)R_4$, —$NO_2$, —$N=CR_3R_4$, or an halogen atom;
a branched or unbranched, saturated or unsaturated, optionally at least mono-substituted, aliphatic radical $C_{1-10}$;
a substituted or unsubstituted cycloalkyl radical $C_{3-9}$; a branched or unbranched cycloalkyl-alkyl radical $C_{1-10}$ group in which either the alkyl group and/or the cycloalkyl group is optionally at least mono-substituted; a substituted or unsubstituted cycloalkyl $C_{3-9}$ or cycloalkylalkyl $C_{1-10}$ group in which the cycloalkyl group is condensed with another substituted or unsubstituted, mono- or polycyclic ring system;
a substituted or unsubstituted aryl radical; a substituted or unsubstituted, branched or unbranched arylalkyl radical $C_{1-10}$, optionally at least mono-substituted benzhydryl group;
a substituted or unsubstituted heteroaryl radical; a substituted or unsubstituted, branched or unbranched heteroarylalkyl radical $C_{1-10}$; a substituted or unsubstituted non-aromatic heterocyclyl radical $C_{3-9}$; a substituted or unsubstituted, branched or unbranched heterocyclylalkyl radical $C_{3-9}$;
a substituted or unsubstituted heterocyclyl $C_{3-9}$ or heterocycloalkyl radical $C_{1-10}$ group in which the heterocyclyl group is condensed with another substituted or unsubstituted mono- or polycyclic ring system;
$R_2$ represents an hydrogen atom; —$COR_3$, —$C(O)OR_3$, —$C(O)NR_3R_4$, —$C=NR_3$, —CN, —$OR_3$, —$OC(O)R_3$, —$S(O)_n$—$R_3$, —$NR_3R_4$, —$NR_3C(O)R_4$, —$NO_2$, —$N=CR_3R_4$, or an halogen atom;
a branched or unbranched, saturated or unsaturated, optionally at least mono-substituted, aliphatic radical $C_{1-10}$;
a substituted or unsubstituted cycloalkyl radical $C_{3-9}$; a branched or unbranched cycloalkyl-alkyl radical $C_{1-10}$ group in which either the alkyl group and/or the cycloalkyl group is optionally at least mono-substituted; a substituted or unsubstituted cycloalkyl $C_{3-9}$ or cycloalkylalkyl $C_{1-10}$ radical group in which the cycloalkyl group is condensed with another substituted or unsubstituted mono- or polycyclic ring system;
a substituted or unsubstituted aryl radical; a substituted or unsubstituted, branched or unbranched arylalkyl radical $C_{1-10}$, optionally at least mono-substituted benzhydryl group;
a substituted or unsubstituted heteroaryl radical; a substituted or unsubstituted, branched or unbranched heteroarylalkyl radical $C_{1-10}$; a substituted or unsubstituted non-aromatic heterocyclyl radical $C_{3-9}$; a substituted or unsubstituted, branched or unbranched heterocyclylalkyl radical $C_{3-9}$;
a substituted or unsubstituted heterocyclyl $C_{3-9}$ or heterocycloalkyl $C_{1-10}$ radical group in which the heterocyclyl group is condensed with another substituted or unsubstituted mono- or polycyclic ring system;
$R_3$ and $R_4$ are each independently selected from hydrogen or halogen;
a branched or unbranched, saturated or unsaturated, optionally at least mono-substituted, aliphatic radical $C_{1-10}$;
a substituted or unsubstituted cycloalkyl radical $C_{3-9}$; branched or unbranched cycloalkyl-alkyl radical $C_{1-10}$ group in which either the alkyl group and/or the cycloalkyl group is optionally at least mono-substituted;
a substituted or unsubstituted aryl radical; a substituted or unsubstituted arylalkyl radical $C_{1-10}$, optionally at least mono-substituted benzhydryl group;

a substituted or unsubstituted heteroaryl radical; a substituted or unsubstituted, branched or unbranched heteroarylalkyl radical $C_{1-10}$; a substituted or unsubstituted non-aromatic heterocyclyl radical $C_{3-9}$; a substituted or unsubstituted, branched or unbranched heterocyclylalkyl radical $C_{3-9}$;

a substituted or unsubstituted heterocyclyl $C_{3-9}$ or heterocycloalkyl $C_{1-10}$ radical group in which the heterocyclyl group is condensed with another substituted or unsubstituted mono- or polycyclic ring system;

n is 0, 1 or 2;

or a pharmaceutically acceptable salt, isomer, prodrug or solvate thereof.

Aliphatic radicals $C_{1-10}$, as referred to in the present invention, are optionally mono- or polysubstituted and may be branched or unbranched, saturated or unsaturated. Unsaturated aliphatic groups, as defined in the present invention, include alkyl, alkenyl and alkinyl radicals. Preferred aliphatic radicals according to the present invention include, but are not limited to, methyl, ethyl, vinyl (ethenyl), ethinyl, propyl, n-propyl, isopropyl, allyl (2-propenyl), 1-propinyl, methylethyl, butyl, n-butyl, iso-butyl, sec-butyl, tert-butyl butenyl, butinyl, 1-methylpropyl, 2-methylpropyl, 1,1-dimethylethyl, pentyl, n-pentyl, 1,1-dimethylpropyl, 1,2-dimethylpropyl, 2,2-dimethylpropyl, hexyl, 1-methylpentyl, n-heptyl, n-octyl, n-nonyl, and n-decyl. Preferred substituents for aliphatic radicals, according to the present invention, are a $C_{1-4}$ alkyl group, a linear or branched $C_{1-6}$ alkoxy group, F, Cl, I, Br, CF3, CH2F, CHF2, CN, OH, SH, NH2, oxo, (C=O)R', SR', SOR', SO2R', NHR', NR'R" whereby R' and optionally R" for each substituent independently represents a linear or branched $C_{1-6}$-alkyl group.

Alkyl radicals, as referred to in the present invention, are saturated aliphatic radicals. They may be linear or branched and are optionally substituted.

Cycloalkyl radical $C_{3-9}$, as referred to in the present invention, are understood as meaning saturated and unsaturated (but not aromatic), cyclic hydrocarbons, which can optionally be unsubstituted, mono- or polysubstituted. In these radicals, for example C3-4-cycloalkyl represents C3- or C4-cycloalkyl, C3-5-cycloalkyl represents C3-, C4- or C5-cycloalkyl, and so for. With respect to cycloalkyl, the term also includes saturated cycloalkyls in which optionally at least one carbon atom may be replaced by a heteroatom, preferably S, N, P or O. However, mono- or polyunsaturated, preferably monounsaturated, cycloalkyls without a heteroatom in the ring also in particular fall under the term cycloalkyl as long as the cycloalkyl is not an aromatic system.

Examples for cycloalkyl radical preferably include, but are not limited to, cyclopropyl, 2-methylcyclopropyl, cyclopropylmethyl, cyclobutyl, cyclopentyl, cyclopentylmethyl, cyclohexyl, cycloheptyl, cyclooctyl, acetyl, tert-butyl, adamantyl, pyrroline, pyrrolidine, pyrrolidineone, pyrazoline, pyrazolinone, oxopyrazolinone, aziridine, acetidine, tetrahydropyrrole, oxirane, oxetane, dioxetane, tetrahydrofurane, dioxane, dioxolane, oxathiolane, oxazolidine, thiirane, thietane, thiolane, thiane, thiazolidine, piperidine, piperazine or morpholine.

Cycloalkyl radicals $C_{3-9}$, as defined in the present invention, are optionally mono- or polysubstituted by substituents independently selected from a $C_{1-4}$ alkyl group, a linear or branched $C_{1-6}$ alkoxy group, F, Cl, I, Br, CF3, CH2F, CHF2, ON, OH, SH, NH2, oxo, (C=O)R', SR', SOR', SO2R', NHR', NR'R" whereby R' and optionally R" for each substituent independently represents a linear or branched C1-6-alkyl group.

An aryl radical, as referred to in the present invention, is understood as meaning ring systems with at least one aromatic ring but without heteroatoms in any of the rings. These aryl radicals may be optionally mono- or polysubstituted by substituents independently selected from a C1-4 alkyl group, a linear or branched C1-6 alkoxy group, an optionally at least mono-substituted phenyl group, F, Cl, I, Br, CF3, CH2F, CHF2, ON, OH, SH, NH2, oxo, (O=O)R', SR', SOR', SO2R', N(C=O) OR', NHR', NR'R" whereby R' and optionally R" for each substituent independently represents a linear or branched C1-6-alkyl group. Preferred examples of aryl radicals include, but are not limited to, phenyl, naphthyl, fluoranthenyl, fluorenyl, tetralinyl or indanyl or anthracenyl radicals, which may be optionally mono- or polysubstituted, if not defined otherwise.

An arylalkyl radical $C_{1-10}$, as defined in the present invention, comprises a linear or branched, optionally at least mono-substituted alkyl chain which is bonded to an aryl group, as defined above. A preferred alkyl-aryl radical is a benzyl group, wherein the alkyl chain is optionally branched or substituted. Preferred substituents for alkyl-aryl radicals, according to the present invention, are F, Cl, Br, I, NH2, SH, OH, SO2, CF3, carboxy, amido, cyano, carbamyl, nitro, phenyl, benzyl, —SO2NH2, C1-6 alkyl and/or C1 6-alkoxy.

A heteroaryl radical $C_{1-10}$, is understood as meaning heterocyclic ring systems which have at least one aromatic ring and may optionally contain one or more heteroatoms from the group consisting of nitrogen, oxygen and/or sulfur and may optionally be mono- or polysubstituted by substituents independently selected from a C1-4 alkyl group, a linear or branched C1-6 alkoxy group, F, Cl, I, Br, CF3, CH2F, CHF2, ON, OH, SH, NH2, oxo, (C=O)R', SR', SOR', SO2R', NHR', NR'R" whereby R' and optionally R" for each substituent independently represents a linear or branched C1-6-alkyl group. Preferred examples of heteroaryls include, but are not limited to, furan, benzofuran, thiophene, benzothiophene, pyrrole, pyridine, pyrimidine, pyridazine, pyrazine, quinoline, isoquinoline, phthalazine, benzo-1,2,5-thiadiazole, benzothiazole, indole, benzotriazole, benzodioxolane, benzodioxane, benzimidazole, carbazole and quinazoline.

The term "condensed" according to the present invention means that a ring or ring-system is attached to another ring or ring-system, whereby the terms "annulated" or "annelated" are also used by those skilled in the art to designate this kind of attachment.

The term "ring system" according to the present invention refers to ring systems comprises saturated, unsaturated or aromatic carbocyclic ring systems which contain optionally at least one heteroatom as ring member and which are optionally at least mono-substituted. Said ring systems may be condensed to other carbocyclic ring systems such as aryl groups, naphtyl groups, heteroaryl groups, cycloalkyl groups, etc.

Cyclyl groups/radicals $C_{1-10}$, as defined in the present invention, comprise any saturated, unsaturated or aromatic carbocyclic ring systems which contain optionally at least one heteroatom as ring member and which are optionally at least mono-substituted. Cyclyl groups preferably comprise aryl, heteroaryl, cyclyl, heterocyclyl and/or spiro ring systems.

Heterocyclyl groups/radicals $C_{1-10}$, as defined in the present invention, comprise any saturated, unsaturated or aromatic carbocyclic ring systems which are optionally at least mono-substituted and which contain at least one heteroatom as ring member. Preferred heteroatoms for these heterocyclyl groups are N, S or O.

The term "salt" must be understood as any form of an active compound used in accordance with this invention in which the said compound is in ionic form or is charged and coupled to a counter-ion (a cation or anion) or is in solution. This definition also includes quaternary ammonium salts and complexes of the active molecule with other molecules and ions, particularly complexes formed via ionic interactions. The definition particularly includes physiologically acceptable salts; this term must be understood as equivalent to "pharmacologically acceptable salts".

The term "pharmaceutically acceptable salts" in the context of this invention means any salt that is tolerated physiologically (normally meaning that it is not toxic, particularly as a result of the counter-ion) when used in an appropriate manner for a treatment, particularly applied or used in humans and/or mammals These physiologically acceptable salts may be formed with cations or bases and, in the context of this invention, are understood to be salts formed by at least one compound used in accordance with the invention—normally an acid (deprotonated)—such as an anion and at least one physiologically tolerated cation, preferably inorganic, particularly when used on humans and/or mammals. Salts with alkali and alkali earth metals are particularly preferred, as well as those formed with ammonium cations ($NH_4^+$). Preferred salts are those formed with (mono) or (di)sodium, (mono) or (di)potassium, magnesium or calcium. These physiologically acceptable salts may also be formed with anions or acids and, in the context of this invention, are understood as being salts formed by at least one compound used in accordance with the invention—normally protonated, for example in nitrogen—such as a cation and at least one physiologically tolerated anion, particularly when used on humans and/or mammals. This definition specifically includes in the context of this invention a salt formed by a physiologically tolerated acid, i.e. salts of a specific active compound with physiologically tolerated organic or inorganic acids—particularly when used on humans and/or mammals. Examples of this type of salts are those formed with: hydrochloric acid, hydrobromic acid, sulphuric acid, methanesulfonic acid, formic acid, acetic acid, oxalic acid, succinic acid, malic acid, tartaric acid, mandelic acid, fumaric acid, lactic acid or citric acid.

The term "solvate" in accordance with this invention should be understood as meaning any form of the active compound in accordance with the invention in which said compound is bonded by a non-covalent bond to another molecule (normally a polar solvent), especially including hydrates and alcoholates, for example methanolate.

In a particular and preferred embodiment of the invention $R_1$ is an hydrogen atom; —$COR_3$, —$C(O)OR_3$, —$C(O)NR_3R_4$, —$C=NR_3$, —CN, —$OR_3$, —$OC(O)R_3$, —$S(O)_n$—$R_3$, —$NR_3R_4$, —$NR_3C(O)R_4$, —$N=CR_3R_4$, or an halogen atom;
a branched or unbranched, saturated or unsaturated, optionally at least mono-substituted, aliphatic radical $C_{1-10}$; a substituted or unsubstituted cycloalkyl radical $C_{3-9}$; a substituted or unsubstituted aryl radical; a substituted or unsubstituted, branched or unbranched arylalkyl radical $C_{1-10}$, at least mono-substituted benzhydryl group;
a substituted or unsubstituted heteroaryl radical; a substituted or unsubstituted branched or unbranched, heteroarylalkyl radical $C_{1-10}$; a substituted or unsubstituted non-aromatic heterocyclyl radical $C_{3-9}$; a substituted or unsubstituted, branched or unbranched heterocyclylalkyl radical $C_{3-9}$; or a pharmaceutically acceptable salt, isomer, prodrug or solvate thereof.

In another preferred embodiment of the invention $R_2$ is an hydrogen atom or —$COR_3$, —$C(O)OR_3$, —$C(O)NR_3R_4$, —$C=NR_3$, —CN, —$OR_3$, —$OC(O)R_3$, —$S(O)_n$—$R_3$, —$NR_3R_4$, —$NR_3C(O)R_4$, —$NO_2$, —$N=CR_3R_4$, an halogen atom; a substituted or unsubstituted cycloalkyl radical $C_{3-9}$; a substituted or unsubstituted aryl radical; a substituted or unsubstituted arylalkyl radical $C_{1-10}$; a substituted or unsubstituted heteroaryl radical; an unbranched or branched, saturated or unsaturated, optionally at least mono-substituted, aliphatic radical $C_{1-10}$; an unsubstituted arylalkyl or heteroarylalkyl radical $C_{1-10}$ or a pharmaceutically acceptable salt, isomer, prodrug or solvate thereof.

In another preferred embodiment of the invention $R_3$ and $R_4$ are each independently selected from hydrogen or halogen; a substituted or unsubstituted cycloalkyl radical $C_{3-9}$; a substituted or unsubstituted aryl radical; a substituted or unsubstituted arylalkyl radical $C_{1-10}$; a substituted or unsubstituted heteroaryl radical; an unbranched or branched, saturated or unsaturated, optionally at least mono-substituted, aliphatic radical $C_{1-10}$; an unsubstituted arylalkyl or heteroarylalkyl radical $C_{1-10}$ or a pharmaceutically acceptable salt, isomer, prodrug or solvate thereof.

In another preferred embodiment of the invention $R_1$ is an hydrogen atom; an halogen atom; —$COR_3$; —$C(O)OR_3$; —$C(O)NR_3R_4$; —$S(O)_n$—$R_3$; a substituted or unsubstituted cycloalkyl radical $C_{3-9}$; a substituted or unsubstituted aryl radical; a substituted or unsubstituted arylalkyl radical $C_{1-10}$; a substituted or unsubstituted heteroaryl radical; an unbranched or branched, saturated or unsaturated, optionally at least mono-substituted, aliphatic radical $C_{1-10}$;
$R_2$ hydrogen atom or halogen; a substituted or unsubstituted cycloalkyl radical $C_{3-9}$; a substituted or unsubstituted aryl radical; a substituted or unsubstituted heteroaryl radical; an unbranched or branched, saturated or unsaturated, optionally at least mono-substituted, aliphatic radical $C_{1-10}$;
and
$R_3$ and $R_4$ are each independently selected from hydrogen or halogen; a substituted or unsubstituted aryl radical; a substituted or unsubstituted heteroaryl radical; an unbranched or branched, saturated or unsaturated, optionally at least mono-substituted aliphatic, radical $C_{1-10}$ or a substituted; an unsubstituted alkylaryl or heteroarylalkyl radical $C_{1-10}$ or a pharmaceutically acceptable salt, isomer, prodrug or solvate thereof.

In another preferred embodiment of the invention $R_1$ is an hydrogen atom; an halogen atom; —$COR_3$; —$C(O)OR_3$; —$C(O)NR_3R_4$; —$S(O)_n$—$R_3$; a substituted or unsubstituted cycloalkyl radical $C_{3-9}$; a substituted or unsubstituted aryl radical; a substituted or unsubstituted arylalkyl radical $C_{1-10}$; a substituted or unsubstituted heteroaryl radical; an unbranched or branched, saturated or unsaturated, optionally at least mono-substituted, aliphatic radical $C_{1-10}$;
$R_2$ is hydrogen atom or halogen; a substituted or unsubstituted aryl radical; an unbranched or branched, saturated or unsaturated, optionally at least mono-substituted, aliphatic radical $C_{1-10}$; and
$R_3$ and $R_4$ are each independently selected from hydrogen or halogen; an unbranched or branched, saturated or unsaturated, optionally at least mono-substituted aliphatic radical $C_{1-10}$; an unsubstituted alkylaryl or heteroarylalkyl radical $C_{1-10}$ or a pharmaceutically acceptable salt, isomer, prodrug or solvate thereof.

The compounds of the present invention represented by the above described formula (I) may include enantiomers depending on the presence of chiral centers or isomers depending on the presence of double bonds (e.g. Z, E). The single isomers, enantiomers or diastereoisomers and mixtures thereof fall within the scope of the present invention.

Optionally in form of one of the stereoisomers, preferably enantiomers are those with the "5a,8a-trans" stereoselective for formula (I).

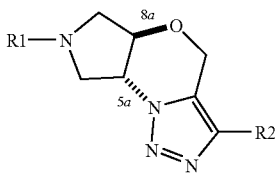

(I)

The obtained reaction products may, if desired, be purified by conventional methods, such as crystallization and chromatography. Where the above described processes for the preparation of compounds of the invention give rise to mixtures of stereoisomers, these isomers may be separated by conventional techniques such as preparative chromatography. If there are chiral centers the compounds may be prepared in racemic form, or individual enantiomers may be prepared either by enantiospecific synthesis or by resolution.

One preferred pharmaceutically acceptable form is the crystalline form, including such form in pharmaceutical composition. In the case of salts and solvates the additional ionic and solvent moieties must also be non-toxic. The compounds of the invention may present different polymorphic forms, it is intended that the invention encompasses all such forms.

Among all the compounds described in the general formula (I), particularly preferred are any of those compounds selected from:

[1] (5a,8a-trans)-7-(4-methoxybenzyl)-4,5a,6,7,8,8a-hexahydropyrrolo[3,4-b][1,2,3]triazolo[1,5-d][1,4]oxazine,
[2] (5a,8a-trans)-7-(4-methoxybenzyl)-3-methyl-4,5a,6,7,8,8a-hexahydropyrrolo[3,4-b][1,2,3]triazolo[1,5-d][1,4]oxazine,
[3] (5a,8a-trans)-3-ethyl-7-(4-methoxybenzyl)-4,5a,6,7,8,8a-hexahydro pyrrolo[3,4-b][1,2,3]triazolo[1,5-d][1,4]oxazine,
[4] (5a,8a-trans)-7-benzyl-4,5a,6,7,8,8a-hexahydropyrrolo[3,4-b][1,2,3]triazolo[1,5-d][1,4]oxazine,
[5] (5a,8a-trans)-7-benzyl-3-methyl-4,5a,6,7,8,8a-hexahydropyrrolo[3,4-b][1,2,3]triazolo[1,5-d][1,4]oxazine,
[6] (5a,8a-trans)-7-benzyl-3-(4-(trifluoromethyl)phenyl)-4,5a,6,7,8,8a-hexa hydropyrrolo[3,4-b][1,2,3]triazolo[1,5-d][1,4]oxazine,
[7] (5a,8a-trans)-7-benzyl-3-(2-fluorophenyl)-4,5a,6,7,8,8a-hexahydro pyrrolo[3,4-b][1,2,3]triazolo[1,5-d][1,4]oxazine,
[8] (5a,8a-trans)-7-benzyl-3-ethyl-4,5a,6,7,8,8a-hexahydropyrrolo[3,4-b][1,2,3]triazolo[1,5-d][1,4]oxazine,
[9] (5a,8a-trans)-7-benzyl-3-(4-chlorophenyl)-4,5a,6,7,8,8a-hexahydropyrrolo[3,4-b][1,2,3]triazolo[1,5-d][1,4]oxazine,
[10] (5a,8a-trans)-7-benzyl-3-(3-fluorophenyl)-4,5a,6,7,8,8a-hexahydropyrrol[3,4-b][1,2,3]triazolo[1,5-d][1,4]oxazine,
[11] (5a,8a-trans)-7-benzyl-3-phenyl-4,5a,6,7,8,8a-hexahydropyrrolo[3,4-b][1,2,3]triazolo[1,5-d][1,4]oxazine,
[12] (5a,8a-trans)-4,5a,6,7,8,8a-hexahydropyrrolo[3,4-b][1,2,3]triazolo[1,5-d][1,4]oxazine,
[13] (5a,8a-trans)-3-phenyl-4,5a,6,7,8,8a-hexahydropyrrolo[3,4-b][1,2,3] triazolo[1,5-d][1,4]oxazine,
[14] (5a,8a-trans)-7-(methylsulfonyl)-4,5a,6,7,8,8a-hexahydropyrrolo[3,4-b][1,2,3]triazolo[1,5-d][1,4]oxazine,
[15] (5a,8a-trans)-7-(4-bromophenylsulfonyl)-4,5a,6,7,8,8a-hexahydro pyrrolo[3,4-b][1,2,3]triazolo[1,5-d][1,4]oxazine,
[16] (5a,8a-trans)-7-(phenylsulfonyl)-4,5a,6,7,8,8a-hexahydropyrrolo[3,4-b][1,2,3]triazolo[1,5-d][1,4]oxazine,
[17] (5a,8a-trans)-7-(2-fluorophenylsulfonyl)-4,5a,6,7,8,8a-hexahydropyrrolo[3,4-b][1,2,3]triazolo[1,5-d][1,4]oxazine,
[18] (5a,8a-trans)-7-(4-fluorophenylsulfonyl)-4,5a,6,7,8,8a-hexahydropyrrolo[3,4-b][1,2,3]triazolo[1,5-d][1,4]oxazine,
[19] (5a,8a)-7-(methylsulfonyl)-3-phenyl-4,5a,6,7,8,8a-hexahydropyrrolo[3,4-b][1,2,3]triazolo[1,5-d][1,4]oxazine,
[20] (5a,8a-trans)-7-(4-fluorophenylsulfonyl)-3-phenyl-4,5a,6,7,8,8a-hexa hydropyrrolo[3,4-b][1,2,3]triazolo[1,5-d][1,4]oxazine,
[21] (2-fluorophenyl)((5a,8a-trans)-5a,6,8,8a-tetrahydropyrrolo[3,4-b][1,2,3] triazolo[1,5-d][1,4]oxazin-7(4H)-yl)methanone,
[22] phenyl((5a,8a-trans)-5a,6,8,8a-tetrahydropyrrolo[3,4-b][1,2,3]triazolo[1,5-d][1,4]oxazin-7(4H)-yl)methanone,
[23] (2,4-dichlorophenyl)((5a,8a-trans)-5a,6,8,8a-tetrahydropyrrolo[3,4-b][1,2,3] triazolo[1,5-d][1,4]oxazin-7(4H)-yl)methanone,
[24] 3-phenyl-1-((5a,8a-trans)-5a,6,8,8a-tetrahydropyrrolo[3,4-b][1,2,3] triazolo[1,5-d][1,4]oxazin-7(4H)-yl)propan-1-one,
[25] 1-((5a,8a-trans)-5a,6,8,8a-tetrahydropyrrolo[3,4-b][1,2,3]triazolo[1,5-d][1,4]oxazin-7(4H)-yl)butan-1-one,
[26] ((5a,8a-trans)-5a,6,8,8a-tetrahydropyrrolo[3,4-b][1,2,3]triazolo[1,5-d][1,4] oxazin-7(4H)-yl)(thiophen-2-yl)methanone,
[27] phenyl((5a,8a-trans)-3-phenyl-5a,6,8,8a-tetrahydropyrrolo[3,4-b][1,2,3] triazolo[1,5-d][1,4]oxazin-7(4H)-yl)methanone,
[28] 3-phenyl-1-((5a,8a-trans)-3-phenyl-5a,6,8,8a-tetrahydropyrrolo[3,4-b][1,2,3]triazolo[1,5-d][1,4]oxazin-7(4H)-yl)propan-1-one,
[29] 1-((5a,8a-trans)-3-phenyl-5a,6,8,8a-tetrahydropyrrolo[3,4-b][1,2,3] triazolo[1,5-d][1,4]oxazin-7(4H)-yl)butan-1-one,
[30] ((5a,8a-trans)-3-phenyl-5a,6,8,8a-tetrahydropyrrolo[3,4-b][1,2,3]triazolo[1,5-d][1,4]oxazin-7(4H)-yl)(thiophen-2-yl)methanone,
[31] (5a,8a-trans)-N-butyl-5a,6,8,8a-tetrahydropyrrolo[3,4-b][1,2,3]triazolo[1,5-d][1,4]oxazine-7(4H)-carboxamide,
[32] (5a,8a-trans)-N-phenyl-5a,6,8,8a-tetrahydropyrrolo[3,4-b][1,2,3]triazolo[1,5-d][1,4]oxazine-7(4H)-carboxamide,
[33] (5a,8a-trans)-N,3-diphenyl-5a,6,8,8a-tetrahydropyrrolo[3,4-b][1,2,3] triazolo[1,5-d][1,4]oxazine-7(4H)-carboxamide,
[34] (5a,8a-trans)-benzyl 3-phenyl-5a,6,8,8a-tetrahydropyrrolo[3,4-b][1,2,3] triazolo[1,5-d][1,4]oxazine-7(4H)-carboxylate,
[35] (5a,8a-trans)-7-(pyrimidin-2-yl)-4,5a,6,7,8,8a-hexahydropyrrolo[3,4-b][1,2,3]triazolo[1,5-d][1,4]oxazine,
[36] (5a,8a-trans)-7-ethyl-4,5a,6,7,8,8a-hexahydropyrrolo[3,4-b][1,2,3] triazolo[1,5-d][1,4]oxazine,
[37] (5a,8a-trans)-7-pentyl-4,5a,6,7,8,8a-hexahydropyrrolo[3,4-b][1,2,3] triazolo[1,5-d][1,4]oxazine,
[38] (5a,8a-trans)-7-(4-fluorobenzyl)-4,5a,6,7,8,8a-hexahydropyrrolo[3,4-b][1,2,3]triazolo[1,5-d][1,4]oxazine,
[39] (5a,8a-trans)-7-(pyridin-2-ylmethyl)-4,5a,6,7,8,8a-hexahydropyrrolo[3,4-b][1,2,3]triazolo[1,5-d][1,4]oxazine,
[40] (5a,8a-trans)-3-phenyl-7-(pyrimidin-2-yl)-4,5a,6,7,8,8a-hexahydro pyrrolo[3,4-b][1,2,3]triazolo[1,5-d][1,4]oxazine,

[41] (5a,8a-trans)-7-pentyl-3-phenyl-4,5a,6,7,8,8a-hexahydropyrrolo[3,4-b][1,2,3]triazolo[1,5-d][1,4]oxazine,
[42] (5a,8a-trans)-7-phenyl-4,5a,6,7,8,8a-hexahydropyrrolo[3,4-b][1,2,3] triazolo[1,5-d][1,4]oxazine,
[43] (5a,8a-trans)-7-(4-chlorophenyl)-4,5a,6,7,8,8a-hexahydropyrrolo[3,4-b][1,2,3]triazolo[1,5-d][1,4]oxazine,
[44] (5a,8a-trans)-7-(pyridin-2-yl)-4,5a,6,7,8,8a-hexahydropyrrolo[3,4-b][1,2,3]triazolo[1,5-d][1,4]oxazine,
[45] (5a,8a-trans)-3,7-diphenyl-4,5a,6,7,8,8a-hexahydropyrrolo[3,4-b][1,2,3] triazolo[1,5-d][1,4]oxazine,
[46] (5a,8a-trans)-7-(4,6-dichloropyrimidin-2-yl)-4,5a,6,7,8,8a-hexahydro pyrrolo[3,4-b][1,2,3]triazolo[1,5-d][1,4]oxazine,
[47] (5a,8a-trans)-7-(4,6-dichloropyrimidin-2-yl)-3-phenyl-4,5a,6,7,8,8a-hexahydro pyrrolo[3,4-b][1,2,3]triazolo[1,5-d][1,4]oxazine,
[48] (5a,8a-trans)-7-(4-chloropyrimidin-2-yl)-3-phenyl-4,5a,6,7,8,8a-hexahydro pyrrolo[3,4-b][1,2,3]triazolo[1,5-d][1,4]oxazine,
[49] (5a,8a-trans)-7-(4-chloropyrimidin-2-yl)-4,5a,6,7,8,8a-hexahydro pyrrolo[3,4-b][1,2,3]triazolo[1,5-d][1,4]oxazine,
[50] 2-((5a,8a-trans)-5a,6,7,8,8a-tetrahydropyrrolo[3,4-b][1,2,3]triazolo[1,5-d][1,4]oxazin-7(4H)-yl)pyrimidin-4-amine,
[51] 2-((5a,8a-trans)-3-phenyl-5a,6,7,8,8a-tetrahydropyrrolo[3,4-b][1,2,3]triazolo[1,5-d][1,4]oxazin-7(4H)-yl)pyrimidin-4-amine,
[52] 6-((5a,8a-trans)-3-phenyl-5a,6,8,8a-tetrahydropyrrolo[3,4-b][1,2,3]triazolo[1,5-d][1,4]oxazin-7(4H)-yl)-1,3,5-triazine-2,4-diamine,
[53] (5aS,8aS)-tert-butyl 5a,6,8,8a-tetrahydropyrrolo[3,4-b][1,2,3]triazolo[1,5-d][1,4]oxazine-7(4H)-carboxylate,
[54] (5aS,8aS)-tert-butyl 3-methyl-5a,6,8,8a-tetrahydropyrrolo[3,4-b][1,2,3] triazolo[1,5-d][1,4]oxazine-7(4H)-carboxylate,
[55] (5aS,8aS)-tert-butyl 3-phenyl-5a,6,8,8a-tetrahydropyrrolo[3,4-b][1,2,3] triazolo[1,5-d][1,4]oxazine-7(4H)-carboxylate,
[56] (5aS,8aS)-tert-butyl 3-(3-fluorophenyl)-5a,6,8,8a-tetrahydropyrrolo[3,4-b][1,2,3]triazolo[1,5-d][1,4]oxazine-7(4H)-carboxylate,
[57] (5aS,8aS)-tert-butyl 3-(4-(trifluoromethyl)phenyl)-5a,6,8,8a-tetrahydro pyrrolo[3,4-b][1,2,3]triazolo[1,5-d][1,4] oxazine-7(4H)-carboxylate, and
[58] (5aS,8S)-4,5a,6,7,8,8a-hexahydropyrrolo[3,4-b][1,2,3] triazolo[1,5-d][1,4] oxazine.

A specific embodiment of the invention is that in which the tricyclic triazolic compounds of the invention represent a compound with the general formula (Ia):

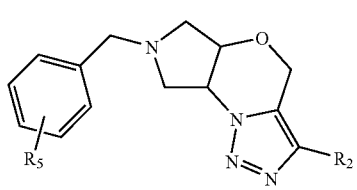

(Ia)

where $R_2$ has the same meanings as in formula (I) and $R_5$ is an hydrogen atom, an halogen atom or a $C_1$-$C_{10}$ alkyloxy.

Also a specific embodiment is one in which the tricyclic triazolic compounds of the invention are represented by the general formula (Ib):

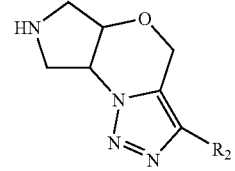

(Ib)

where $R_2$ has the same meanings as in formula (I).

An additional specific embodiment of the invention is provided where tricyclic triazolic compounds of the invention are represented by general formula (Ic):

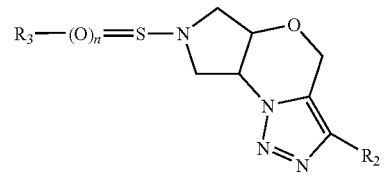

(Ic)

where $R_2$, $R_3$ and n have the same meanings as in formula (I).

Another specific embodiment of the invention is the compounds with the general formula (Id):

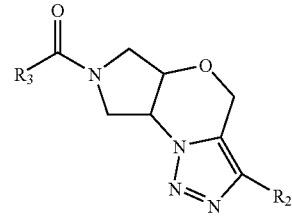

(Id)

where $R_2$ and $R_3$ have the same meanings as in formula (I).

Another specific embodiment is that in which the compounds of the invention have the general formula (Ie):

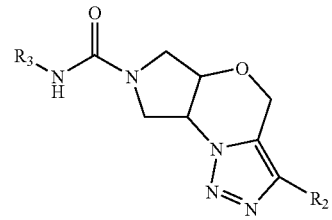

(Ie)

where $R_2$ and $R_3$ have the same meanings as in formula (I).

Another specific embodiment of the invention is the compounds with the general formula (If):

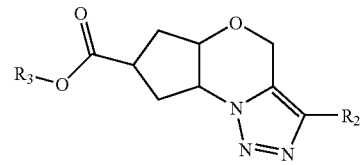

(If)

where $R_2$ and $R_3$ have the same meanings as in formula (I).

Another specific embodiment of the invention is the compounds with the general formula (Ig):

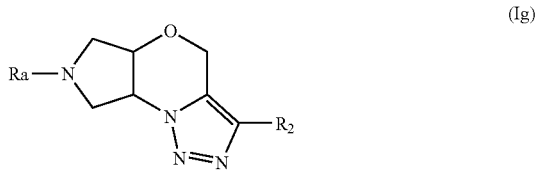
(Ig)

where $R_2$ has the same meanings as in formula (I) and Ra represents an alkyl, aryl, heteroaryl, arylalkyl or heteroarylalkyl.

In another aspect, the invention refers to the processes for obtaining the compounds of general formula (I). Several procedures have been developed for obtaining all the compound derivatives of the invention, herein the procedures will be explained below in methods A to E.

Method A

A process is described for the preparation of a compound of general formula (Ia):

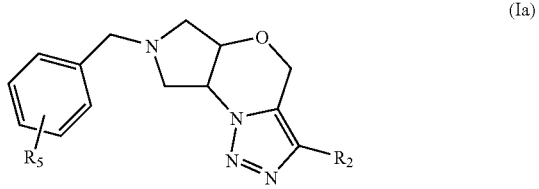
(Ia)

comprising heating compound of general formula (II) wherein $R_2$ and $R_5$ have the same meanings as in formula (I) and formula (Ia):

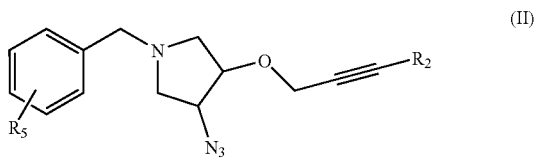
(II)

in toluene or xylene to a temperature of 100-130° C., where $R_2$ has the same meaning as in formula (I) and $R_5$ have the same as in formula (Ia).

The heating process of compound (II) in toluene or xylene may be carried out for a variable period of time, although normally 16 hours should be sufficient. Otherwise, the reaction may be considered finished when TLC analysis shows that the reaction is completed. In a preferred embodiment of the invention the reaction is carried out at 110° C.

Method B

The process for the synthesis of compounds of general formula (Ib) is sequential to that of compounds of formula (Ia)

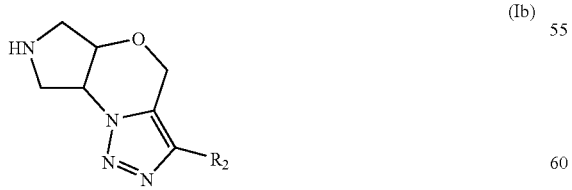
(Ib)

and it comprises the hydrogenolysis of compound (Ia) in the presence of hydrogen and a catalyst in an organic solvent.

The organic solvent in which the reaction is carried out is preferably methanol or THF. In a preferred embodiment the catalyst is a palladium catalyst, preferably a Pd/C10%. The reaction is let to take place under stirring at room temperature and under hydrogen atmosphere. The reaction may take place for 48 hours or until TLC analysis shows completed reaction.

Method C

Another embodiment of the process for the synthesis of compounds falling within general formula (I) may be obtained from compounds of general formula (Ib). Specifically, the preparation of compounds of formula (Ie):

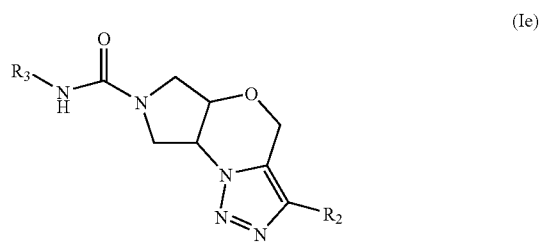
(Ie)

comprises the reaction of a compound of formula (Ib) as define above with an isocyanate of formula (III):

in an organic solvent and optionally in the presence of a supported amine, and wherein $R_2$ and $R_3$ have the same meanings as in formula (I).

In a preferred embodiment of the invention the solvent use for carrying out the reaction is dichloromethane. The reaction is preferably carried out in the presence of a supported amine such as aminomethylated polystyrene. The reaction takes place preferably at room temperature of an estimated time of 16 h.

Method D

Another process for the preparation of compounds of general formula (I) are obtained as specified in method D.

Such a method comprises the reaction between compound (Ib) with a compound of formula (IV):

in an organic solvent and optionally in the presence of a base and/or a catalyst, wherein $R_1$ has the meanings as in formula (I) and X is a halogen.

Preferably the solvent is dichloromethane, acetonitrile, 2-propanol or THF.

In a preferred embodiment, the base used may be selected from diisopropylethylamine, sodium tert-butoxide or otherwise supported amines such as morpholinomethyl polystyrene or aminomethylated polystyrene.

Further, specific embodiments contemplate the possibility of using a palladium catalyst such as one of the following formula (XX) wherein $R_1$ is defined as in formula (I):

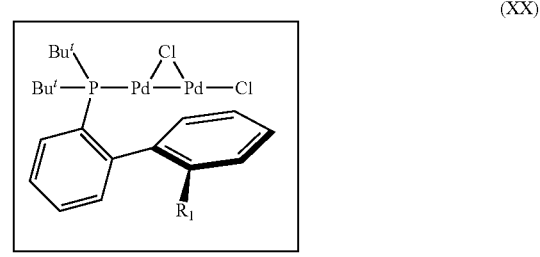
(XX)

For some embodiments reactive (IV) may be more specifically represented as (IV'):

where $R_3$ has the same meaning as in formula (I), X is a halogen and G represents —$SO_2$—, —CO— or —OCO—.

Method D1

The compound formula (Ib) when treated with a compound of formula (V) as defined above in presence of a base preferably diisopropylethylamine, or alternatively in presence of supported amines preferably morpholinomethyl polystyrene and aminomethylated polystyrene in a solvent as dichloromethane, will give a compound of formula (Ic) as defined hereinafter where $R_3$ and $R_2$ have the meaning as defined above.

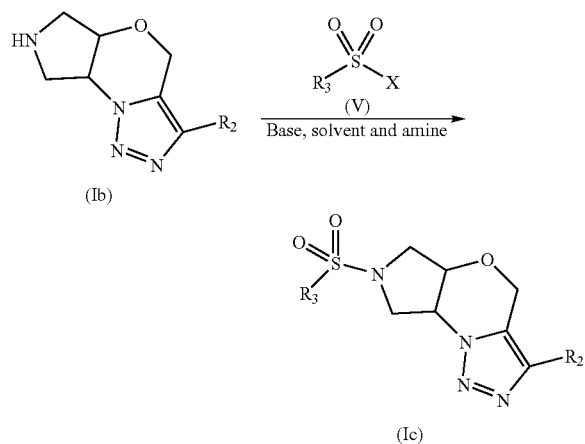

Method D2

The compound formula (Ib) when treated with a compound of formula (VI) in presence of a base preferably diisopropylethylamine, or alternatively in presence of supported amines preferably morpholinomethyl polystyrene and aminomethylated polystyrene in a solvent preferably dichloromethane, will give a compound formula (Id) as defined hereinafter where $R_3$ and $R_2$ have the meaning as defined above.

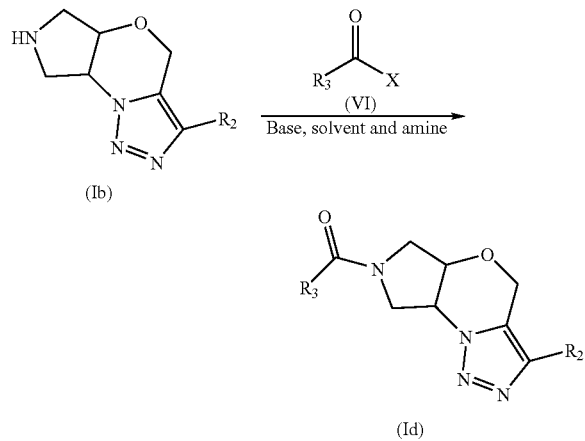

Method D3

The compound of formula (Ib) when treated with a compound of formula (VII) in presence of a base preferably diisopropylethylamine, or alternatively in presence of supported amines preferably morpholinomethyl polystyrene and aminomethylated polystyrene in a solvent preferably dichloromethane, will give a compound formula (If) as defined hereinafter where $R_1$ and $R_2$ have the meaning as defined above.

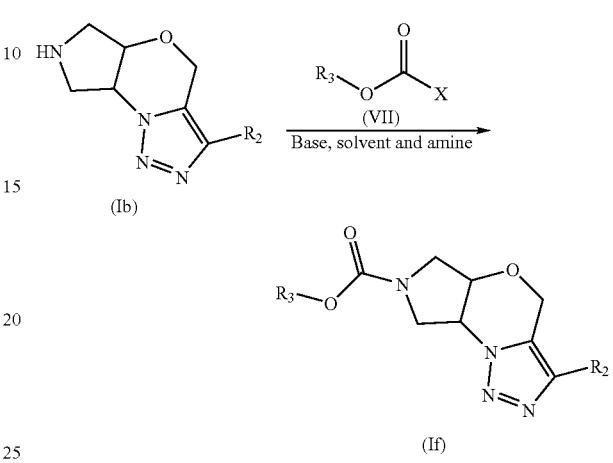

Method D4

The compound of formula (Ib) when treated with a compound of formula (IV) in presence of a base preferably diisopropylethylamine in dichloromethane at room temperature, or alternatively in a solvent preferably acetonitrile or 2-propanol under heated microwave conditions, preferentially between 80 and 130° C., will give a compound of formula (I) as defined hereinafter where $R_1$ and $R_2$ have the meaning as defined above.

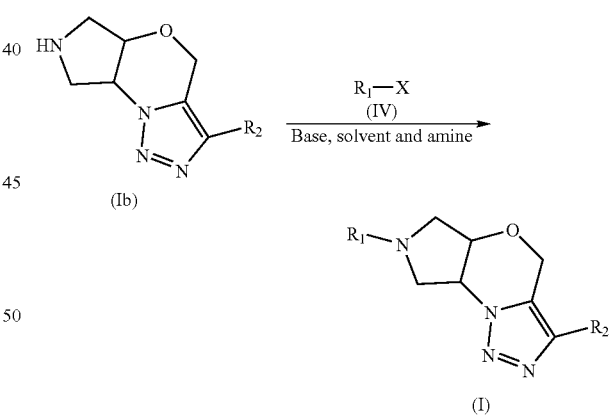

Method D5

N-Aryl derivatives compounds of formula (Ig) as defined hereinafter can be prepared by N-Arylation reaction with palladium catalysis following methods adapted from the literature (JACS 2006, 128, 6376-6390). The compound of formula (Ib) as defined above when treated with an aryl halide of formula (VIII) define above in presence of a palladium catalyst of formula (XX) and a base preferably sodium tert-butoxide in a solvent preferably THF at room temperature, will provide compounds of formula (Ig) where $R_1$ and $R_2$ have the meaning as defined above.

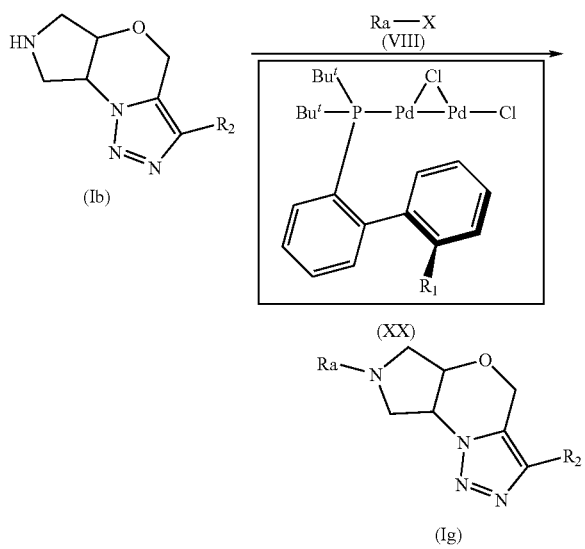

Method E

In another aspect of the present invention relates to a process for obtaining enantiomerically pure compounds of formula (I) as defined above and comprises:

a) the reaction of compound of formula (XII), or its enantiomer:

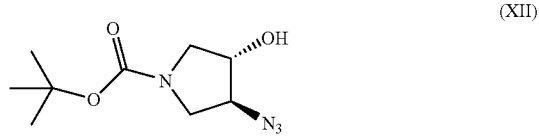 [SMILES: CC(C)(C)OC(=O)N1C[C@H](N=[N+]=[N-])[C@@H](O)C1]

with a compound of formula (Z) wherein X is halogen atom in an organic solvent:

b) heating the resulting compound of general formula (XIII) or its enantiomer in xylene or toluene:

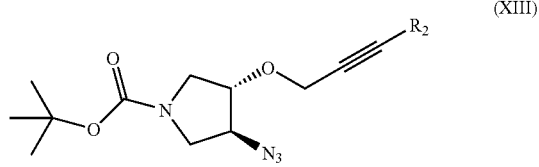

c) hydrolyzing the resulting compound of formula (If') or its enantiomer in an acidic medium:

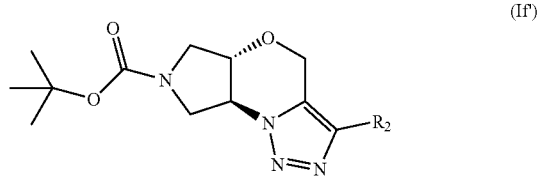

d) reacting the resulting compound of formula (Ib) with compound (IV) in an organic solvent and optionally in the presence of a base and a catalyst, or with compound (III) as defined above in an organic solvent and optionally in the presence of a supported amine, and wherein $R_2$ has the same meanings of formula (I).

In general terms enantiomerically pure compounds of general formula (I), can be prepared with a similar synthetic sequence as that already disclosed in methods A to D but starting from enantiomerically pure compound of formula (XII). Compound of formula (XII) can be prepared enantiomerically pure following methods reported in the literature (J. Org. Chem. 1997, 62, 4197-4199).

The compounds of formula (XII) when treated with a compound of formula (Z) in a solvent such preferably THF, in presence of a base preferably sodium hydride will provide a compound of formula (XIII), which when heated preferably at 100-130° C. in a solvent preferably toluene or xylene will provide a compound of formula (If'). Enantiomerically pure compounds of formula (Ib) as defined above could be prepared by removing the tert-butoxycarbonyl protecting group of compounds of formula (If') by usual conditions as treatment with HCl in a solvent preferably dioxane. From enantiomerically pure compound of formula (Ib), enantiomerically pure compound of formula I may be obtained following methods C and D.

An additional aspect of the invention relates to the therapeutic use of the compounds of general formula (I). As mentioned above, compounds of general formula (I) show a strong affinity to sigma receptors and can behave as agonists, antagonists, inverse agonists, partial antagonists or partial agonists thereof. For this reason, they are suitable for the treatment and the prophylaxis of disorders and diseases mediated by sigma receptors, especially, sigma-1 receptors. In this sense, compounds of formula (I) are very good anxiolitic and immunosuppressant and are very useful in the treatment and prophylaxis of diarrhea, lipoprotein disorders, hyperlipidemia, hypertriglyceridemia, hypercholesterolemia, obesity, migraine, arthritis, hypertension, arrhythmia, ulcer, glaucoma, learning, memory and attention deficits, cognition disorders, neurodegenerative diseases, demyelinating diseases, addiction to drugs and chemical substances including cocaine, amphetamine, ethanol and nicotine; tardive dyskinesia, ischemic stroke, epilepsy, stroke, stress, cancer, psychotic conditions, in particular depression, anxiety or schizophrenia; inflammation or autoimmune diseases.

The compounds of formula (I) are especially suited for the treatment of pain, especially neuropathic pain, inflammatory pain or other pain conditions involving allodynia and/or hyperalgesia. PAIN is defined by the International Association for the Study of Pain (IASP) as ""an unpleasant sensory and emotional experience associated with actual or potential tissue damage, or described in terms of such damage (IASP, Classification of chronic pain, 2nd Edition, IASP Press (2002), 210). Even though pain is always subjective its causes or syndromes can be classified.

Another aspect of the invention is a pharmaceutical composition which comprises a compound of general formula I or a pharmaceutically acceptable salt, prodrug, isomer or solvate thereof, and at least a pharmaceutically acceptable carrier, additive, adjuvant or vehicle.

The auxiliary materials or additives can be selected among carriers, excipients, support materials, lubricants, fillers, solvents, diluents, colorants, flavor conditioners such as sugars, antioxidants and/or agglutinants In the case of suppositories, this may imply waxes or fatty acid esters or preservatives, emulsifiers and/or carriers for parenteral application The selection of these auxiliary materials and/or additives and the amounts to be used will depend on the form of application of the pharmaceutical composition.

The pharmaceutical composition in accordance with the invention can be adapted to any form of administration, be it orally or parenterally, for example pulmonarily, nasally, rectally and/or intravenously. Therefore, the formulation in accordance with the invention may be adapted for topical or systemic application, particularly for dermal, subcutaneous, intramuscular, intra-articular, intraperitoneal, pulmonary, buccal, sublingual, nasal, percutaneous, vaginal, oral or parenteral application.

Suitable preparations for oral applications are pills, chewing gums, capsules, granules, drops or syrups.

Suitable preparations for parenteral applications are solutions, suspensions, dry preparations that could be reconstituted or sprays.

The compounds of the invention as deposits in dissolved form or in patches, for percutaneous application.

Skin applications include ointments, gels, creams, lotions, suspensions or emulsions The preferred form of rectal application is by means of suppositories.

The amount of active ingredient that must be administered to the patient depends on the patient's weight, the type of application, the condition and severity of the disease Normally, in human beings 1 to 500 mg of the active compound is administered daily in one or several doses.

Described below are a number of examples by way of illustration of the invention and do not limit it in anyway. Starting materials are commercially available and easily obtained by known procedures from commercially available substrates.

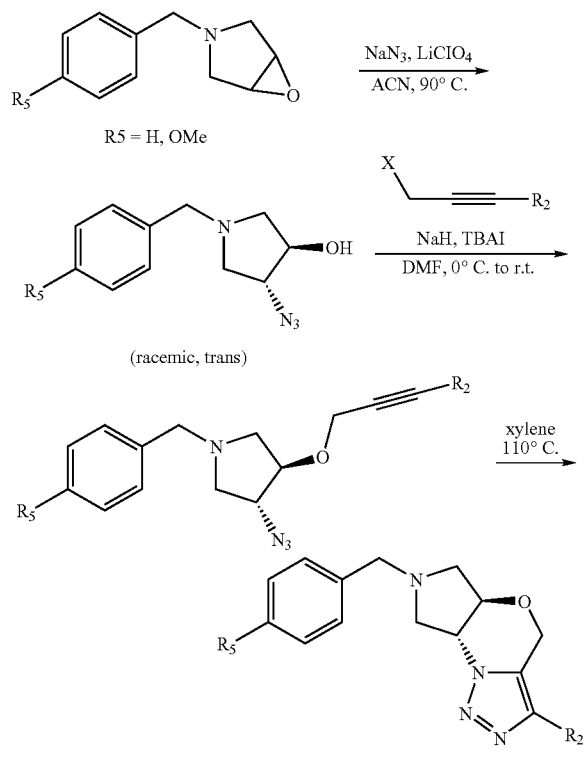

Scheme 1.

R5 = H, OMe (racemic, trans)

Intermediate Compounds

A: 3-(4-methoxybenzyl)-6-oxa-3-azabicyclo[3.1.0]hexane

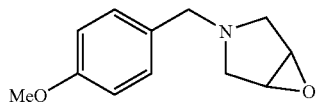 [SMILES: COc1ccc(CN2CC3OC3C2)cc1]

To a solution of 4-methoxybenzyl-3-pyrroline (3.0 g, 15.8 mmol) in methanol (12 ml) cooled at 0° C., water was added (3 ml) and H$_2$SO$_4$ 96% (1.0 ml, 19.0 mmol). The solution was stirred for 10 min. and 3-chloroperoxybenzoic acid (5.0 g, 20.5 mmol) was added in portions. The suspension was stirred at room temperature for 18 hours. Methanol was evaporated, water (15 ml) was added and the aqueous solution was neutralized with aq. NaOH 20% until pH=7. The suspension was extracted with dichloromethane and the organic phase was washed with saturated solution of NaHCO$_3$, water and saturated solution of NaCl, dried over Na$_2$SO$_4$, filtered and concentrated. The residue was purified by flash chromatography: silica gel, gradient hexane:ethyl acetate (1:1) to neat ethyl acetate to give the titled compound (1.92 g, 59% yield) as yellow oil.

$^1$H NMR (400 MHz, CDCl3): δ (ppm) 7.20 (d, J=8.5 Hz, 2H), 6.83 (d, J=8.5 Hz, 2H), 3.78 (s, 3H), 3.64 (s, 2H), 3.60 (s, 2H), 3.16 (d, J=11.7 Hz, 2H), 2.50 (d, J=11.7 Hz, 2H). $^{13}$C NMR (100 MHz, CDCl$_3$): δ (ppm) 158.67, 129.90, 130.76, 113.52, 59.26, 55.84, 55.16, 53.21. MS (EI+) m/z: 206.1 (M+H$^+$), 228.1 (M+Na$^+$).

B: (3,4-trans)-4-azido-1-(4-methoxybenzyl)pyrrolidin-3-ol

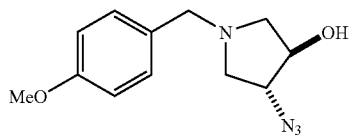 [SMILES: COc1ccc(CN2C[C@@H](O)[C@H](N=[N+]=[N-])C2)cc1]

To a solution of 3-(4-methoxybenzyl)-6-oxa-3-azabicyclo[3.1.0]hexane (100 mg, 0.48 mmol) in acetonitrile (3 ml), NaN$_3$ (158 mg, 2.43 mmol) and LiClO$_4$ (51 mg, 4.8 mmol) were added. The reaction mixture was heated at 80° C. with stirring for 16 hours. After cooling at room temperature, water was added and extracted with ethyl acetate. The combined organic layers were washed with water and sat. solution of NaCl, dried over Na$_2$SO$_4$, filtered and concentrated under reduced pressure to give the title compound (100 mg, 82% yield).

$^1$H NMR (400 MHz, CDCl3): δ (ppm) 7.23 (d, J=9.0 Hz, 2H), 6.87 (d, J=9.0 Hz, 2H), 4.21 (m, 1H), 3.82 (s, 3H), 3.80 (m, 1H), 3.60 (AB system, 2H), 3.08 (dd, J1=6.7 Hz, J2=10.4 Hz, 1H), 2.85 (dd, J1=6.0 Hz, J2=10.4 Hz, 1H), 2.59 (dd, J1=3.7 Hz, J2=10.4 Hz, 1H), 2.45 (dd, J1=4.7 Hz, J2=10.4 Hz, 1H). $^{13}$C NMR (100 MHz, CDCl$_3$): δ (ppm) 158.90, 130.07, 129.73, 113.80, 76.28, 67.75, 61.09, 59.81, 59.22, 55.28. MS (EI+) m/z: 249.1 (M+H$^+$), 271.1 (M+Na$^+$).

C: (3,4-trans)-4-azido-1-benzylpyrrolidin-3-ol

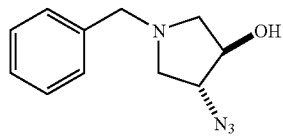

To a solution of 3-benzyl-6-oxa-3-azabicyclo[3.1.0]hexane (7.08 g, 108 mmol) in acetonitrile (20 ml), NaN$_3$ (7.08 g, 108 mmol) and LiClO$_4$ (4.70 g, 43.3 mmol) were added. The reaction mixture was heated at 95° C. with stirring for 16 hours. After cooling at room temperature, water (20 ml) was added and extracted with ethyl acetate (3×20 ml). The combined organic layers was washed with water and sat. solution of NaCl, dried over Na$_2$SO$_4$, filtered and concentrated under reduced pressure to give the title compound (4.28 g, 90% yield).

$^1$H NMR (400 MHz, CDCl3): δ (ppm) 7.31 (m, 5H), 4.20 (m, 1H), 3.80 (m, 1H), 3.65 (m, 2H), 3.08 (m, 1H), 2.86 (m, 1H), 2.60 (m, 1H), 2.46 (m, 1H). $^{13}$C NMR (100 MHz, CDCl$_3$): δ (ppm) 137.83, 128.71, 128.39, 127.32, 76.39, 67.66, 60.54, 59.63, 57.26, 53.41. HR-MS calc for M+H: 219.1246, obs: 219.1241.

General Procedure for the Synthesis of Derivatives of (3-bromoprop-1-ynyl)benzene To a solution of the corresponding propargylalcohol (3.83 mmol) in anhydrous DCM (15 ml) under Ar, CBr$_4$ (5.75 mmol) was added and the reaction mixture was cooled at 0° C. PPh$_3$ (5.94 mmol) was added slowly. The reaction mixture was allowed to reach room temperature and stirred for 16 hours. Ethanol (2 ml) was added and the reaction mixture stirred for 20 min. The solvent was removed under reduced pressure and the crude purified by flash chromatography, silica gel, hexane.

D: (3-bromoprop-1-ynyl)benzene

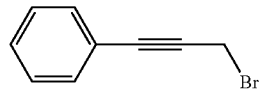

From 3-phenylprop-2-yn-1-ol (828 mg, 6.26 mmol), CBr$_4$ (2.49 g, 7.51 mmol), Ph$_3$P (2.05 g, 7.83 mmol) and DCM (15 ml), afforded the titled compound (1.01 g, 83%).

$^1$H NMR (400 MHz, CDCl3): δ (ppm) 7.47 (m, 2H), 7.34 (m, 3H), 4.18 (s, 2H).

E: 1-(3-bromoprop-1-ynyl)-4-chlorobenzene

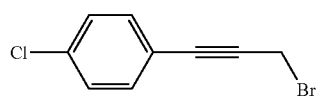 [SMILES: Clc1ccc(C#CCBr)cc1]

From 3-(4-chlorophenyl)prop-2-yn-1-ol (350 mg, 2.64 mmol), CBr$_4$ (2.67 g, 8.07 mmol), Ph$_3$P (2.15 g, 8.20 mmol) and DCM (10 ml), afforded the titled compound (186 mg, 31%).

$^1$H NMR (400 MHz, CDCl3): δ (ppm) 7.34 (m, 4H), 4.16 (s, 2H).

F: 1-(3-bromoprop-1-ynyl)-2-fluorobenzene

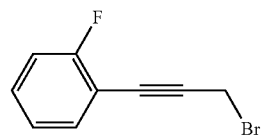 [SMILES: Fc1ccccc1C#CCBr]

From 3-(2-fluorophenyl)prop-2-yn-1-ol (383 mg, 2.55 mmol), CBr$_4$ (2.58 g, 7.77 mmol), Ph$_3$P (2.07 g, 7.90 mmol) and DCM (10 ml), afforded the titled compound (149 mg, 27%).

$^1$H NMR (400 MHz, CDCl3): δ (ppm) 7.46 (m, 1H), 7.34 (m, 1H), 7.11 (m, 2H), 4.20 (s, 2H).

G: 1-(3-bromoprop-1-ynyl)-4-(trifluoromethyl)benzene

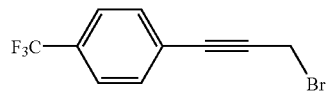 [SMILES: FC(F)(F)c1ccc(C#CCBr)cc1]

From 3-(4-(trifluoromethyl)phenyl)prop-2-yn-1-ol (768 mg, 3.83 mmol), CBr$_4$ (1.90 g, 5.75 mmol), Ph$_3$P (1.56 g, 5.94 mmol) and DCM (15 ml), afforded the titled compound (742 mg, 73%).

$^1$H NMR (400 MHz, CDCl3): δ (ppm) 7.59 (AB system, 4H), 4.17 (s, 2H).

H: 1-(3-bromoprop-1-ynyl)-3-fluorobenzene

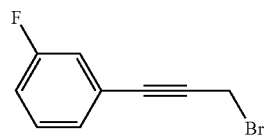 [SMILES: Fc1cccc(C#CCBr)c1]

From 3-(3-fluorophenyl)prop-2-yn-1-ol (614 mg, 4.08 mmol), CBr$_4$ (1.62 g, 4.90 mmol), Ph$_3$P (1.39 g, 5.31 mmol) and DCM (12 ml), afforded the titled compound (634 mg, 73%).

$^1$H NMR (400 MHz, CDCl3): δ (ppm) 7.31 (m, 1H), 7.24 (m, 1H), 7.15 (m, 1H), 7.06 (m, 1H), 4.16 (s, 2H). $^{13}$C NMR (100 MHz, CDCl$_3$): δ (ppm) 162.51 (d, J$_{CF}$=246 Hz), 130.11 (d, J$_{CF}$=9 Hz), 127.90 (d, J$_{CF}$=3 Hz), 124.08 (d, J$_{CF}$=9 Hz), 118.81 (d, J$_{CF}$=23 Hz), 116.41 (d, J$_{CF}$=21 Hz), 85.46, 85.38, 14.91.

General Procedure for the Synthesis of Compounds of General Formula (II)

A solution of azido alcohol (0.8 mmol) in anhydrous THF (5 ml) was cooled to 0° C. and NaH (1.6 mmol, 60% disper-

I: (3,4-trans)-3-azido-1-(4-methoxybenzyl)-4-(prop-2-ynyloxy)pyrrolidine

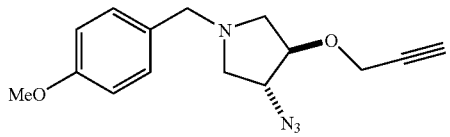 [SMILES: C#CCO[C@@H]1CN(Cc2ccc(OC)cc2)C[C@H]1N=[N+]=[N-]]

From (3,4-trans)-4-azido-1-(4-methoxybenzyl)pyrrolidin-3-ol (300 mg, 1.20 mmol), NaH (96 mg, 2.41 mmol), propargyl bromide (80% solution in toluene, 0.269 ml, 2.41 mmol), tetrabutyl ammonium iodide (44 mg, 0.12 mmol) and THF (10 ml), afforded the titled compound (263 mg, 76% yield).

$^1$H NMR (400 MHz, CDCl3): δ (ppm) 7.24 (d, J=8.8 Hz, 2H), 6.87 (d, J=8.8 Hz, 2H), 4.19 (m, 2H), 4.15 (m, 1H), 3.86 (m, 1H), 3.81 (s, 3H), 3.58 (AB system, 2H), 3.05 (dd, J1=6.8 Hz, J2=10.2 Hz, 1H), 2.85 (dd, J1=6.4 Hz, J2=10.2 Hz, 1H), 2.65 (dd, J1=4.2 Hz, J2=10.2 Hz, 1H), 2.49 (m, 2H). $^{13}$C NMR (100 MHz, CDCl$_3$): δ (ppm) 158.82, 130.25, 130.04, 113.85, 83.27, 74.99, 65.11, 59.03, 58.41, 57.35, 57.11, 55.25. MS (EI+) m/z: 287.2 (M+H$^+$), 309.1 (M+Na$^+$).

J: (3,4-trans)-3-azido-4-(but-2-ynyloxy)-1-(4-methoxybenzyl)pyrrolidine

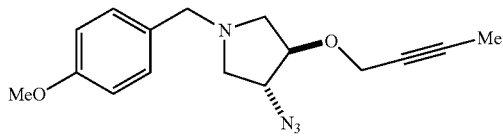 [SMILES: CC#CCO[C@@H]1CN(Cc2ccc(OC)cc2)C[C@H]1N=[N+]=[N-]]

From (3,4-trans)-4-azido-1-(4-methoxybenzyl)pyrrolidin-3-ol (200 mg, 0.80 mmol), NaH (64 mg, 1.61 mmol), 1-bromo-2-butyne (212 mg, 1.60 mmol), tetrabutyl ammonium iodide (30 mg, 0.08 mmol) and THF (5 ml), afforded the titled compound (210 mg, 87% yield).

$^1$H NMR (400 MHz, CDCl3): δ (ppm) 7.24 (d, J=8.7 Hz, 2H), 6.87 (d, J=8.7 Hz, 2H), 4.15 (s, 2H), 4.14 (m, 1H), 3.85 (m, 1H), 3.82 (s, 3H), 3.58 (AB system, 2H), 3.05 (dd, J1=6.7 Hz, J2=10.3 Hz, 1H), 2.84 (dd, J1=6.5 Hz, J2=10.3 Hz, 1H), 2.66 (dd, J1=3.8 Hz, J2=10.2 Hz, 1H), 2.46 (dd, J1=4.5 Hz, J2=10.2 Hz, 1H), 1.87 (t, J=2.3 Hz, 3H). $^{13}$C NMR (100 MHz, CDCl$_3$): δ (ppm) 158.82, 130.02, 129.91, 113.70, 83.15, 82.88, 74.51, 65.14, 59.07, 58.50, 57.68, 57.39, 55.26, 3.62. HR-MS calc for M+Na: 323.1484, obs: 323.1478.

K: (3,4-trans)-3-azido-1-(4-methoxybenzyl)-4-(pent-2-ynyloxy)pyrrolidine

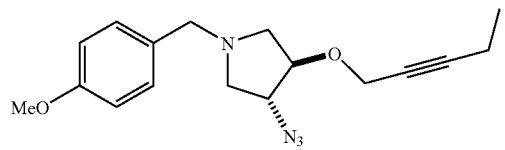 [SMILES: CCC#CCO[C@@H]1CN(Cc2ccc(OC)cc2)C[C@H]1N=[N+]=[N-]]

From (3,4-trans)-4-azido-1-(4-methoxybenzyl)pyrrolidin-3-ol (200 mg, 0.80 mmol), NaH (64 mg, 1.61 mmol), 1-bromo-2-pentyne (236 mg, 1.60 mmol), tetrabutyl ammonium iodide (30 mg, 0.08 mmol) and THF (5 ml), afforded the titled compound (130 mg, 51% yield).

$^1$H NMR (400 MHz, CDCl3): δ (ppm) 7.24 (d, J=8.8 Hz, 2H), 6.87 (d, J=8.8 Hz, 2H), 4.16 (m, 3H), 3.85 (m, 1H), 3.81 (s, 3H), 3.58 (AB system, 2H), 3.05 (dd, J1=6.7 Hz, J2=10.3 Hz, 1H), 2.84 (dd, J1=6.2 Hz, J2=10.0 Hz, 1H), 2.66 (dd, J1=4.1 Hz, J2=10.2 Hz, 1H), 2.46 (dd, J1=4.7 Hz, J2=10.0 Hz, 1H), 2.24 (m, 2H), 1.15 (t, J=7.3 Hz, 3H). $^{13}$C NMR (100 MHz, CDCl$_3$): δ (ppm) 158.81, 130.09, 129.89, 113.69, 88.93, 82.89, 74.70, 65.14, 59.07, 58.56, 57.71, 57.40, 55.24, 13.64, 12.45. HR-MS calc for M+H: 315.1821, obs: 315.1830.

L: (3,4-trans)-3-azido-4-(but-2-ynyloxy)-1-(4-methoxybenzyl)pyrrolidine

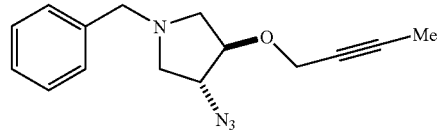 [SMILES: CC#CCO[C@@H]1CN(Cc2ccccc2)C[C@H]1N=[N+]=[N-]]

From (3,4-trans)-4-azido-1-benzylpyrrolidin-3-ol (479 mg, 2.19 mmol), NaH (175 mg, 4.38 mmol), 1-bromo-2-butyne (583 mg, 4.38 mmol), tetrabutyl ammonium iodide (81 mg, 0.21 mmol) and THF (10 ml), afforded the titled compound (456 mg, 77% yield).

$^1$H NMR (400 MHz, CDCl3): δ (ppm) 7.33 (m, 5H), 4.15 (s, 2H), 3.86 (m, 1H), 3.64 (AB system, 2H), 3.09 (dd, J1=6.7 Hz, J2=10.3 Hz, 1H), 2.86 (dd, J1=6.5 Hz, J2=10.3 Hz, 1H), 2.69 (dd, J1=4.0 Hz, J2=10.3 Hz, 1H), 2.50 (dd, J1=4.4 Hz, J2=10.0 Hz, 1H), 1.87 (t, J=2.3 Hz, 3H). $^{13}$C NMR (100 MHz, CDCl$_3$): δ (ppm) 138.02, 128.72, 128.34, 127.20, 83.15, 82.91, 74.53, 65.16, 60.45, 58.65, 57.70, 57.55, 3.62. HR-MS calc for M+H: 271.1559, obs: 271.1563.

M: (3,4-trans)-3-azido-1-benzyl-4-(pent-2-ynyloxy)pyrrolidine

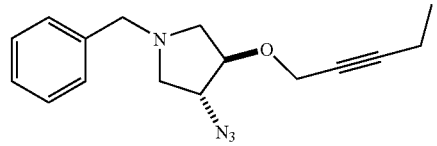 [SMILES: CCC#CCO[C@@H]1CN(Cc2ccccc2)C[C@H]1N=[N+]=[N-]]

From (3,4-trans)-4-azido-1-benzylpyrrolidin-3-ol (414 mg, 1.89 mmol), NaH (151 mg, 3.79 mmol), 1-bromo-2-pentyne (557 mg, 3.79 mmol), tetrabutyl ammonium iodide (70 mg, 0.189 mmol) and THF (10 ml), afforded the titled compound (484 mg, 90% yield).

$^1$H NMR (400 MHz, CDCl3): δ (ppm) 7.28 (m, 5H), 4.17 (m, 3H), 3.86 (m, 1H), 3.64 (AB system, 2H), 3.09 (dd, J1=6.6 Hz, J2=10.0 Hz, 1H), 2.86 (dd, J1=6.5 Hz, J2=10.2 Hz, 1H), 2.69 (dd, J1=3.9 Hz, J2=10.2 Hz, 1H), 2.50 (dd, J1=4.8 Hz, J2=10.0 Hz, 1H), 2.24 (m, 2H), 1.16 (t, J=7.6 Hz, 3H). $^{13}$C NMR (100 MHz, CDCl$_3$): δ (ppm) 138.01, 128.73, 128.33, 127.20, 88.97, 82.90, 74.67, 65.15, 59.76, 58.67, 57.74, 57.53, 13.64, 12.45. HR-MS calc for M+H: 285.1715, obs: 285.1712.

N: (3,4-trans)-3-azido-1-benzyl-4-(3-(4-chlorophenyl)prop-2-ynyloxy)pyrrolidine

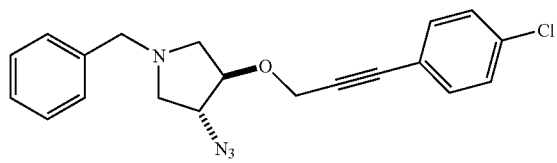 [SMILES: [N-]=[N+]=N[C@@H]1CN(Cc2ccccc2)C[C@H]1OCC#Cc1ccc(Cl)cc1]

From (3,4-trans)-4-azido-1-benzylpyrrolidin-3-ol (150 mg, 0.68 mmol), NaH (55 mg, 1.37 mmol), 1-(3-bromoprop-1-ynyl)-4-chlorobenzene (157 mg, 0.68 mmol), tetrabutyl ammonium iodide (25 mg, 0.068 mmol) and THF (5 ml), afforded the titled compound (154 mg, 61% yield).

$^1$H NMR (400 MHz, CDCl3): δ (ppm) 7.34 (m, 9H), 4.41 (s, 2H), 4.23 (m, 1H), 3.92 (m, 1H), 3.65 (AB system, 2H), 3.10 (dd, J1=6.5 Hz, J2=10.0 Hz, 1H), 2.90 (dd, J1=6.5 Hz, J2=10.0 Hz, 1H), 2.70 (dd, J1=3.9 Hz, J2=10.1 Hz, 1H), 2.56 (dd, J1=4.7 Hz, J2=10.1 Hz, 1H). $^{13}$C NMR (100 MHz, CDCl$_3$): δ (ppm) 137.95, 134.72, 133.03, 128.74, 128.69, 128.37, 127.26, 120.84, 85.62, 85.49, 83.37, 65.18, 59.77, 58.63, 57.92, 57.53. HR-MS calc for M+H: 367.1326, obs: 367.1313.

O: (3,4-trans)-3-azido-1-benzyl-4-(3-(2-fluorophenyl)prop-2-ynyloxy)pyrrolidine

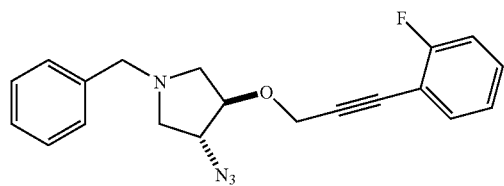 [SMILES: [N-]=[N+]=N[C@@H]1CN(Cc2ccccc2)C[C@H]1OCC#Cc1ccccc1F]

From (3,4-trans)-4-azido-1-benzylpyrrolidin-3-ol (150 mg, 0.68 mmol), NaH (55 mg, 1.37 mmol), 1-(3-bromoprop-1-ynyl)-2-fluorobenzene (146 mg, 0.68 mmol), tetrabutyl ammonium iodide (25 mg, 0.068 mmol) and THF (5 ml), afforded the titled compound (120 mg, 50% yield).

$^1$H NMR (400 MHz, CDCl3): δ (ppm) 7.44 (m, 1H), 7.34 (m, 6H), 7.10 (m, 2H), 4.46 (s, 2H), 4.25 (m, 1H), 3.94 (m, 1H), 3.66 (AB system, 2H), 3.12 (dd, J1=6.5 Hz, J2=10.4 Hz, 1H), 2.90 (dd, J1=6.5 Hz, J2=9.8 Hz, 1H), 2.71 (dd, J1=4.1 Hz, J2=10.1 Hz, 1H), 2.59 (dd, J1=4.4 Hz, J2=10.1 Hz, 1H). $^{13}$C NMR (100 MHz, CDCl$_3$): δ (ppm) 163.0 (d, J$_{CF}$=252 Hz), 137.98, 133.65, 130.40 (d, J$_{CF}$=8 Hz), 128.74, 128.36, 127.22, 123.94 (d, J$_{CF}$=4 Hz), 115.50 (d, J$_{CF}$=24 Hz), 110.90 (d, J$_{CF}$=20 Hz), 89.74, 83.43, 80.18, 65.19, 59.77, 58.65, 57.98, 57.47. HR-MS calc for M+H: 351.1621, obs: 351.1621.

P: (3,4-trans)-3-azido-1-benzyl-4-(3-(4-(trifluoromethyl)phenyl)prop-2-nyloxy)pyrrolidine

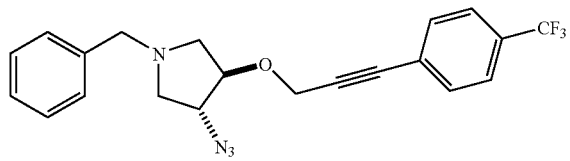 [SMILES: [N-]=[N+]=N[C@@H]1CN(Cc2ccccc2)C[C@H]1OCC#Cc1ccc(C(F)(F)F)cc1]

From (3,4-trans)-4-azido-1-benzylpyrrolidin-3-ol (150 mg, 0.68 mmol), NaH (55 mg, 1.37 mmol), 1-(3-bromoprop-1-ynyl)-4-(trifluoromethyl)benzene (219 mg, 1.03 mmol), tetrabutyl ammonium iodide (25 mg, 0.068 mmol) and THF (5 ml), afforded the titled compound (95 mg, 35% yield).

$^1$H NMR (400 MHz, CDCl3): δ (ppm) 7.58 (AB system, 4H), 7.30 (m, 5H), 4.44 (s, 2H), 4.24 (m, 1H), 3.93 (m, 1H), 3.66 (AB system, 2H), 3.11 (dd, J1=6.6 Hz, J2=10.2 Hz, 1H), 2.93 (dd, J1=6.6 Hz, J2=10.1 Hz, 1H), 2.72 (dd, J1=4.0 Hz, J2=10.1 Hz, 1H), 2.58 (dd, J1=4.6 Hz, J2=10.1 Hz, 1H). $^{13}$C NMR (100 MHz, CDCl$_3$): δ (ppm) 137.93, 132.02, 130.22 (q, J=32 Hz), 128.74, 128.38, 127.27, 125.26 (q, J=4 Hz), 124.27 (q, J=272 Hz), 87.02, 85.34, 83.49, 65.19, 59.76, 58.59, 57.85, 57.52. HR-MS calc for M+H: 401.1589, obs: 401.1594.

Q: (3,4-trans)-3-azido-1-benzyl-4-(3-(3-fluorophenyl)prop-2-ynyloxy)pyrrolidine

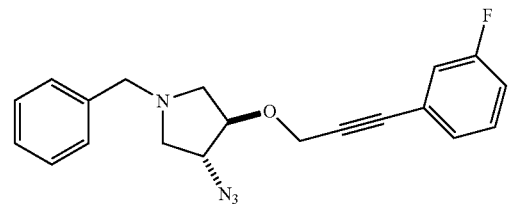 [SMILES: [N-]=[N+]=N[C@@H]1CN(Cc2ccccc2)C[C@H]1OCC#Cc1cccc(F)c1]

From (3,4-trans)-4-azido-1-benzylpyrrolidin-3-ol (100 mg, 0.73 mmol), NaH (58 mg, 1.46 mmol), 1-(3-bromoprop-1-ynyl)-3-fluorobenzene (234 mg, 1.09 mmol), tetrabutyl ammonium iodide (81 mg, 0.21 mmol) and THF (5 ml), afforded the titled compound (120 mg, 47% yield).

$^1$H NMR (400 MHz, CDCl3): δ (ppm) 7.36 (m, 4H), 7.30 (m, 5H), 7.30 (m, 2H), 7.25 (m, 1H), 7.17 (m, 1H), 7.07 (m, 1H), 4.43 (s, 2H), 4.24 (m, 1H), 3.93 (m, 1H), 3.66 (AB system, 2H), 3.12 (dd, J1=6.5 Hz, J2=10.0 Hz, 1H), 2.92 (dd, J1=6.5 Hz, J2=10.2 Hz, 1H), 2.72 (dd, J1=4.0 Hz, J2=10.0 Hz, 1H), 2.58 (dd, J1=4.5 Hz, J2=10.0 Hz, 1H). $^{13}$C NMR (100 MHz, CDCl$_3$): δ (ppm) 162.30 (d, J$_{CF}$=252 Hz), 137.95, 129.95 (d, J=8 Hz), 128.80, 128.39, 127.70 (d, J$_{CF}$=3 Hz), 127.28, 124.20 (d, J$_{CF}$=9 Hz), 118.60 (d, J$_{CF}$=22 Hz), 116.10 (d, J$_{CF}$=22 Hz), 85.53, 85.47, 83.41, 65.18, 59.77, 58.62, 57.86, 57.52. HR-MS calc for M+H: 351.1621, obs: 351.1622.

R: (3,4-trans)-3-azido-1-benzyl-4-(3-phenylprop-2-ynyloxy)pyrrolidine

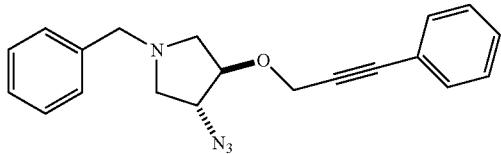 [SMILES: [N-]=[N+]=N[C@@H]1CN(Cc2ccccc2)C[C@H]1OCC#Cc1ccccc1]

From (3,4-trans)-4-azido-1-benzylpyrrolidin-3-ol (200 mg, 0.91 mmol), NaH (73 mg, 1.83 mmol), (3-bromoprop-1-ynyl)benzene (303 mg, 1.55 mmol), tetrabutyl ammonium iodide (203 mg, 0.54 mmol) and THF (5 ml), afforded the titled compound (254 mg, 84% yield).

$^1$H NMR (400 MHz, CDCl3): δ (ppm) 7.48 (m, 2H), 7.32 (m, 8H), 4.45 (s, 2H), 4.28 (m, 1H), 3.95 (m, 1H), 3.68 (AB system, 2H), 3.15 (dd, J1=6.6 Hz, J2=10.3 Hz, 1H), 2.92 (dd, J1=6.6 Hz, J2=10.2 Hz, 1H), 2.72 (dd, J1=3.9 Hz, J2=10.2 Hz, 1H), 2.60 (dd, J1=4.7 Hz, J2=10.3 Hz, 1H). $^{13}$C NMR (100 MHz, CDCl$_3$): δ (ppm) 138.03, 131.83, 128.77, 128.65, 128.40, 128.36, 127.27, 122.42, 86.78, 84.55, 83.31, 65.21, 59.80, 58.70, 58.01, 57.53. HR-MS calc for M+H: 333.1715, obs: 333.1709.

S: (3,4-trans)-3-azido-1-benzyl-4-(prop-2-ynyloxy)pyrrolidine

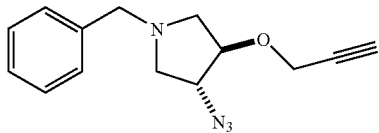 [SMILES: C#CCO[C@@H]1CN(Cc2ccccc2)C[C@H]1N=[N+]=[N-]]

To a suspension of NaH (0.50 g, 20.6 mmol) in dry THF (20 ml) cooled at −15° C., under nitrogen atmosphere, a solution of (3,4-trans)-4-azido-1-benzylpyrrolidin-3-ol (3.0 g, 13.7 mmol) in dry THF (10 ml). After 30 minutes of stirring, propargyl bromide (80% solution in toluene, 2.30 ml, 20.6 mmol) was added, and the reaction mixture was allowed to warm at r.t. and stirred for 16 hours. Saturated solution of NH$_4$Cl was added and extracted with EtOAc. The organic layer was washed with water, dried over Na$_2$SO$_4$, filtered and concentrated under reduced pressure to give the titled compound (3.5 g, 99% yield).

$^1$H NMR (400 MHz, CDCl3): δ (ppm) 7.33 (m, 5H), 4.20 (m, 2H), 4.17 (m, 1H), 3.87 (m, 1H), 3.62 (AB system, 2H), 3.08 (dd, J1=6.4 Hz, J2=10.3 Hz, 1H), 2.89 (dd, J1=6.7 Hz, J2=10.6 Hz, 1H), 2.70 (dd, J1=4.1 Hz, J2=10.3 Hz, 1H), 2.52 (dd, J1=4.5 Hz, J2=10.3 Hz, 1H), 2.48 (t, J=2.5 Hz, 1H). $^{13}$C NMR (100 MHz, CDCl$_3$): δ (ppm) 137.93, 128.71, 128.36, 127.25, 83.28, 79.11, 75.00, 65.12, 59.72, 58.52, 57.47, 57.14. HR-MS calc for M+H: 257.1402, obs: 257.1402.

Preparation of Formula (Xiii)

T: (3S,4S)-tert-butyl 3-azido-4-(prop-2-ynyloxy)pyrrolidine-1-carboxylate

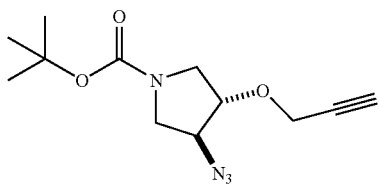 [SMILES: C#CCO[C@H]1CN(C(=O)OC(C)(C)C)C[C@@H]1N=[N+]=[N-]]

From (3S,4S)-tert-butyl 3-azido-4-hydroxypyrrolidine-1-carboxylate (250 mg, 1.09 mmol), NaH (57 mg, 1.42 mmol), propargyl bromide (80% solution in toluene, 0.32 ml, 2.19 mmol), tetrabutyl ammonium iodide (283 mg, 0.76 mmol) and THF (8 ml), afforded the titled compound (268 mg, 92% yield) as yellow oil.

$^1$H NMR (400 MHz, CDCl$_3$): mixture of two rotamers, δ (ppm) 4.20 (m, 2H), 4.08 (m, 1H), 4.03 (m, 1H), 3.58 (m, 2H), 3.40 (m, 2H), 2.48 (s, 1H), 1.43 (s, 9H). $^{13}$C NMR (100 MHz, CDCl$_3$): δ (ppm) 154.16, 80.51, 79.73, 75.42, 63.39, 62.48, 56.91, 49.33, 48.59, 48.56, 48.23. MS (EI+) m/z: 289.1 (M+Na$^+$).

V: (3S,4S)-tert-butyl 3-azido-4-(3-phenylprop-2-ynyloxy)pyrrolidine-1-carboxylate

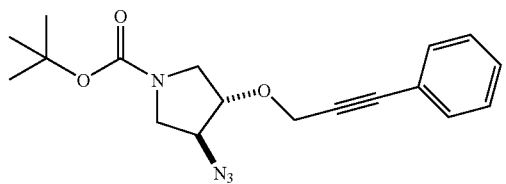 [SMILES: CC(C)(C)OC(=O)N1C[C@H](N=[N+]=[N-])[C@@H](OCC#Cc2ccccc2)C1]

From (3S,4S)-tert-butyl 3-azido-4-hydroxypyrrolidine-1-carboxylate (100 mg, 0.43 mmol), NaH (23 mg, 0.57 mmol), (3-bromoprop-1-ynyl)benzene (102 mg, 0.52 mmol), tetrabutylammonium iodide (113 mg, 0.30 mmol) and THF (4 ml), afforded the titled compound (120 mg, 80% yield) as yellow oil.

$^1$H NMR (400 MHz, CDCl$_3$): mixture of two rotamers, δ (ppm) 7.44 (m, 2H), 7.32 (m, 3H), 4.44 (m, 2H), 4.17 (m, 1H), 4.08 (m, 1H), 3.63 (m, 2H), 3.44 (m, 2H), 1.45 (s, 9H). $^{13}$C NMR (100 MHz, CDCl$_3$): δ (ppm) 154.13, 131.67, 128.71, 128.29, 122.04, 87.11, 83.96, 80.59, 79.87, 79.64, 63.40, 62.61, 57.81, 49.43, 48.72, 48.59, 48.15, 28.32. HR-MS calc for M+Na: 365.1590, obs: 365.1575.

W: (3S,4S)-tert-butyl 3-azido-4-(but-2-ynyloxy)pyrrolidine-1-carboxylate

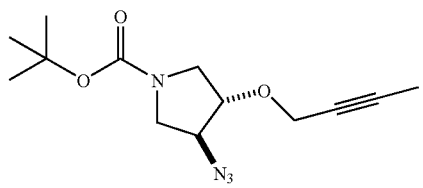 [SMILES: CC#CCO[C@H]1CN(C(=O)OC(C)(C)C)C[C@@H]1N=[N+]=[N-]]

From (3S,4S)-tert-butyl 3-azido-4-hydroxypyrrolidine-1-carboxylate (100 mg, 0.43 mmol), NaH (23 mg, 0.57 mmol), 1-bromo-2-butyne (117 mg, 0.87 mmol), tetrabutylammonium iodide (113 mg, 0.30 mmol) and THF (4 ml), afforded the titled compound (118 mg, 96% yield) as colourless oil.

$^1$H NMR (400 MHz, CDCl$_3$): mixture of two rotamers, δ (ppm) 4.14 (m, 2H), 4.05 (m, 1H), 3.99 (m, 1H), 3.55 (m, 2H), 3.37 (m, 2H), 1.82 (t, J=2.3 Hz, 3H), 1.41 (s, 9H). $^{13}$C NMR (100 MHz, CDCl$_3$): δ (ppm) 154.31, 83.36, 80.12, 79.74, 79.17, 74.02, 63.45, 62.49, 57.43, 49.37, 48.62, 48.55, 48.20, 28.27, 3.42. HR-MS calc for M+Na: 303.1433, obs: 303.1431.

X: (3S,4S)-tert-butyl 3-azido-4-(3-(3-fluorophenyl)prop-2-ynyloxy)pyrrolidine-1-carboxylate

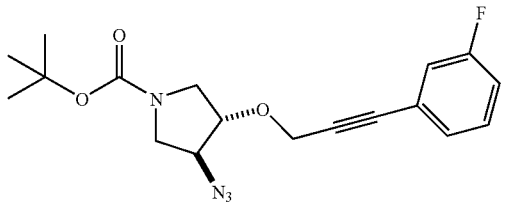 [SMILES: CC(C)(C)OC(=O)N1C[C@H](N=[N+]=[N-])[C@@H](OCC#Cc2cccc(F)c2)C1]

From (3S,4S)-tert-butyl 3-azido-4-hydroxypyrrolidine-1-carboxylate (100 mg, 0.43 mmol), NaH (23 mg, 0.57 mmol), 1-(3-bromoprop-1-ynyl)-3-fluorobenzene (112 mg, 0.52 mmol), tetrabutylammonium iodide (113 mg, 0.30 mmol) and THF (4 ml), afforded the titled compound (144 mg, 91% yield) as yellow oil.

$^1$H NMR (400 MHz, CDCl$_3$): mixture of two rotamers, δ (ppm) 7.25 (m, 2H), 7.14 (m, 1H), 7.04 (m, 1H), 4.44 (m, 2H), 4.16 (m, 1H), 4.08 (m, 1H), 3.64 (m, 2H), 3.46 (m, 2H), 1.46 (s, 9H). $^{13}$C NMR (100 MHz, CDCl$_3$): δ (ppm) 162.21 (d, $J_{CF}$=247 Hz), 154.11, 129.90 (d, $J_{CF}$=8 Hz), 127.56, 123.85 (d, $J_{CF}$=10 Hz), 118.50 (d, $J_{CF}$=23 Hz), 116.03 (d, $J_{CF}$=21 Hz), 85.78, 85.00, 80.72, 79.90, 79.79, 63.49, 62.58, 57.67, 57.60, 49.43, 48.67, 48.57, 48.14, 28.31. HR-MS calc for M+Na: 383.1495, obs: 383.1502.

Y: (3S,4S)-tert-butyl 3-azido-4-(3-(4-(trifluoromethyl)phenyl)prop-2-ynyloxy)pyrrolidine-1-carboxylate

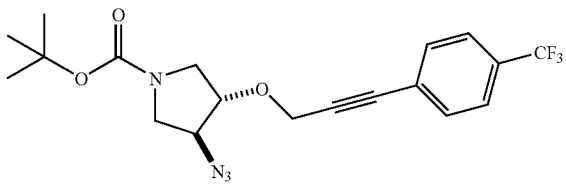 [SMILES: CC(C)(C)OC(=O)N1C[C@H](N=[N+]=[N-])[C@@H](OCC#Cc2ccc(C(F)(F)F)cc2)C1]

From (3S,4S)-tert-butyl 3-azido-4-hydroxypyrrolidine-1-carboxylate (100 mg, 0.43 mmol), NaH (23 mg, 0.57 mmol), 1-(3-bromoprop-1-ynyl)-4-(trifluoromethyl)benzene (138 mg, 0.52 mmol), tetrabutylammonium iodide (113 mg, 0.30 mmol) and THF (4 ml), afforded the titled compound (73 mg, 40% yield) as yellow oil.

$^1$H NMR (400 MHz, CDCl$_3$): mixture of two rotamers, δ (ppm) 7.55 (AB system, 4H), 4.46 (m, 2H), 4.15 (m, 1H), 4.07 (m, 1H), 3.64 (m, 2H), 3.46 (m, 2H), 1.45 (s, 9H). $^{13}$C NMR (100 MHz, CDCl$_3$): δ (ppm) 154.16, 131.95, 130.46 (d, $J_{CF}$=32 Hz), 125.87, 125.28 (q, $J_{CF}$=4 Hz), 125.25, 123.89 (d, $J_{CF}$=272 Hz), 86.52, 85.65, 80.86, 79.99, 63.54, 62.63, 57.66, 49.44, 48.68, 48.60, 48.23, 28.37. HR-MS calc for M+Na: 433.1463, obs: 433.1460.

Examples 1-9

General Procedure for the Synthesis of Compounds of General Formula (Ia)

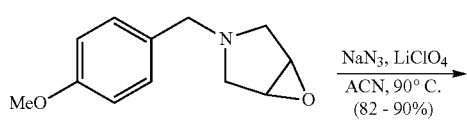

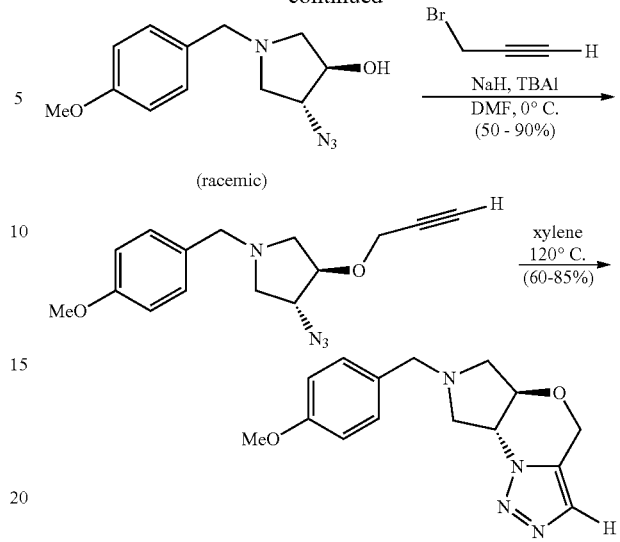

A solution of azido alkyne in toluene or xylene was heated at 110° C. for 16 hours or until TLC analysis shows completed reaction. The solvent was removed under reduced pressure and the residue was purified by flash chromatography, silica gel, gradient hexane:ethyl acetate (3:1) to neat ethyl acetate.

Example 1

(5a,8a-trans)-7-(4-methoxybenzyl)-4,5a,6,7,8,8a-hexahydropyrrolo[3,4-b][1,2,3]triazolo[1,5-d][1,4]oxazine (Compound [1])

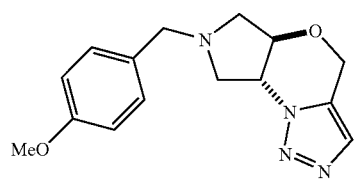

From (3,4-trans)-3-azido-1-(4-methoxybenzyl)-4-(prop-2-ynyloxy)pyrrolidine (137 mg, 0.47 mmol) and toluene (6 ml) afforded the titled compound (97 mg, 71% yield) as white solid. M.p. 150-151° C.

$^1$H NMR (400 MHz, CDCl3): δ (ppm) 7.52 (s, 1H), 7.25 (d, J=8.6 Hz, 2H), 6.88 (d, J=8.6 Hz, 2H), 5.11 (AB system, 2H), 4.30 (m, 1H), 3.95 (m, 1H), 3.85 (m, 2H), 3.81 (s, 3H), 3.69 (dd, J1=7.1 Hz, J2=9.4 Hz, 1H), 3.14 (m, 2H), 3.00 (t, J=9.5 Hz, 1H). $^{13}$C NMR (100 MHz, CDCl$_3$): δ (ppm) 158.94, 130.78, 130.24, 129.77, 128.71, 113.88, 79.28, 63.86, 60.14, 58.89, 55.28, 51.65, 50.59. HR-MS calc for M+H: 287.1508, obs: 287.1503.

Example 2

(5a,8a-trans)-7-(4-methoxybenzyl)-3-methyl-4,5a,6,7,8,8a-hexahydro pyrrolo[3,4-b][1,2,3]triazolo[1,5-d][1,4]oxazine (Compound [2])

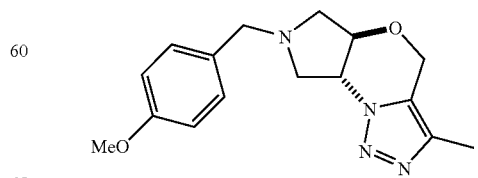

Example 2 can be prepared in the same manner as example 1 from (3,4-trans)-3-azido-4-(but-2-ynyloxy)-1-(4-methoxybenzyl)pyrrolidine (120 mg, 0.40 mmol) and toluene (6 ml) afforded the titled compound (80 mg, 67% yield) as yellow solid.

$^1$H NMR (400 MHz, CDCl3): δ (ppm) 7.23 (d, J=8.6 Hz, 2H), 6.86 (d, J=8.6 Hz, 2H), 5.00 (AB system, 2H), 4.24 (m, 1H), 3.90 (m, 1H), 3.82 (m, 2H), 3.79 (s, 3H), 3.65 (dd, J1=7.0 Hz, J2=9.4 Hz, 1H), 3.14 (dd, J1=7.4 Hz, J2=9.2 Hz, 1H), 3.08 (t, J=9.9 Hz, 1H), 2.97 (t, J=9.5 Hz, 1H), 2.24 (s, 3H). $^{13}$C NMR (100 MHz, CDCl$_3$): δ (ppm) 158.91, 137.54, 130.25, 129.78, 127.26, 113.85, 79.14, 63.74, 60.16, 58.93, 55.26, 51.64, 50.55, 10.14. HR-MS calc for M+H: 301.1665, obs: 301.1664.

Example 3

(5a,8a-trans)-3-ethyl-7-(4-methoxybenzyl)-4,5a,6,7,8,8a-hexahydro pyrrolo[3,4-b][1,2,3]triazolo[1,5-d][1,4]oxazine (Compound [3])

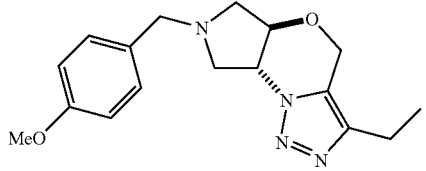

Example 3 can be prepared in the same manner as example 1 from (3,4-trans)-3-azido-1-(4-methoxybenzyl)-4-(pent-2-ynyloxy)pyrrolidine (120 mg, 0.38 mmol) and toluene (5 ml) afforded the titled compound (58 mg, 48% yield) as yellow solid.

$^1$H NMR (400 MHz, CDCl3): δ (ppm) 7.24 (d, J=8.6 Hz, 2H), 6.88 (d, J=8.6 Hz, 2H), 5.04 (AB system, 2H), 4.26 (m, 1H), 3.93 (m, 1H), 3.85 (m, 2H), 3.81 (s, 3H), 3.67 (dd, J1=7.1 Hz, J2=9.4 Hz, 1H), 3.16 (dd, J1=7.4 Hz, J2=9.1 Hz, 1H), 3.10 (t, J=9.9 Hz, 1H), 2.97 (t, J=9.5 Hz, 1H), 2.66 (q, J=7.6 Hz, 2H), 1.25 (t, J=7.6 Hz, 3H). $^{13}$C NMR (100 MHz, CDCl$_3$): δ (ppm) 158.93, 143.35, 130.24, 129.80, 126.71, 113.87, 79.14, 63.86, 60.18, 58.95, 55.28, 51.67, 50.60, 18.63, 13.18. HR-MS calc for M+H: 315.1821, obs: 315.1813.

Example 4

(5a,8a-trans)-7-benzyl-4,5a,6,7,8,8a-hexahydropyrrolo[3,4-b][1,2,3] triazolo[1,5-d][1,4]oxazine (Compound [4])

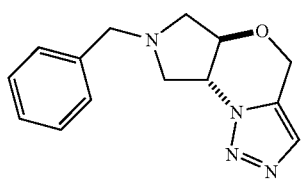

Example 4 can be prepared in the same manner as example 1 from (3,4-trans)-3-azido-1-benzyl-4-(prop-2-ynyloxy)pyrrolidine (1.44 g, 5.60 mmol) and xylene (40 ml) afforded the titled compound (1.25 g, 87% yield) as yellow solid. M.p. 101-102° C.

$^1$H NMR (400 MHz, CDCl3): δ (ppm) 7.53 (s, 1H), 7.31 (m, 5H), 5.12 (AB system, 2H), 4.32 (m, 1H), 3.91 (m, 3H), 3.71 (dd, J1=7.5 Hz, J2=9.7 Hz, 1H), 3.16 (m, 2H), 3.02 (t, J=9.7 Hz, 1H). $^{13}$C NMR (100 MHz, CDCl$_3$): δ (ppm) 138.23, 130.79, 128.72, 128.55, 128.51, 127.39, 79.29, 63.87, 60.82, 58.91, 51.84, 50.79. HR-MS calc for M+H: 257.1402, obs: 257.1401.

Example 5

(5a,8a-trans)-7-benzyl-3-methyl-4,5a,6,7,8,8a-hexahydropyrrolo[3,4-b][1,2,3]triazolo[1,5-d][1,4]oxazine (Compound [5])

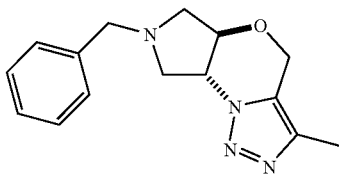

Example 5 can be prepared in the same manner as example 1 from (3,4-trans)-3-azido-4-(but-2-ynyloxy)-1-(4-methoxybenzyl)pyrrolidine (150 mg, 0.50 mmol) and toluene (6 ml) afforded the titled compound (136 mg, 93% yield) as yellow solid. M.p. 103-104° C.

$^1$H NMR (400 MHz, CDCl3): δ (ppm) 7.32 (m, 5H), 5.01 (AB system, 2H), 4.26 (m, 1H), 3.90 (m, 3H), 3.67 (dd, J1=7.1 Hz, J2=9.4 Hz, 1H), 3.14 (m, 2H), 2.99 (t, J=9.7 Hz, 1H), 2.25 (s, 3H). $^{13}$C NMR (100 MHz, CDCl$_3$): δ (ppm) 138.25, 137.57, 128.56, 128.49, 127.36, 127.24, 79.17, 63.76, 60.85, 58.97, 51.84, 50.76, 10.16. HR-MS calc for M+H: 293.1378, obs: 293.1372.

Example 6

(5a,8a-trans)-7-benzyl-3-(4-(trifluoromethyl)phenyl)-4,5a,6,7,8,8a-hexa hydropyrrolo[3,4-b][1,2,3]triazolo[1,5-d][1,4]oxazine (Compound [6])

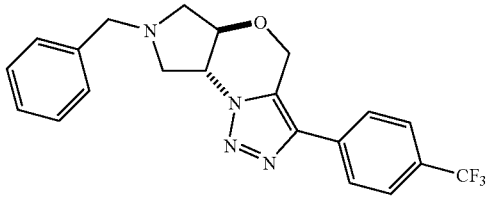

Example 6 can be prepared in the same manner as example 1 from (3,4-trans)-3-azido-1-benzyl-4-(3-(4-(trifluoromethyl)phenyl)prop-2-ynyloxy)pyrrolidine (87 mg, 0.21 mmol) and toluene (5 ml) afforded the titled compound (75 mg, 86% yield) as light brown solid. M.p. 137-138° C.

$^1$H NMR (400 MHz, CDCl3): δ (ppm) 7.75 (AB system, 4H), 7.36 (m, 5H), 5.32 (AB system, 2H), 4.41 (m, 1H), 4.05 (m, 1H), 3.95 (AB system, 2H), 3.75 (dd, J1=7.1 Hz, J2=9.4 Hz, 1H), 3.22 (m, 2H), 3.06 (t, J=9.4 Hz, 1H). $^{13}$C NMR (100 MHz, CDCl$_3$): δ (ppm) 140.50, 138.15, 134.22, 129.80 (q, $J_{CF}$=33 Hz), 128.56, 128.06, 127.45, 126.16, 125.90 (q, $J_{CF}$=4 Hz), 123.90 (q, $J_{CF}$=271 Hz), 79.05, 64.81, 60.81, 59.20, 51.80, 50.75. HR-MS calc for M+H: 401.1589, obs: 401.1580.

Example 7

(5a,8a-trans)-7-benzyl-3-(2-fluorophenyl)-4,5a,6,7,8, 8a-hexahydro pyrrolo[3,4-b][1,2,3]triazolo[1,5-d][1, 4]oxazine (Compound [7])

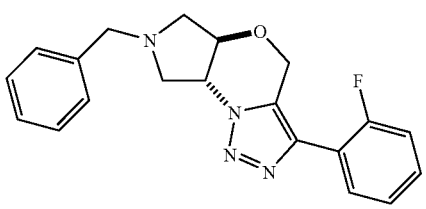

Example 7 can be prepared in the same manner as example 1 from (3,4-trans)-3-azido-1-benzyl-4-(3-(2-fluorophenyl) prop-2-ynyloxy)pyrrolidine (110 mg, 0.31 mmol) and toluene (5 ml) afforded the titled compound (73 mg, 66% yield) as light brown solid. M.p. 146-147° C.

$^1$H NMR (400 MHz, CDCl3): δ (ppm) 7.98 (m, 1H), 7.36 (m, 5H), 7.28 (m, 2H), 7.14 (m, 1H), 5.21 (m, 2H), 4.39 (m, 1H), 4.05 (m, 1H), 3.95 (AB system, 2H), 3.75 (dd, J1=7.3 Hz, J2=9.8 Hz, 1H), 3.21 (m, 2H), 3.05 (t, J=9.8 Hz, 1H). $^{13}$C NMR (100 MHz, CDCl$_3$): δ (ppm) 158.90 (d, $J_{CF}$=247 Hz), 138.26, 136.87, 130.20 (d, $J_{CF}$=5 Hz), 130.10 (d, $J_{CF}$=10 Hz), 128.77, 128.59, 128.53, 124.77, 118.40 (d, $J_{CF}$=15 Hz), 115.70 (d, $J_{CF}$=23 Hz), 79.01, 65.10, 60.87, 59.23, 51.89, 50.84. HR-MS calc for M+H: 351.1621, obs: 351.1631.

Example 8

(5a,8a-trans)-7-benzyl-3-ethyl-4,5a,6,7,8,8a-hexahydropyrrolo[3,4-b][1,2,3]triazolo[1,5-d][1,4]oxazine (Compound [8])

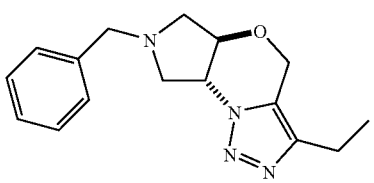

Example 8 can be prepared in the same manner as example 1 from (3,4-trans)-3-azido-1-benzyl-4-(pent-2-ynyloxy)pyrrolidine (130 mg, 0.31 mmol) and xylene (5 ml) afforded the titled compound (103 mg, 79% yield) as light brown solid. M.p. 106-107° C.

$^1$H NMR (400 MHz, CDCl3): δ (ppm) 7.34 (m, 5H), 5.10 (AB system, 2H), 4.29 (m, 1H), 3.90 (m, 3H), 3.69 (m, 1H), 3.16 (m, 2H), 3.02 (t, J=9.5 Hz, 1H), 2.67 (q, J=7.6 Hz, 2H), 1.26 (t, J=7.6 Hz, 3H). $^{13}$C NMR (100 MHz, CDCl$_3$): δ (ppm) 143.37, 138.19, 128.58, 128.50, 127.39, 126.70, 79.14, 63.89, 60.86, 58.96, 51.87, 50.81, 18.64, 13.19. HR-MS calc for M+H: 285.1715, obs: 285.1714.

Example 9

(5a,8a-trans)-7-benzyl-3-(4-chlorophenyl)-4,5a,6,7, 8,8a-hexahydro pyrrolo[3,4-b][1,2,3]triazolo[1,5-d] [1,4]oxazine (Compound [9])

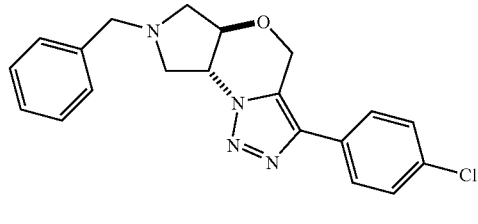

Example 9 can be prepared in the same manner as example 1 from (3,4-trans)-3-azido-1-benzyl-4-(3-(4-chlorophenyl) prop-2-ynyloxy)pyrrolidine (115 mg, 0.31 mmol) and xylene (5 ml) afforded the titled compound (89 mg, 77% yield) as white solid. M.p. 197-198° C.

$^1$H NMR (400 MHz, CDCl3): δ (ppm) 7.60 (d, J=7.9 Hz, 2H), 7.44 (d, J=7.9 Hz, 2H), 7.34 (m, 5H), 5.28 (AB system, 2H), 4.39 (m, 1H), 3.98 (m, 3H), 3.75 (m, 1H), 3.24 (m, 2H), 3.06 (t, J=9.3 Hz, 1H). $^{13}$C NMR (100 MHz, CDCl$_3$): δ (ppm) 140.81, 138.05, 133.87, 129.25, 129.20, 128.60, 128.56, 127.49, 127.28, 127.22, 78.97, 64.83, 60.82, 59.13, 51.83, 50.77. HR-MS calc for M+H: 367.1326, obs: 367.1333.

Example 10

(5a,8a-trans)-7-benzyl-3-(3-fluorophenyl)-4,5a,6,7,8, 8a-hexahydro pyrrolo[3,4-b][1,2,3]triazolo[1,5-d][1, 4]oxazine (Compound [10])

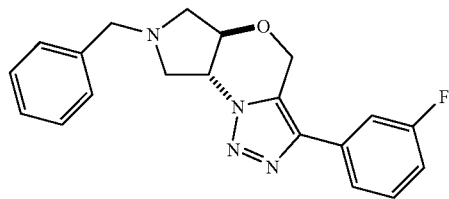

Example 10 can be prepared in the same manner as example 1 from (3,4-trans)-3-azido-1-benzyl-4-(3-(3-fluorophenyl)prop-2-ynyloxy)pyrrolidine (110 mg, 0.31 mmol) and xylene (5 ml) afforded the titled compound (93 mg, 85% yield) as light brown solid. M.p. 121-122° C.

$^1$H NMR (400 MHz, CDCl3): δ (ppm) 7.41 (m, 2H), 7.36 (m, 5H), 7.31 (m, 1H), 7.05 (m, 1H), 5.28 (AB system, 2H), 4.37 (m, 1H), 4.01 (m, 1H), 3.94 (AB system, 2H), 3.72 (m, 1H), 3.24 (m, 2H), 3.05 (t, J=9.7 Hz, 1H). $^{13}$C NMR (100 MHz, CDCl$_3$): δ (ppm) 163.16 (d, $J_{CF}$=246 Hz), 140.70, 132.90 (d, $J_{CF}$=9 Hz), 130.60 (d, $J_{CF}$=9 Hz), 128.57, 128.55, 127.57, 127.44, 121.57 (d, $J_{CF}$=3 Hz), 114.86 (d, $J_{CF}$=22 Hz), 113.00 (d, $J_{CF}$=22 Hz), 78.97, 64.80, 60.82, 59.14, 51.84, 50.77. HR-MS calc for M+H: 351.1621, obs: 351.1621.

The pure enantiomers were obtained by HPLC purification: Chiralcel OD-H, 4.6 mm×250 mm, isocratic n-hexane: 2-propanol (80:20), 0.7 ml/min, 254 nm.

Example 10a (5aR,8aR)-7-benzyl-3-(3-fluorophenyl)-4,5a,6,7,8,8a-hexahydro pyrrolo[3,4-b][1,2,3]triazolo[1,5-d][1,4]oxazine: retention time: 35.8 min.

Example 10b (5aS,8aS)-7-benzyl-3-(3-fluorophenyl)-4,5a,6,7,8,8a-hexahydro pyrrolo[3,4-b][1,2,3]triazolo[1,5-d][1,4]oxazine: retention time: 46.9 min.

Example 11

(5a,8a-trans)-7-benzyl-3-phenyl-4,5a,6,7,8,8a-hexahydropyrrolo[3,4-b][1,2,3]triazolo[1,5-d][1,4]oxazine (Compound [11])

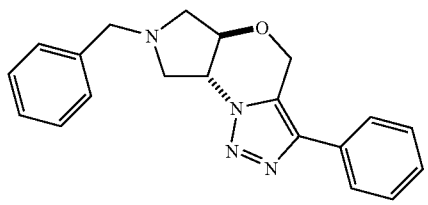

Example 11 can be prepared in the same manner as example 1 from (3,4-trans)-3-azido-1-benzyl-4-(3-phenyl-prop-2-ynyloxy)pyrrolidine (170 mg, 0.51 mmol) and xylene (7 ml) afforded the titled compound (144 mg, 85% yield) as light brown solid. M.p. 154-155° C.

$^1$H NMR (400 MHz, CDCl3): δ (ppm) 7.65 (d, J=8.4 Hz, 2H), 7.46 (t, J=7.4 Hz, 2H), 7.31 (m, 6H), 5.29 (AB system, 2H), 4.35 (m, 1H), 4.04 (m, 1H), 3.94 (AB system, 2H), 3.74 (dd, J1=7.0 Hz, J2=9.6 Hz, 1H), 3.22 (m, 2H), 3.05 (t, J=9.6 Hz, 1H). $^{13}$C NMR (100 MHz, CDCl$_3$): δ (ppm) 141.79, 138.17, 130.76, 128.98, 128.60, 128.54, 128.02, 127.44, 127.12, 126.09, 78.97, 64.95, 60.85, 59.12, 51.88, 50.82. HR-MS calc for M+H: 333.1715, obs: 333.1704.

General Procedure for the Synthesis of Compounds of General Formula (Ib)

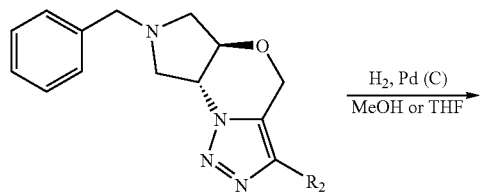

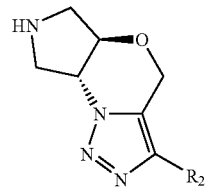

A solution of the corresponding N-benzyl compound in methanol or THF was purged with argon, and Pd/C 10% was added. The mixture was purged again with argon and after that with hydrogen. The mixture was stirred at room temperature under hydrogen atmosphere for 48 hours or until TLC analysis shows completed reaction. The suspension was purged with argon, filtered over celite and washed with dichloromethane. The filtrate was concentrated to dryness to give the product.

Example 12

(5a,8a-trans)-4,5a,6,7,8,8a-hexahydropyrrolo[3,4-b][1,2,3]triazolo[1,5-d][1,4]oxazine (Compound [12])

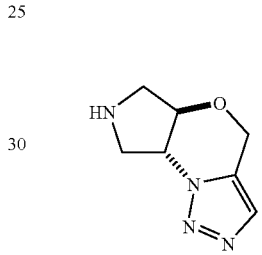

From (5a,8a-trans)-3-ethyl-7-(4-methoxybenzyl)-4,5a,6,7,8,8a-hexahydro pyrrolo[3,4-b][1,2,3]triazolo[1,5-d][1,4]oxazine (1.08 g, 4.24 mmol), Pd/C 10% (220 mg) and methanol (20 ml) afforded the titled compound (0.68 g, 97% yield) as white solid. M.p. 217° C. dec.

$^1$H NMR (400 MHz, CDCl3): δ (ppm) 7.53 (s, 1H), 5.14 (AB system, 2H), 4.24 (m, 1H), 3.92 (m, 2H), 3.37 (dd, J1=7.2 Hz, J2=9.5 Hz, 1H), 3.23 (t, J=10.4 Hz, 1H), 3.07 (t, J=10.1 Hz, 1H), 2.00 (bs, 1H). $^{13}$C NMR (100 MHz, CDCl$_3$): δ (ppm) 130.82, 128.68, 80.60, 64.04, 59.72, 45.16, 44.41. HR-MS calc for M+H: 167.0933, obs: 167.0936.

Example 13

(5a,8a-trans)-3-phenyl-4,5a,6,7,8,8a-hexahydropyrrolo[3,4-b][1,2,3] triazolo[1,5-d][1,4]oxazine (Compound [13])

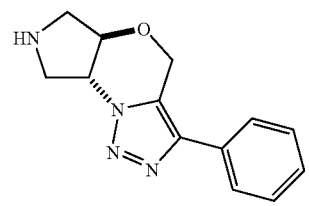

Example 13 can be prepared in the same manner as example 12 from (5a,8a-trans)-7-benzyl-3-(3-fluorophenyl)-4,5a,6,7,8,8a-hexahydropyrrolo[3,4-b][1,2,3]triazolo[1,5-d]

[1,4]oxazine (1.37 g, 4.12 mmol), Pd/C 10% (300 mg) and THF (50 ml) afforded the titled compound (0.90 g, 90% yield) as white solid. M.p. 165-167° C.

$^1$H NMR (400 MHz, CDCl3): δ (ppm) 7.68 (m, 2H), 7.48 (m, 2H), 7.37 (m, 1H), 5.36 (AB system, 2H), 4.34 (m, 1H), 4.06 (m, 1H), 3.96 (dd, J1=7.2 Hz, J2=10.2 Hz, 1H), 3.44 (dd, J1=7.0 Hz, J2=9.5 Hz, 1H), 3.31 (t, J=10.3 Hz, 1H), 3.14 (t, J=10.0 Hz, 1H), 1.82 (bs, 1H). $^{13}$C NMR (100 MHz, CDCl$_3$): δ (ppm) 141.81, 130.74, 128.98, 128.05, 127.12, 126.11, 80.36, 65.12, 60.01, 45.24, 44.53. HR-MS calc for M+Na: 265.1065, obs: 265.1074.

General Procedure for the Synthesis of Compounds of General Formula (Ic)

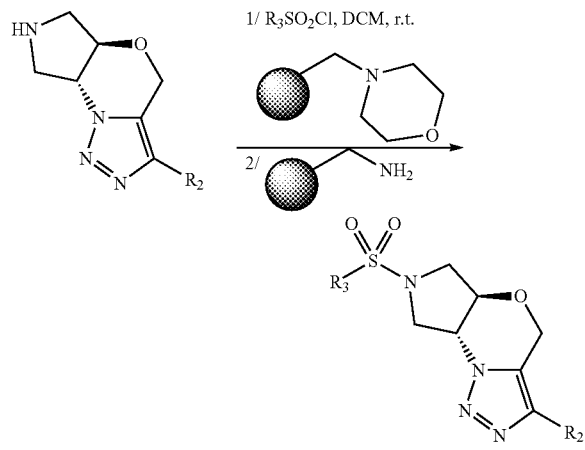

A 10 ml vial was charged with morpholinomethyl polystyrene (1.35 mmol) and anhydrous dichloromethane (2 ml) was added. After shaking the mixture for 15 minutes to swell the resin, a solution of amine 6a-b (0.3 mmol) in dichloromethane (1 ml) and the corresponding sulfonyl chloride (0.45 mmol) were added. The mixture was shaken for 3 hours or until TLC analysis shows complete reaction. Aminomethylated polystyrene (0.36 mmol) was added and the reaction mixture was shaken for 16 hours. The resin was filtered and the filtrated was concentrated to dryness to give the product.

Example 14

(5a,8a-trans)-7-(methylsulfonyl)-4,5a,6,7,8,8a-hexahydropyrrolo[3,4-b][1,2,3]triazolo[1,5-d][1,4]oxazine (Compound [14])

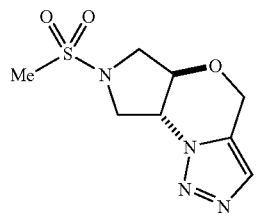

From (5a,8a-trans)-4,5a,6,7,8,8a-hexahydropyrrolo[3,4-b][1,2,3]triazolo[1,5-d][1,4]oxazine (50 mg, 0.30 mmol), morpholinomethylPS (320 mg, 1.35 mmol), methylsulfonyl chloride (52 mg, 0.45 mmol) and aminomethylatedPS (132 mg, 0.35 mmol), afforded the titled compound (52 mg, 71%). M.p. 204-206° C.

$^1$H NMR (400 MHz, CDCl3): δ (ppm) 7.60 (s, 1H), 5.21 (AB system, 2H), 4.45 (m, 1H), 4.36 (m, 1H), 4.02 (m, 1H), 3.96 (m, 1H), 3.64 (t, J=9.8 Hz, 1H), 3.46 (t, J=9.2 Hz, 1H), 2.97 (s, 3H). HR-MS calc for M+Na: 267.0528, obs: 267.0527.

Example 15

(5a,8a-trans)-7-(4-bromophenylsulfonyl)-4,5a,6,7,8,8a-hexahydro pyrrolo[3,4-b][1,2,3]triazolo[1,5-d][1,4]oxazine (Compound [15])

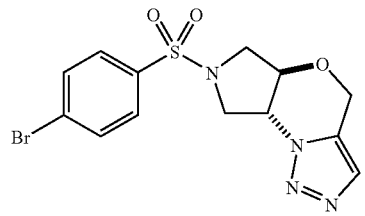

Example 15 can be prepared in the same manner as example 14 from (5a,8a-trans)-4,5a,6,7,8,8a-hexahydropyrrolo[3,4-b][1,2,3]triazolo[1,5-d][1,4] oxazine (50 mg, 0.30 mmol), morpholinomethylPS (320 mg, 1.35 mmol), 4-bromobenzenesulfonyl chloride (115 mg, 0.45 mmol) and aminomethylatedPS (330 mg, 0.36 mmol), afforded the titled compound (104 mg, 90%). M.p. 220-221° C.

$^1$H NMR (400 MHz, CDCl3): δ (ppm) 7.76 (AB system, 4H), 7.55 (s, 1H), 5.13 (AB system, 2H), 4.41 (dd, J1=7.1 Hz, J2=9.8 Hz, 1H), 4.10 (m, 1H), 3.90 (m, 1H), 3.80 (m, 1H), 3.52 (t, J=10.2 Hz, 1H), 3.36 (t, J=9.6 Hz, 1H). $^{13}$C NMR (100 MHz, CDCl$_3$): δ (ppm) 135.86, 132.90, 130.31, 128.95, 128.75, 128.60, 77.77, 63.90, 57.61, 47.31, 46.58. HR-MS calc for M+Na: 406.9789, obs: 406.9781.

Example 16

(5a,8a-trans)-7-(phenylsulfonyl)-4,5a,6,7,8,8a-hexahydropyrrolo[3,4-b][1,2,3]triazolo[1,5-d][1,4]oxazine (Compound [16])

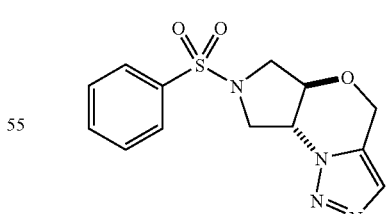

Example 16 can be prepared in the same manner as example 14 from (5a,8a-trans)-4,5a,6,7,8,8a-hexahydropyrrolo[3,4-b][1,2,3]triazolo[1,5-d][1,4] oxazine (40 mg, 0.24 mmol), morpholinomethylPS (270 mg, 0.94 mmol), benzenesulfonyl chloride (63 mg, 0.36 mmol) and aminomethylatedPS (230 mg, 0.25 mmol), afforded the titled compound (55 mg, 75%). M.p. 168-170° C.

$^1$H NMR (400 MHz, CDCl3): δ (ppm) 7.90 (m, 2H), 7.67 (m, 1H), 7.60 (m, 2H), 7.53 (s, 1H), 5.11 (AB system, 2H), 4.41 (dd, J1=7.3 Hz, J2=9.8 Hz, 1H), 4.05 (m, 1H), 3.92 (dd, J1=7.3 Hz, J2=9.1 Hz, 1H), 3.78 (m, 1H), 3.52 (t, J=10.1 Hz, 1H), 3.36 (t, J=9.7 Hz, 1H). $^{13}$C NMR (100 MHz, CDCl$_3$): δ (ppm) 136.70, 133.44, 130.35, 129.60, 128.93, 127.30, 77.49, 63.88, 57.61, 47.29, 46.54. HR-MS calc for M+Na: 329.0684, obs: 329.0692.

Example 17

(5a,8a-trans)-7-(2-fluorophenylsulfonyl)-4,5a,6,7,8,8a-hexahydro pyrrolo[3,4-b][1,2,3]triazolo[1,5-d][1,4]oxazine (Compound [17])

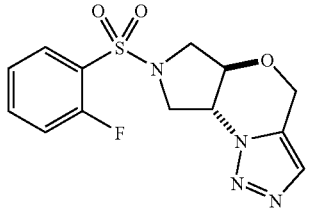

Example 17 can be prepared in the same manner as example 14 from (5a,8a-trans)-4,5a,6,7,8,8a-hexahydropyrrolo[3,4-b][1,2,3]triazolo[1,5-d][1,4] oxazine (35 mg, 0.21 mmol), morpholinomethylPS (225 mg, 0.94 mmol), 2-fluorobenzenesulfonyl chloride (58 mg, 0.31 mmol) and aminomethylatedPS (230 mg, 0.25 mmol), afforded the titled compound (55 mg, 81%). M.p. 178-180° C.

$^1$H NMR (400 MHz, CDCl3): δ (ppm) 7.95 (m, 1H), 7.62 (m, 1H), 7.56 (s, 1H), 7.34 (m, 1H), 7.26 (m, 1H), 5.16 (AB system, 2H), 4.50 (dd, J1=7.2 Hz, J2=9.5 Hz, 1H), 4.27 (m, 1H), 4.02 (m, 1H), 3.95 (m, 1H), 3.59 (t, J=10.0 Hz, 1H), 3.45 (t, J=9.4 Hz, 1H). $^{13}$C NMR (100 MHz, CDCl$_3$): δ (ppm) 158.70 (d, J$_{CF}$=250 Hz), 135.60 (d, J$_{CF}$=9 Hz), 131.41, 130.46, 128.94, 125.85 (d, J$_{CF}$=10 Hz), 124.83 (d, J$_{CF}$=4 Hz), 117.38 (d, J$_{CF}$=25 Hz), 77.57, 63.93, 57.81, 47.04, 46.27. HR-MS calc for M+Na: 347.0590, obs: 347.0590.

Example 18

(5a,8a-trans)-7-(4-fluorophenylsulfonyl)-4,5a,6,7,8,8a-hexahydro pyrrolo[3,4-b][1,2,3]triazolo[1,5-d][1,4]oxazine (Compound [18])

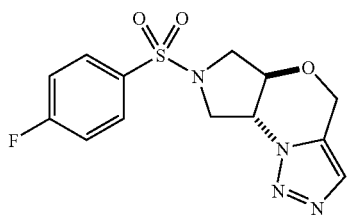

Example 18 can be prepared in the same manner as example 14 from (5a,8a-trans)-4,5a,6,7,8,8a-hexahydropyrrolo[3,4-b][1,2,3]triazolo[1,5-d][1,4] oxazine (35 mg, 0.21 mmol), morpholinomethylPS (225 mg, 0.94 mmol), 4-fluorobenzenesulfonyl chloride (58 mg, 0.31 mmol) and aminomethylatedPS (230 mg, 0.25 mmol), afforded the titled compound (47 mg, 69%). M.p. 208-209° C.

$^1$H NMR (400 MHz, CDCl3): δ (ppm) 7.92 (m, 2H), 7.53 (s, 1H), 7.28 (m, 2H), 5.12 (AB system, 2H), 4.40 (dd, J1=7.3 Hz, J2=9.7 Hz, 1H), 4.08 (m, 1H), 3.90 (m, 1H), 3.79 (m, 1H), 3.51 (t, J=10.2 Hz, 1H), 3.35 (t, J=9.4 Hz, 1H). $^{13}$C NMR (100 MHz, CDCl$_3$): δ (ppm) 165.50 (d, J$_{CF}$=255 Hz), 132.94 (d, J$_{CF}$=3 Hz), 130.35, 130.00 (d, J$_{CF}$=10 Hz), 128.95, 116.90 (d, J$_{CF}$=23 Hz), 77.20, 63.90, 57.60, 47.28, 46.53. HR-MS calc for M+Na: 347.0590, obs: 347.0587.

Example 19

(5a,8a)-7-(methylsulfonyl)-3-phenyl-4,5a,6,7,8,8a-hexahydropyrrolo[3,4-b][1,2,3]triazolo[1,5-d][1,4]oxazine (Compound [19])

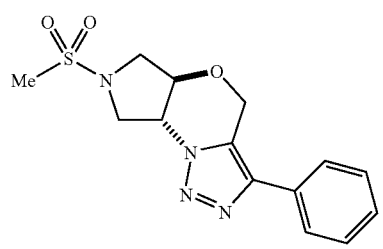

Example 19 can be prepared in the same manner as example 14 from (5a,8a-trans)-3-phenyl-4,5a,6,7,8,8a-hexahydropyrrolo[3,4-b][1,2,3] triazolo[1,5-d][1,4]oxazine (100 mg, 0.41 mmol), morpholinomethylPS (442 mg, 1.85 mmol), methylsulfonyl chloride (72 mg, 0.62 mmol) and aminomethylatedPS (183 mg, 0.49 mmol), afforded the titled compound (30 mg, 23%). M.p. 293-295° C.

$^1$H NMR (400 MHz, CDCl3): δ (ppm). $^{13}$C NMR (100 MHz, CDCl$_3$): δ (ppm) 7.65 (m, 2H), 7.47 (m, 2H), 7.37 (m, 1H), 5.36 (AB system, 2H), 4.46 (m, 1H), 4.40 (m, 1H), 4.07 (m, 1H), 3.96 (dd, J1=7.2 Hz, J2=9.0 Hz), 3.67 (t, J=9.5 Hz, 1H), 3.47 (t, J=10 Hz, 1H), 2.97 (s, 3H). HR-MS calc for M+Na: 343.0841, obs: 343.0849.

Example 20

(5a,8a-trans)-7-(4-fluorophenylsulfonyl)-3-phenyl-4,5a,6,7,8,8a-hexa hydropyrrolo[3,4-b][1,2,3]triazolo[1,5-d][1,4]oxazine (Compound [20])

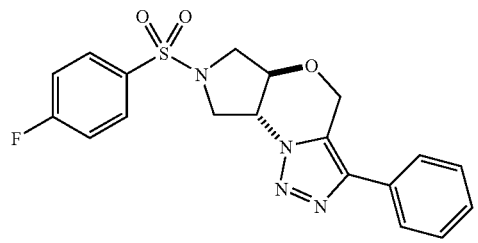

Example 20 can be prepared in the same manner as example 14 from a solution of (5a,8a-trans)-3-phenyl-4,5a,6,7,8,8a-hexahydropyrrolo[3,4-b][1,2,3] triazolo[1,5-d][1,4] oxazine (40 mg, 0.16 mmol), in DCM (4 ml) diisopropylethylamine (32 mg, 0.24 mmol) and 4-fluorobenzenesulfonyl chloride (35 mg, 0.18 mmol) were added. The reaction mixture was stirred at r.t. for 1 hour. A solid appeared which was filtered to give the titled compound (57 mg, 86%). M.p. 287-288° C.

¹H NMR (400 MHz, CDCl3): δ (ppm) 7.96 (m, 2H), 7.63 (m, 2H), 7.47 (m, 2H), 7.40 (m, 1H), 7.30 (m, 1H), 5.30 (AB system, 2H), 4.45 (dd, J1=7.2 Hz, J2=9.6 Hz, 1H), 4.16 (m, 1H), 3.95 (m, 1H), 3.85 (m, 1H), 3.57 (t, J=10.3 Hz, 1H), 3.40 (t, J=9.2 Hz, 1H). ¹³C NMR (100 MHz, CDCl₃): δ (ppm) 165.50 (d, $J_{CF}$=255 Hz), 142.27, 130.10 (d, $J_{CF}$=10 Hz), 129.06, 128.36, 126.11, 117.00 (d, $J_{CF}$=23 Hz), 77.33, 64.94, 57.85, 47.33, 46.62. HR-MS calc for M+Na: 423.0903, obs: 423.0911.

General Procedure for the Synthesis of Compounds of General Formula (Id)

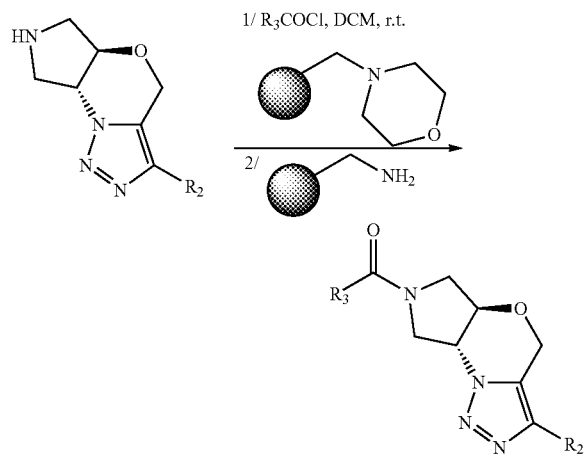

A 10 ml vial was charged with morpholinomethyl polystyrene (1.35 mmol) and anhydrous dichloromethane (2 ml) was added. After shaking the mixture for 15 minutes to swell the resin, a solution of amine (0.3 mmol) in dichloromethane (1 ml) and the corresponding acid chloride (0.45 mmol) were added. The mixture was shaken for 3 hours or until TLC analysis shows complete reaction. Aminomethylated polystyrene (0.36 mmol) was added and the reaction mixture was shaken for 16 hours. The resin was filtered and the filtrated was concentrated to dryness to give the product.

Example 21

(2-fluorophenyl)((5a,8a-trans)-5a,6,8,8a-tetrahydropyrrolo[3,4-b][1,2,3] triazolo[1,5-d][1,4]oxazin-7(4H)-yl)methanone (Compound [21])

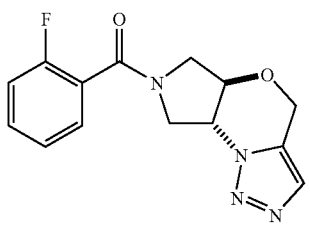

From (5a,8a-trans)-4,5a,6,7,8,8a-hexahydropyrrolo[3,4-b][1,2,3]triazolo[1,5-d][1,4] oxazine (50 mg, 0.30 mmol), morpholinomethylPS (322 mg, 1.35 mmol), 2-fluorobenzoyl chloride (71 mg, 0.45 mmol) and aminomethylatedPS (330 mg, 0.36 mmol), afforded the titled compound (85 mg, 98%). M.p. 188-190° C.

¹H NMR (400 MHz, CDCl3): mixture of two rotamers, δ (ppm) 7.56 (s, 1H), 7.48 (m, 2H), 7.27 (m, 1H), 7.15 (m, 1H), 5.20 (m, 2H), 4.79 and 4.27 (m, 1H), 4.44 and 4.37 (m, 1H), 4.25 and 3.80 (m, 1H), 4.12 and 4.04 (m, 1H), 3.76 (m, 1H), 3.64 (m, 1H). ¹³C NMR (100 MHz, CDCl₃): δ (ppm) 166.32, 166.14, 158.43 (d, $J_{CF}$=249 Hz), 158.37 (d, $J_{CF}$=249 Hz), 132.43 (d, $J_{CF}$=9 Hz), 132.27 (d, $J_{CF}$=9 Hz), 130.64, 130.42, 129.33 (d, $J_{CF}$=3 Hz), 128.98, 128.95, 124.95 (d, $J_{CF}$=3 Hz), 123.76 (d, $J_{CF}$=17 Hz), 123.35 (d, $J_{CF}$=17 Hz), 116.21 (d, $J_{CF}$=23 Hz), 116.13 (d, $J_{CF}$=23 Hz), 77.50, 64.01, 63.90, 57.75, 57.61, 47.64, 47.60, 46.76, 46.05. HR-MS calc for M+Na: 311.0920, obs: 311.0921.

Example 22 phenyl((5a,8a-trans)-5a,6,8,8a-tetrahydropyrrolo[3,4-b][1,2,3]triazolo[1,5-d][1,4]oxazin-7(4H)-yl)methanone [Compound [22]]

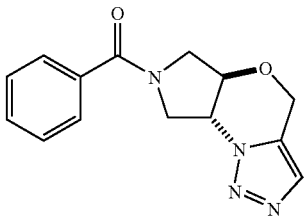

Example 22 can be prepared in the same manner as example 21 from (5a,8a-trans)-4,5a,6,7,8,8a-hexahydropyrrolo[3,4-b][1,2,3]triazolo[1,5-d][1,4] oxazine (35 mg, 0.21 mmol), morpholinomethylPS (225 mg, 0.95 mmol), benzoyl chloride (43 mg, 0.30 mmol) and aminomethylatedPS (230 mg, 0.25 mmol), afforded the titled compound (55 mg, 97%). M.p. 173-174° C.

¹H NMR (400 MHz, CDCl3): mixture of two rotamers, δ (ppm) 7.59 (s, 1H), 7.53 (m, 5H), 5.21 (m, 2H), 4.72 and 4.43 (m, 1H), 4.36 (m, 1H), 4.20 and 3.94 (m, 1H), 4.14 and 4.03 (m, 1H), 3.85 and 3.63 (m, 1H), 3.72 and 3.46 (m, 1H). ¹³C NMR (100 MHz, CDCl₃): δ (ppm) 170.71, 135.12, 134.71, 130.96, 130.85, 130.66, 130.42, 129.01, 128.69, 128.61, 127.33, 77.75, 64.00, 57.98, 48.56, 47.02, 46.27. HR-MS calc for M+Na: 293.1014, obs: 293.1015.

Example 23

(2,4-dichlorophenyl)((5a,8a-trans)-5a,6,8,8a-tetrahydropyrrolo[3,4-b][1,2,3] triazolo[1,5-d][1,4]oxazin-7(4H)-yl)methanone (Compound [23])

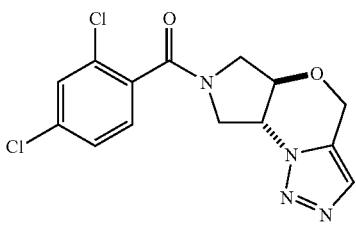

Example 23 can be prepared in the same manner as example 21 from (5a,8a-trans)-4,5a,6,7,8,8a-hexahydropyrrolo[3,4-b][1,2,3]triazolo[1,5-d][1,4] oxazine (35 mg, 0.21 mmol), morpholinomethylPS (225 mg, 0.95 mmol), 2,4-dichlorobenzoyl chloride (66 mg, 0.31 mmol) and aminomethylatedPS (230 mg, 0.25 mmol), afforded the titled compound (70 mg, 98%) as yellow oil.

$^1$H NMR (400 MHz, CDCl3): mixture of two rotamers, δ (ppm) 7.58 (m, 1H), 7.49 (m, 1H), 7.37 (m, 1H), 7.31 (m, 1H), 5.21 (m, 2H), 4.81 and 4.13 (m, 1H), 4.40 (m, 1H), 4.30 and 3.65 (m, 1H), 4.08 (m, 1H), 3.78 and 3.63 (m, 1H), 3.62 and 3.45 (m, 1H). $^{13}$C NMR (100 MHz, CDCl$_3$): δ (ppm) 166.90, 166.72, 136.58, 136.40, 134.06, 133.67, 131.02, 130.09, 130.59, 130.41, 129.97, 129.90, 129.02, 128.98, 128.73, 128.03, 127.97, 77.54, 77.35, 64.00, 63.93, 57.80, 57.49, 47.64, 46.76, 45.74, 44.77. HR-MS calc for M+Na: 361.0235, obs: 361.0241.

Example 24

3-phenyl-1-((5a,8a-trans)-5a,6,8,8a-tetrahydropyrrolo[3,4-b][1,2,3] triazolo[1,5-d][1,4]oxazin-7(4H)-yl)propan-1-one (Compound [24])

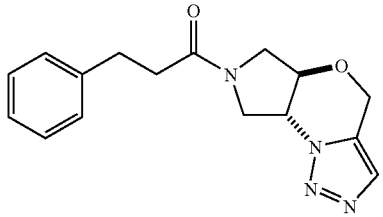

Example 24 can be prepared in the same manner as example 21 from (5a,8a-trans)-4,5a,6,7,8,8a-hexahydropyrrolo[3,4-b][1,2,3] triazolo[1,5-d][1,4]oxazine (35 mg, 0.21 mmol), morpholinomethylPS (225 mg, 0.95 mmol), 3-phenylpropionyl chloride (34 mg, 0.20 mmol) and aminomethylatedPS (230 mg, 0.25 mmol), afforded the titled compound (50 mg, 80%) as white solid. M.p. 134-135° C.

$^1$H NMR (400 MHz, CDCl3): mixture of two rotamers, δ (ppm) 7.58 (s, 1H), 7.27 (m, 5H), 5.19 (m, 2H), 4.70 and 4.32 (m, 1H), 4.25 (m, 1H), 4.16 and 3.80 (m, 1H), 3.90 (m, 1H), 3.52 (m, 1H), 3.04 (m, 2H), 2.63 (m, 2H). $^{13}$C NMR (100 MHz, CDCl$_3$): δ (ppm) 171.80, 171.67, 140.84, 140.68, 130.59, 130.40, 128.97, 128.93, 128.60, 128.46, 126.43, 126.41, 77.79, 63.89, 58.02, 57.39, 46.64, 45.71, 45.53, 44.44, 36.22, 35.78, 31.08. HR-MS calc for M+Na: 321.1327, obs: 321.1327.

Example 25

1-((5a,8a-trans)-5a,6,8,8a-tetrahydropyrrolo[3,4-b][1,2,3]triazolo[1,5-d][1,4]oxazin-7(4H)-yl)butan-1-one (Compound [25])

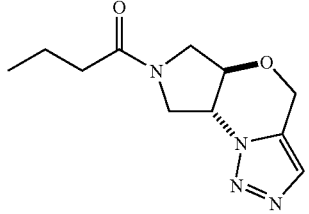

Example 25 can be prepared in the same manner as example 21 from (5a,8a-trans)-4,5a,6,7,8,8a-hexahydropyrrolo[3,4-b][1,2,3]triazolo[1,5-d][1,4] oxazine (35 mg, 0.21 mmol), morpholinomethylPS (225 mg, 0.95 mmol), butyryl chloride (21 mg, 0.20 mmol) and aminomethylatedPS (230 mg, 0.25 mmol), afforded the titled compound (37 mg, 74%) as yellow oil.

$^1$H NMR (400 MHz, CDCl3): mixture of two rotamers, δ (ppm) 7.57 and 7.56 (s, 1H), 5.19 (m, 2H), 4.68 and 4.49 (m, 1H), 4.38 and 4.28 (m, 1H), 4.15 and 3.97 (m, 1H), 4.04 and 3.94 (m, 1H), 3.71 and 3.54 (m, 1H), 3.52 and 3.39 (m, 1H), 2.27 (m, 2H), 1.69 (m, 2H), 0.98 (m, 3H). $^{13}$C NMR (100 MHz, CDCl$_3$): δ (ppm) 172.58, 172.43, 129.00, 128.94, 77.89, 77.29, 63.93, 63.91, 58.13, 57.49, 46.70, 45.77, 45.47, 44.36, 36.05, 35.78, 18.13, 18.04, 13.91. HR-MS calc for M+Na: 259.1171, obs: 259.1169.

Example 26

((5a,8a-trans)-5a,6,8,8a-tetrahydropyrrolo[3,4-b][1,2,3]triazolo[1,5-d][1,4] oxazin-7(4H)-yl)(thiophen-2-yl)methanone (Compound [26])

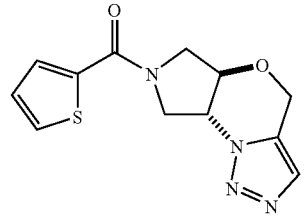

Example 26 can be prepared in the same manner as example 21 from (5a,8a-trans)-4,5a,6,7,8,8a-hexahydropyrrolo[3,4-b][1,2,3]triazolo[1,5-d][1,4] oxazine (52 mg, 0.31 mmol), morpholinomethylPS (335 mg, 1.40 mmol), 2-thiophenecarbonyl chloride (70 mg, 0.46 mmol) and aminomethylatedPS (330 mg, 0.36 mmol), afforded the titled compound (86 mg, 99%). M.p. 186-188° C.

$^1$H NMR (400 MHz, CDCl3): mixture of two rotamers, δ (ppm) 7.60 (s, 1H), 7.57 (d, J=4.8 Hz, 2H), 7.13 (t, J=4.8 Hz, 1H), 5.24 (m, 2H), 4.84 (m, 1H), 4.45 (m, 1H), 4.30 (m, 1H), 4.10 (m, 1H), 3.89 (m, 1H), 3.76 (m, 1H). $^{13}$C NMR (100 MHz, CDCl$_3$): δ (ppm) 162.99, 137.25, 130.70, 130.25, 129.06, 127.54, 77.88, 66.85, 63.98, 58.17, 57.24, 49.03, 48.18, 46.86, 45.93. HR-MS calc for M+Na: 299.0579, obs: 299.0570.

Example 27 phenyl((5a,8a-trans)-3-phenyl-5a,6,8,8a-tetrahydropyrrolo[3,4-b][1,2,3] triazolo[1,5-d][1,4]oxazin-7(4H)-yl)methanone (Compound [27])

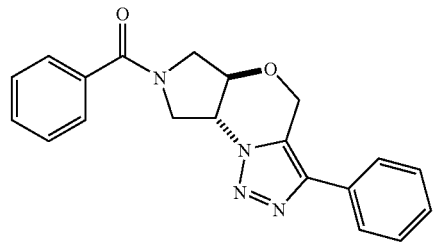

Example 27 can be prepared in the same manner as example 21 from (5a,8a-trans)-3-phenyl-4,5a,6,7,8,8a-hexahydropyrrolo[3,4-b][1,2,3] triazolo[1,5-d][1,4]oxazine (50 mg, 0.21 mmol), morpholinomethylPS (232 mg, 0.93 mmol), benzoyl chloride (43 mg, 0.36 mmol) and aminomethylatedPS (107 mg, 0.29 mmol), afforded the titled compound (68 mg, 95%) as white solid. M.p. 237-239° C.

$^1$H NMR (400 MHz, CD$_2$Cl$_2$): mixture of two rotamers, δ (ppm) 7.69 (m, 2H), 7.60 (s, 2H), 7.51 (m, 5H), 7.40 (m, 1H), 5.40 (m, 2H), 4.70 and 4.22 (m, 1H), 4.54 and 4.43 (m, 1H), 4.40 and 3.87 (m, 1H), 4.19 and 4.07 (m, 1H), 3.89 (m, 1H), 3.71 (m, 1H). $^{13}$C NMR (100 MHz, CD$_2$Cl$_2$): δ (ppm) 170.30, 141.78, 135.49, 135.16, 130.67, 130.60, 128.98, 128.57, 128.49, 128.08, 127.30, 125.98, 77.33, 77.22, 65.11, 64.98, 58.17, 57.80, 49.41, 48.44, 46.18, 45.17. HR-MS calc for M+Na: 369.1327, obs: 369.1325.

Example 28

3-phenyl-1-((5a,8a-trans)-3-phenyl-5a,6,8,8a-tetrahydropyrrolo[3,4-b][1,2,3]triazolo[1,5-d][1,4]oxazin-7(4H)-yl)propan-1-one (Compound [28])

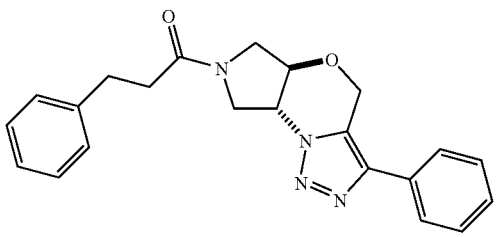

Example 28 can be prepared in the same manner as example 21 from (5a,8a-trans)-3-phenyl-4,5a,6,7,8,8a-hexahydropyrrolo[3,4-b][1,2,3] triazolo[1,5-d][1,4]oxazine (50 mg, 0.21 mmol), morpholinomethylPS (232 mg, 0.93 mmol), 3-phenylpropionyl chloride (52 mg, 0.30 mmol) and aminomethylatedPS (107 mg, 0.29 mmol), afforded the titled compound (75 mg, 97%) as white solid. M.p. 205-206° C.

$^1$H NMR (400 MHz, CD$_2$Cl$_2$): δ (ppm) 7.67 (m, 2H), 7.50 (m, 2H), 7.40 (m, 1H), 7.31 (m, 5H), 5.46 (m, 1H), 5.28 (m, 1H), 4.67 and 4.40 (m, 1H), 4.38 and 4.28 (m, 1H), 4.15 and 3.88 (m, 1H), 4.02 (m, 1H), 3.64 and 3.55 (m, 1H), 3.41 (m, 1H), 3.02 (m, 2H), 2.66 (m, 2H). $^{13}$C NMR (100 MHz, CD$_2$Cl$_2$): δ (ppm) 171.42, 171.37, 141.78, 141.72, 141.24, 141.14, 130.68, 130.61, 128.99, 128.97, 128.44, 128.06, 128.04, 127.09, 126.99, 126.18, 125.98, 125.97, 77.47, 76.88, 65.01, 64.99, 58.24, 57.58, 46.63, 45.66, 45.47, 44.32, 35.95, 35.54, 30.85, 30.81. HR-MS calc for M+Na: 397.1640, obs: 397.1639.

Example 291

1-((5a,8a-trans)-3-phenyl-5a,6,8,8a-tetrahydropyrrolo[3,4-b][1,2,3] triazolo[1,5-d][1,4]oxazin-7(4H)-yl)butan-1-one (Compound [29])

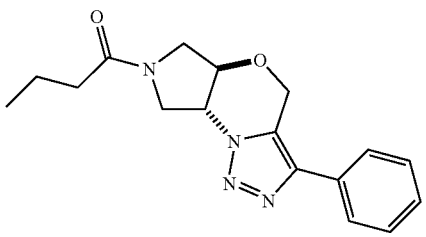

Example 29 can be prepared in the same manner as example 21 from (5a,8a-trans)-3-phenyl-4,5a,6,7,8,8a-hexahydropyrrolo[3,4-b][1,2,3] triazolo[1,5-d][1,4]oxazine (50 mg, 0.21 mmol), morpholinomethylPS (232 mg, 0.93 mmol), butyryl chloride (33 mg, 0.30 mmol) and aminomethylatedPS (107 mg, 0.29 mmol), afforded the titled compound (63 mg, 98%) as white solid. M.p. 202-204° C.

$^1$H NMR (400 MHz, CDCl$_3$): δ (ppm) 7.63 (m, 2H), 7.46 (m, 2H), 7.37 (m, 1H), 5.33 (AB system, 2H), 4.70 and 4.50 (m, 1H), 4.41 and 4.30 (m, 1H), 4.17 and 3.99 (m, 1H), 4.09 and 4.02 (m, 1H), 3.74 and 3.56 (m, 1H), 3.53 and 3.41 (m, 1H), 2.29 (m, 2H), 1.73 (m, 2H), 1.01 (m, 3H). $^{13}$C NMR (100 MHz, CDCl$_3$): δ (ppm) 172.61, 172.42, 142.06, 141.95, 130.41, 130.31, 129.07, 129.03, 128.30, 128.21, 126.90, 126.67, 126.08, 77.56, 76.96, 64.91, 58.32, 57.67, 46.72, 45.78, 45.50, 44.41, 36.08, 35.81, 18.07, 13.93. HR-MS calc for M+Na: 335.1484, obs: 335.1493.

Example 30

((5a,8a-trans)-3-phenyl-5a,6,8,8a-tetrahydropyrrolo[3,4-b][1,2,3] triazolo[1,5-d][1,4]oxazin-7(4H)-yl)(thiophen-2-yl)methanone (Compound [30])

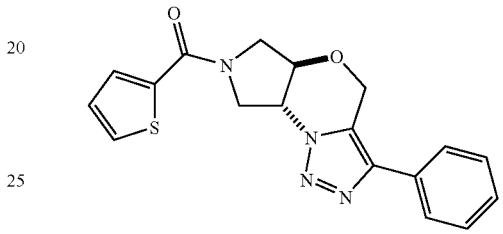

Example 30 can be prepared in the same manner as example 21 from (5a,8a-trans)-3-phenyl-4,5a,6,7,8,8a-hexahydropyrrolo[3,4-b][1,2,3] triazolo[1,5-d][1,4]oxazine (75 mg, 0.31 mmol), morpholinomethylPS (331 mg, 1.39 mmol), 2-thiophenecarbonyl chloride (69 mg, 0.46 mmol) and aminomethylatedPS (137 mg, 0.37 mmol), afforded the titled compound (64 mg, 58%). M.p. 248-249° C.

$^1$H NMR (400 MHz, CDCl$_3$): δ (ppm) 7.66 (d, J=7.1 Hz, 2H), 7.57 (m, 2H), 7.46 (t, J=7.4 Hz, 2H), 7.37 (t, J=7.1 Hz, 1H), 7.14 (t, J=4.1 Hz, 1H), 5.38 (AB system, 2H), 4.83 (m, 1H), 4.46 (m, 1H), 4.30 (m, 1H), 4.13 (m, 1H), 3.89 (m, 1H), 3.73 (m, 1H). HR-MS calc for M+Na: 375.0892, obs: 375.0901.

General Procedure for the Synthesis of Compounds of General Formula (Ie)

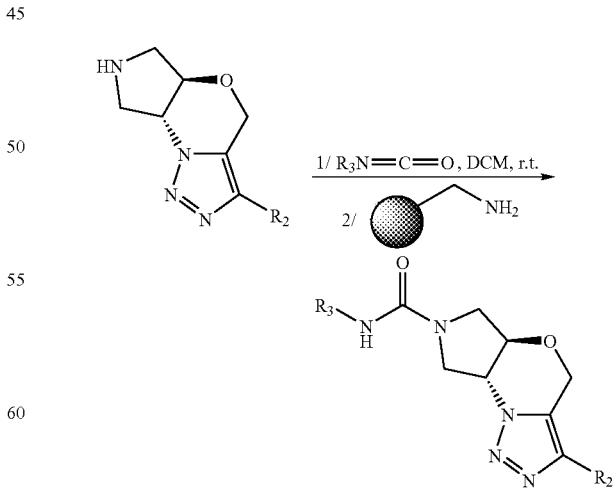

To a solution of amine (0.30 mmol) in DCM anhydrous (5 ml) the corresponding isocyanate (0.45 mmol) was added. The reaction mixture was shacked 16 hours at room temperature then aminomethyl polystyrene (0.36 mmol) was added, after 30 min, the reaction was filtered and the resin was washed several times with DCM. The solvent was evaporated to afford the product.

Example 31

(5a,8a-trans)-N-butyl-5a,6,8,8a-tetrahydropyrrolo[3,4-b][1,2,3]triazolo[1,5-d][1,4]oxazine-7(4H)-carboxamide (Compound [31])

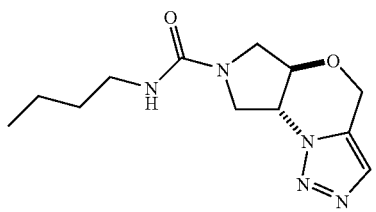

From (5a,8a-trans)-4,5a,6,7,8,8a-hexahydropyrrolo[3,4-b][1,2,3]triazolo[1,5-d][1,4] oxazine (50 mg, 0.30 mmol), butyl isocyanate (46 mg, 0.45 mmol) and aminomethylatedPS (134 mg, 0.36 mmol), afforded the titled compound (70 mg, 87%) as white solid. M.p. 194-195° C.

$^1$H NMR (400 MHz, CDCl3): δ (ppm) 7.59 (s, 1H), 5.20 (AB system, 2H), 4.41 (m, 3H), 3.99 (m, 2H), 3.59 (t, J=9.2 Hz, 1H), 3.44 (m, 1H), 3.30 (m 2H), 1.54 (m, 2H), 1.39 (m, 2H), 0.96 (t, J=7.3 Hz, 3H). $^{13}$C NMR (100 MHz, CDCl$_3$): δ (ppm) 156.51, 130.56, 128.94, 77.87, 63.90, 58.13, 45.68, 44.64, 40.58, 32.39, 20.05, 13.80. HR-MS calc for M+Na: 288.1436, obs: 288.1434.

Example 32

(5a,8a-trans)-N-phenyl-5a,6,8,8a-tetrahydropyrrolo[3,4-b][1,2,3] triazolo[1,5-d][1,4]oxazine-7(4H)-carboxamide (Compound [32])

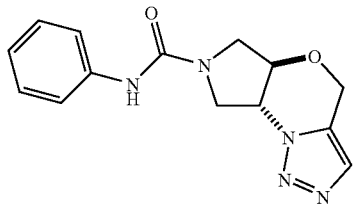

Example 32 can be prepared in the same manner as example 31 from (5a,8a-trans)-4,5a,6,7,8,8a-hexahydropyrrolo[3,4-b][1,2,3]triazolo[1,5-d][1,4]oxazine (51 mg, 0.31 mmol), phenyl isocyanate (56 mg, 0.46 mmol) and aminomethylatedPS (134 mg, 0.36 mmol), afforded the titled compound (82 mg, 93%) as white solid. M.p. 227-228° C.

$^1$H NMR (400 MHz, CDCl3): δ (ppm) 7.62 (s, 1H), 7.46 (d, J=7.8 Hz, 2H), 7.34 (t, J=7.9 Hz, 2H), 7.10 (t, J=7.3 Hz, 1H), 6.49 (s, 1H), 5.24 (AB system, 2H), 4.60 (t, J=8.3 Hz, 1H), 4.45 (m, 1H), 4.10 (m, 2H), 3.76 (t, J=9.7 Hz, 1H), 3.58 (t, J=8.7 Hz, 1H). $^{13}$C NMR (100 MHz, CDCl$_3$): δ (ppm) 153.81, 138.34, 130.07, 129.07, 129.03, 123.66, 120.01, 77.72, 63.95, 58.07, 45.93, 45.01. HR-MS calc for M+Na: 308.1123, obs: 308.1120.

Example 33

(5a,8a-trans)-N,3-diphenyl-5a,6,8,8a-tetrahydropyrrolo[3,4-b][1,2,3] triazolo[1,5-d][1,4]oxazine-7(4H)-carboxamide (Compound [33])

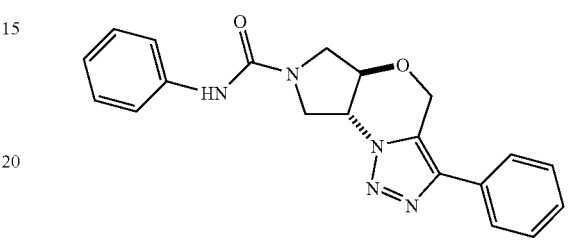

Example 33 can be prepared in the same manner as example 31 from a solution of (5a,8a-trans)-3-phenyl-4,5a,6,7,8,8a-hexahydropyrrolo[3,4-b][1,2,3] triazolo[1,5-d][1,4]oxazine (40 mg, 0.16 mmol), in DCM (4 ml) phenyl isocyanate (22 mg, 0.18 mmol) was added. The reaction mixture was stirred for 1 hour at r.t. A solid appeared which was filtered to give the titled compound (45 mg, 75%) as white solid. M.p. 275-277° C.

$^1$H NMR (400 MHz, CDCl3+1% CD$_3$OD): δ (ppm) 7.66 (t, J=7.9 Hz, 2H), 7.50 (m, 5H), 7.41 (t, J=7.2 Hz, 2H), 7.09 (t, J=7.3 Hz, 1H), 5.40 (AB system, 2H), 4.5 (m, 2H), 4.10 (m, 2H), 3.56 (t, J=9.3 Hz, 1H), 3.75 (t, J=9.3 Hz, 1H). $^{13}$C NMR (100 MHz, CDCl$_3$): δ (ppm) 154.75, 141.97, 138.86, 130.23, 129.02, 128.69, 128.28, 127.42, 126.04, 123.30, 120.43, 77.23, 64.90, 58.21, 45.86, 44.77. HR-MS calc for M+Na: 384.1436, obs: 384.1441.

General Procedure for the Synthesis of Compounds of General Formula (If)

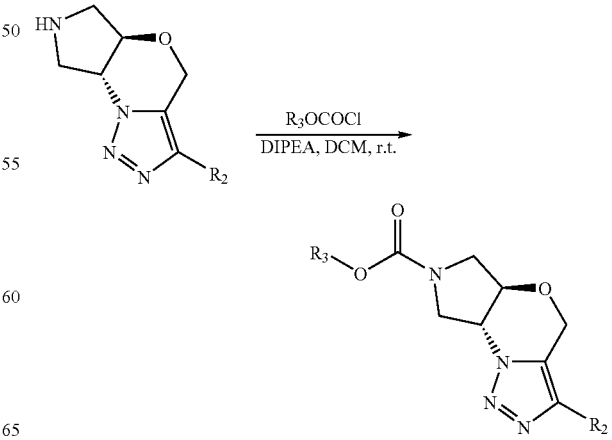

Example 34

(5a,8a-trans)-benzyl 3-phenyl-5a,6,8,8a-tetrahydropyrrolo[3,4-b][1,2,3]triazolo[1,5-d][1,4]oxazine-7(4H)-carboxylate (Compound [34])

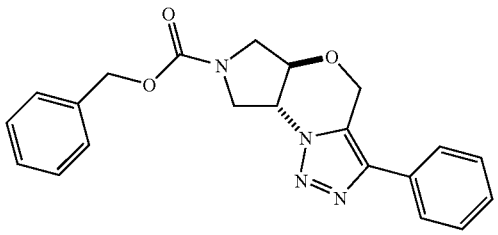

To a solution of (5a,8a-trans)-3-phenyl-4,5a,6,7,8,8a-hexahydropyrrolo[3,4-b][1,2,3] triazolo[1,5-d][1,4]oxazine (100 mg, 0.41 mmol) in DCM (5 ml), diisopropylethylamine (81 mg, 0.62 mmol) was added and the reaction mixture was stirred at room temperature for 5 minutes. Benzylchloroformate (111 mg, 0.62 mmol) was added and the reaction mixture was stirred for 3 hour at room temperature. Water was added and extracted with DCM, the organic layers were washed with water, dried over $Na_2SO_4$, filtered and concentrated under reduced pressure. The residue was recrystallized from DCM to give the titled compound (103 mg, 66%) as white solid. M.p. 209-212° C.

$^1$H NMR (400 MHz, CDCl3): δ (ppm) 7.65 (m, 2H), 7.46 (m, 2H), 7.37 (m, 6H), 5.34 (AB system, 2H), 5.20 (m, 2H), 4.56 (m, 1H), 4.37 (m, 1H), 4.03 (m, 2H), 3.65 (m, 1H), 3.47 (m, 1H). $^{13}$C NMR (100 MHz, CDCl$_3$): δ (ppm) 154.85, 142.11, 136.11, 130.45, 129.02, 128.59, 128.30, 128.24, 128.20, 128.12, 126.73, 126.15, 77.70, 67.56, 64.96, 58.31, 46.12, 45.28. HR-MS calc for M+Na: 399.1433, obs: 399.1427.

General Procedure for the Synthesis of Compounds of General Formula (I)

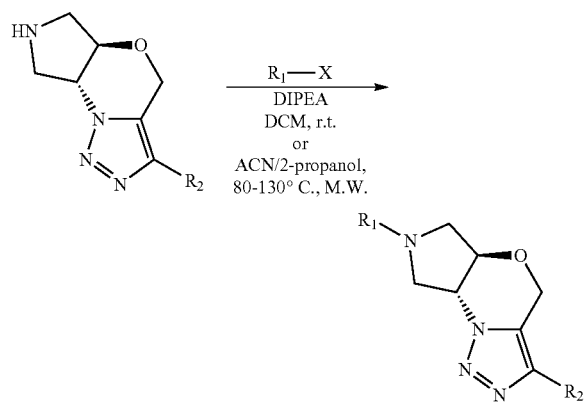

Example 35

(5a,8a-trans)-7-(pyrimidin-2-yl)-4,5a,6,7,8,8a-hexahydropyrrolo[3,4-b][1,2,3]triazolo[1,5-d][1,4]oxazine (Compound [35])

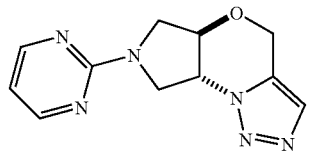

A mixture of (5a,8a-trans)-4,5a,6,7,8,8a-hexahydropyrrolo[3,4-b][1,2,3]triazolo[1,5-d][1,4]oxazine (50 mg, 0.30 mmol), 2-chloropyrimidine (43 mg, 0.36 mmol) and i-Pr$_2$EtN (78 mg, 0.60 mmol) in 2-propanol (1 ml) was heated by microwave at 130° C. for 30 minutes. The reaction mixture was cooled at room temperature and a solid appeared that was filtered to give the title compound, (44 mg, 60% yield) as light brown solid. M.p. 256-257° C.

$^1$H NMR (400 MHz, CDCl3): δ (ppm) 8.38 (d, J=4.7 Hz, 2H), 7.58 (s, 1H), 6.62 (t, J=4.7 Hz, 1H), 5.34-5.10 (AB system, 2H), 4.80 (dd, J1=7.3 Hz, J2=10.5 Hz, 1H), 4.44 (m, 1H), 4.23 (dd, J1=7.3 Hz, J2=10.1 Hz, 1H), 4.11 (m, 1H), 3.74 (t, J=10.5 Hz, 1H), 3.59 (t, J=10.1 Hz, 1H). $^{13}$C NMR (100 MHz, CDCl$_3$): δ (ppm) 160.33, 157.96, 130.67, 128.90, 110.83, 78.27, 63.95, 58.31, 46.53, 45.58. HR-MS calc for M+Na: 267.0970, obs: 267.0971.

Example 36

(5a,8a-trans)-7-ethyl-4,5a,6,7,8,8a-hexahydropyrrolo[3,4-b][1,2,3] triazolo[1,5-d][1,4]oxazine (Compound [36])

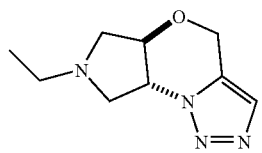

Example 36 can be prepared in the same manner as example 35 from a mixture of (5a,8a-trans)-4,5a,6,7,8,8a-hexahydropyrrolo[3,4-b][1,2,3]triazolo[1,5-d][1,4]oxazine (100 mg, 0.60 mmol), bromoethane (66 mg, 0.60 mmol) and i-Pr$_2$EtN (116 mg, 0.90 mmol) in acetonitrile (1.5 ml) was heated by microwave at 80° C. for 30 minutes. Solvent was removed and the crude was purified by flash chromatography, silica gel, gradient dichloromethane to dichloromethane:methanol 8%, to give the title compound, (50 mg, 43% yield) as light brown solid. M.p. 59-60° C.

$^1$H NMR (400 MHz, CDCl3): δ (ppm) 7.49 (s, 1H), 5.23-4.96 (AB system, 2H), 4.26 (m, 1H), 3.91 (m, 1H), 3.65 (dd, J1=7.1 Hz, J2=9.5 Hz, 1H), 3.12 (dd, J1=7.5 Hz, J2=9.1 Hz, 1H), 3.06 (t, J=9.8 Hz, 1H), 2.93 (t, J=9.5 Hz, 1H), 2.74 (m, 2H), 1.08 (t, J=7.3 Hz, 3H). $^{13}$C NMR (100 MHz, CDCl$_3$): δ (ppm) 130.79, 128.72, 79.16, 63.87, 58.79, 51.74, 51.02, 50.60, 13.41. HR-MS calc for M+Na: 217.1065, obs: 217.1059.

Example 37

(5a,8a-trans)-7-pentyl-4,5a,6,7,8,8a-hexahydropyrrolo[3,4-b][1,2,3] triazolo[1,5-d][1,4]oxazine (Compound [37])

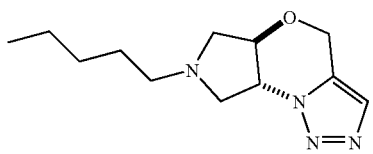

Example 37 can be prepared in the same manner as example 35 from a mixture of (5a,8a-trans)-4,5a,6,7,8,8a-hexahydropyrrolo[3,4-b][1,2,3]triazolo[1,5-d][1,4]oxazine (81 mg, 0.48 mmol), 1-bromopentane (74 mg, 0.48 mmol) and i-Pr$_2$EtN (92 mg, 0.73 mmol) in acetonitrile (1.5 ml) was heated by microwave at 80° C. for 30 minutes. Solvent was removed, the crude was suspended in ethyl acetate and washed with water and saturated solution of NaCl, dried over Na$_2$SO$_4$, filtered and concentrated. The residue was purified by flash chromatography, silica gel, gradient dichloromethane to dichloromethane:methanol 4%, to give the title compound, (54 mg, 47% yield) as yellow oil.

$^1$H NMR (400 MHz, CDCl3): δ (ppm) 7.49 (s, 1H), 5.23-4.96 (AB system, 2H), 4.26 (m, 1H), 3.91 (m, 1H), 3.63 (dd, J1=7.1 Hz, J2=9.4 Hz, 1H), 3.08 (m, 2H), 2.93 (t, J=9.8 Hz, 1H), 2.66 (m, 2H), 1.46 (m, 2H), 1.28 (m, 4H), 0.87 (t, J=7.0 Hz, 3H). $^{13}$C NMR (100 MHz, CDCl$_3$): δ (ppm) 130.69, 128.60, 79.10, 63.80, 58.80, 57.23, 52.08, 50.96, 29.17, 28.13, 22.38, 13.88. HR-MS calc for M+Na: 237.1705, obs: 237.1706.

Example 38

(5a,8a-trans)-7-(4-fluorobenzyl)-4,5a,6,7,8,8a-hexahydropyrrolo[3,4-b][1,2,3]triazolo[1,5-d][1,4]oxazine (Compound [38])

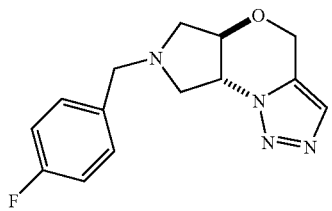

Example 38 can be prepared in the same manner as example 35 from a mixture of (5a,8a-trans)-4,5a,6,7,8,8a-hexahydropyrrolo[3,4-b][1,2,3]triazolo[1,5-d][1,4]oxazine (90 mg, 0.54 mmol), 4-Fluorobenzylchloride (63 mg, 0.43 mmol), i-Pr$_2$EtN (105 mg, 0.81 mmol) in acetonitrile (7 ml) were placed in a round bottom flask and stirred at room temperature under nitrogen for 30 min. The reaction mixture was evaporated to dryness under reduced pressure and the residue was dissolved in DCM and washed with distilled water. The aqueous phase was washed with DCM twice and the collected organic fractions were dried over Na$_2$SO$_4$ and the solvent removed under reduced pressure. The crude was purified by flash chromatography, silica gel, ethyl acetate to give the title compound (43 mg, 29% yield) as yellow oil.

$^1$H NMR (400 MHz, CDCl3): δ (ppm) 7.54 (s, 1H), 7.31 (m, 2H), 7.04 (t, J=8.6 Hz, 2H), 5.14 (AB system, 2H), 4.24 (m, 1H), 3.98 (m, 1H), 3.89 (AB system, 2H), 3.69 (dd, J1=7.2 Hz, J2=9.5 Hz, 1H), 3.15 (m, 2H), 3.00 (t, J=9.5 Hz, 1H). $^{13}$C NMR (100 MHz, CDCl$_3$): δ (ppm) 162.14 (d, J$_{CF}$=245 Hz), 134.02 (d, J$_{CF}$=3 Hz), 130.77, 130.02 (d, J$_{CF}$=8 Hz), 128.75, 115.33 (d, J$_{CF}$=21 Hz), 79.25, 63.89, 60.08, 58.88, 51.82, 50.78. HR-MS calc for M+H: 275.1308, obs: 275.1300.

Example 39

(5a,8a-trans)-7-(pyridin-2-ylmethyl)-4,5a,6,7,8,8a-hexahydropyrrolo[3,4-b][1,2,3]triazolo[1,5-d][1,4] oxazine (Compound [39])

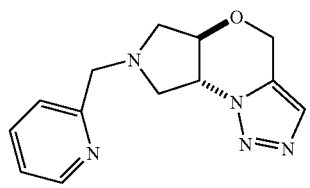

Example 39 can be prepared in the same manner as example 35 from a mixture of (5a,8a-trans)-4,5a,6,7,8,8a-hexahydropyrrolo[3,4-b][1,2,3]triazolo[1,5-d][1,4]oxazine (90 mg, 0.54 mmol), 2-picolyl chloride hydrochloride (100 mg, 0.65 mmol), i-Pr$_2$EtN (315 mg, 2.44 mmol) in acetonitrile (10 ml) were placed in a round bottom flask and stirred at room temperature under nitrogen for 30 min. The reaction mixture was evaporated to dryness under reduced pressure and the residue was dissolved in DCM and washed with distilled water. The aqueous phase was washed with DCM twice and the collected organic fractions were dried over Na$_2$SO$_4$ and the solvent removed under reduced pressure. The crude was purified by flash chromatography, silica gel, ethyl acetate to dichloromethane:methanol 2% to give the title compound (42 mg, 20% yield) as yellow oil.

$^1$H NMR (400 MHz, CDCl3): δ (ppm) 8.58 (d, J=5.0 Hz, 1H), 7.68 (td, J1=1.7 Hz, J2=7.7 Hz, 1H), 7.53 (s, 1H), 7.36 (d, J=7.7 Hz, 1H), 7.20 (dd, J1=5.0 Hz, J2=7.7 Hz, 1H), 5.14 (AB system, 2H), 4.39 (m, 1H), 4.08 (AB system, 2H), 4.03 (m, 1H), 3.79 (dd, J1=7.2 Hz, J2=9.5 Hz, 1H), 3.26 (m, 2H), 3.12 (t, J=9.5 Hz, 1H). $^{13}$C NMR (100 MHz, CDCl$_3$): δ (ppm) 158.31, 149.48, 136.65, 130.77, 128.72, 122.76, 122.33, 79.30, 63.88, 61.97, 58.94, 51.99, 50.96. HR-MS calc for M+H: 258.1355, obs: 258.1352.

Example 40

(5a,8a-trans)-3-phenyl-7-(pyrimidin-2-yl)-4,5a,6,7,8,8a-hexahydro pyrrolo[3,4-b][1,2,3]triazolo[1,5-d][1,4]oxazine (Compound [40])

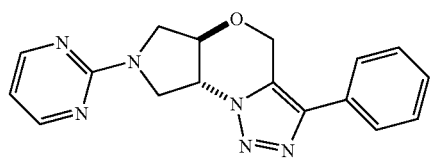

Example 40 can be prepared in the same manner as example 35 from a mixture of (5a,8a-trans)-3-phenyl-4,5a,6,7,8,8a-hexahydropyrrolo[3,4-b][1,2,3] triazolo[1,5-d][1,4]oxazine (75 mg, 0.31 mmol), 2-chloropyrimidine (41 mg, 0.34 mmol) and i-Pr$_2$EtN (60 mg, 0.46 mmol) in 2-propanol (1 ml) was heated by microwave at 130° C. for 30 minutes.

The reaction mixture was cooled at r.t. and a solid appeared that was filtered to give the title compound, (74 mg, 75% yield) as white solid. M.p. 256-257° C.

$^1$H NMR (500 MHz, CDCl3): δ (ppm) 8.38 (d, J=4.8 Hz, 2H), 7.68 (dd, J=1.0 Hz J=7.7 Hz, 2H), 7.48 (t, J=7.7 Hz, 2H), 7.37 (t, J=7.7 Hz, 1H), 6.65 (t, J=4.8 Hz, 1H), 5.40 (AB system, 2H), 4.84 (dd, J1=7.4 Hz, J2=10.5 Hz, 1H), 4.51 (m, 1H), 4.27 (dd, J1=7.3 Hz, J2=9.9 Hz, 1H), 4.18 (m, 1H), 3.79 (t, J=10.5 Hz, 1H), 3.63 (t, J=9.9 Hz, 1H). $^{13}$C NMR (125 MHz, CDCl$_3$): δ (ppm) 160.33, 157.96, 141.98, 130.57, 129.04, 128.16, 126.90, 126.12, 110.81, 77.99, 65.00, 58.54, 46.60, 45.64. HR-MS calc for M+Na: 343.1283, obs: 343.1269

Example 41

(5a,8a-trans)-7-pentyl-3-phenyl-4,5a,6,7,8,8a-hexahydropyrrolo[3,4-b][1,2,3]triazolo[1,5-d][1,4]oxazine (Compound [41])

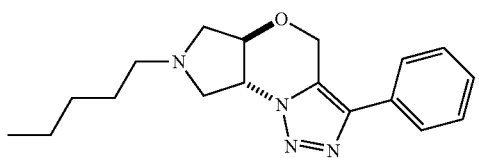

Example 41 can be prepared in the same manner as example 35 from a mixture of (5a,8a-trans)-3-phenyl-4,5a,6,7,8,8a-hexahydropyrrolo[3,4-b][1,2,3] triazolo[1,5-d][1,4]oxazine (90 mg, 0.37 mmol), 1-bromopentane (57 mg, 0.37 mmol) and i-Pr$_2$EtN (72 mg, 0.56 mmol) in acetonitrile (1.5 ml) was heated by microwave at 80° C. for 30 minutes. Solvent was removed and the crude was suspended in ethyl acetate and purified by flash chromatography, silica gel, ethyl acetate to give the title compound, (51 mg, 44% yield) as yellow solid. M.p. 105-106° C.

$^1$H NMR (500 MHz, CDCl3): δ (ppm) 7.67 (dd, J=1.2 Hz J=8.3 Hz, 2H), 7.47 (t, J=7.7 Hz, 2H), 7.36 (tt, J=1.2 Hz, J=7.7 Hz, 1H), 5.40 (AB system, 2H), 4.84 (dd, J1=7.4 Hz, J2=10.5 Hz, 1H), 5.33 (AB system, 2H), 4.37 (m, 1H), 4.02 (m, 1H), 3.72 (dd, J1=7.1 Hz, J2=9.4 Hz, 1H), 3.18 (m, 2H), 3.01 (t, J=9.4 Hz, 1H), 2.74 (m, 2H), 1.54 (m, 2H), 1.36 (m, 4H), 0.93 (t, J=7.0 Hz, 3H). $^{13}$C NMR (125 MHz, CDCl$_3$): δ (ppm) 130.69, 128.60, 79.10, 63.80, 58.80, 57.23, 52.08, 50.96, 29.17, 28.13, 22.38, 13.88. HR-MS calc for M+Na: 335.1848, obs: 335.1839

General Procedure for the Synthesis of Compounds of General Formula (Ig)

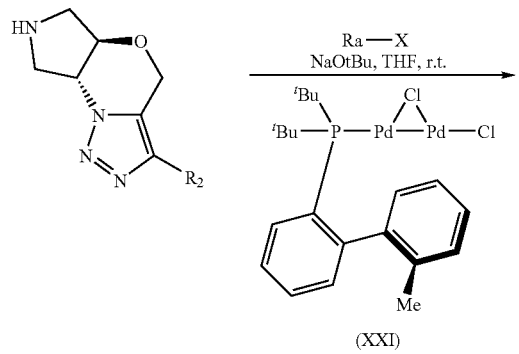

(XXI)

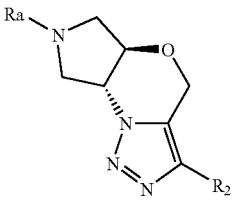

A schlenk was charged with amine 6a-b (0.62 mmol), evacuated and backfilled with argon. THF was added and the solution was degassed with argon. Then the aryl halide (0.62 mmol), NaOtBu (0.86 mmol) and the Palladium catalyst 19 (R=Me, 0.0062 mmol) were added under argon. The resulting solution was stirred at r.t. for 24 hours. The reaction mixture was concentrated under reduced pressure and the crude was purified by flash chromatography, silica gel, gradient hexane to hexante:ethyl acetate (1:4) or by precipitation with 2-propanol.

Example 42

(5a,8a-trans)-7-phenyl-4,5a,6,7,8,8a-hexahydropyrrolo[3,4-b][1,2,3] triazolo[1,5-d][1,4]oxazine (Compound [42])

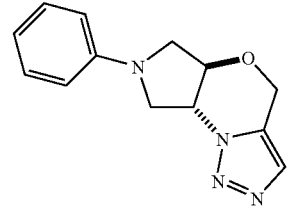

From (5a,8a-trans)-4,5a,6,7,8,8a-hexahydropyrrolo[3,4-b][1,2,3]triazolo[1,5-d][1,4] oxazine (161 mg, 0.97 mmol), bromobenzene (151 mg, 0.97 mmol), NaOtBu (130 mg, 1.35 mmol), catalyst 19 (5.8 mg, 0.0097 mmol) and THF (2 ml), afforded the titled compound (126 mg, 54%) as slightly yellow solid. M.p. 222-223° C.

$^1$H NMR (400 MHz, CDCl3): δ (ppm) 7.58 (s, 1H), 7.29 (m, 2H), 6.79 (m, 1H), 6.62 (m, 2H), 5.20 (AB system, 2H), 4.45 (m, 1H), 4.30 (t, J=8.2 Hz, 1H), 4.10 (m, 1H), 3.79 (t, J=7.8 Hz, 1H), 3.66 (t, J=9.1 Hz, 1H), 3.51 (t, J=9.1 Hz, 1H). $^{13}$C NMR (100 MHz, CDCl$_3$): δ (ppm) 146.61, 130.69, 129.49, 128.90, 117.39, 111.32, 78.41, 63.92, 58.44, 47.67, 46.52. HR-MS calc for M+Na: 265.1065, obs: 265.1069.

Example 43

(5a,8a-trans)-7-(4-chlorophenyl)-4,5a,6,7,8,8a-hexahydropyrrolo[3,4-b][1,2,3]triazolo[1,5-d][1,4]oxazine (Compound [43])

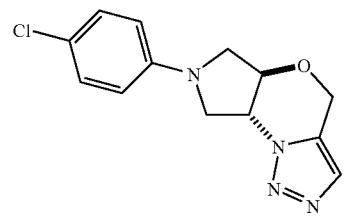

Example 43 can be prepared in the same manner as example 42 from (5a,8a-trans)-4,5a,6,7,8,8a-hexahydropyrrolo[3,4-b][1,2,3]triazolo[1,5-d][1,4] oxazine (103 mg, 0.62 mmol), 2,4-dichlorobenzene (91 mg, 0.62 mmol), NaOtBu (83 mg, 0.86 mmol), catalyst 19 (3.7 mg, 0.0062 mmol) and THF (2 ml), afforded the titled compound (106 mg, 62%) as white solid. M.p. 238° C. dec.

$^1$H NMR (400 MHz, CDCl3): δ (ppm) 7.57 (s, 1H), 7.20 (d, J=8.7 Hz, 2H), 6.50 (d, J=8.7 Hz, 2H), 5.20 (AB system, 2H), 4.43 (m, 1H), 4.25 (t, J=8.3 Hz, 1H), 4.09 (m, 1H), 3.72 (t, J=8.3 Hz, 1H), 3.62 (t, J=9.5 Hz, 1H), 3.47 (t, J=8.3 Hz, 1H). $^{13}$C NMR (100 MHz, CDCl$_3$): δ (ppm) 145.42, 130.84, 129.43, 129.11, 122.41, 112.59, 78.44, 64.15, 58.54, 47.97, 46.85. HR-MS calc for M+Na: 299.0676, obs: 299.0680.

Example 44

(5a,8a-trans)-7-(pyridin-2-yl)-4,5a,6,7,8,8a-hexahydropyrrolo[3,4-b][1,2,3]triazolo[1,5-d][1,4]oxazine (Compound [44])

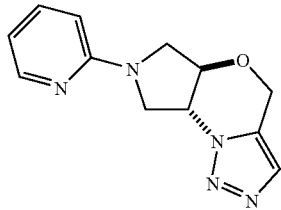

Example 44 can be prepared in the same manner as example 42 from (5a,8a-trans)-4,5a,6,7,8,8a-hexahydropyrrolo[3,4-b][1,2,3]triazolo[1,5-d][1,4] oxazine (61 mg, 0.37 mmol), 2-bromopyridine (64 mg, 0.40 mmol), NaOtBu (50 mg, 0.51 mmol), catalyst 19 (2.2 mg, 0.0037 mmol) and THF (1.5 ml), afforded the titled compound (39 mg, 43%) as white solid. M.p. 216° C. dec.

$^1$H NMR (400 MHz, CDCl3): δ (ppm) 8.18 (m, 1H), 7.56 (s, 1H), 7.51 (m, 1H), 6.65 (m, 1H), 6.43 (m, 1H), 5.20 (AB system, 2H), 4.53 (dd, J1=7.4 Hz, J2=9.3 Hz, 1H), 4.43 (m, 1H), 4.07 (m, 2H), 3.66 (t, J=9.6 Hz, 1H), 3.52 (m, 1H). $^{13}$C NMR (100 MHz, CDCl$_3$): δ (ppm) 156.82, 148.43, 137.74, 130.87, 129.05, 113.20, 106.19, 78.45, 64.09, 58.54, 46.84, 45.81. HR-MS calc for M+H: 244.1212, obs: 244.1198.

Example 45

(5a,8a-trans)-3,7-diphenyl-4,5a,6,7,8,8a-hexahydropyrrolo[3,4-b][1,2,3] triazolo[1,5-d][1,4]oxazine (Compound [45])

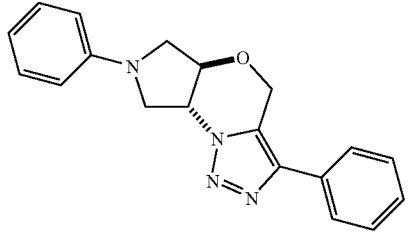

Example 45 can be prepared in the same manner as example 42 from (5a,8a-trans)-3-phenyl-4,5a,6,7,8,8a-hexahydropyrrolo[3,4-b][1,2,3]triazolo[1,5-d][1,4]oxazine (101 mg, 0.42 mmol), bromobenzene (78 mg, 0.50 mmol), NaOtBu (56 mg, 0.58 mmol), catalyst 19 (2.5 mg, 0.0042 mmol) and THF (1.5 ml), afforded the titled compound (83 mg, 62%) as white solid. M.p. 256-257° C.

$^1$H NMR (400 MHz, CDCl3): δ (ppm) 7.68 (d, J=7.7 Hz, 2H), 7.48 (t, J=7.7 Hz, 2H), 7.38 (t, J=7.3 Hz, 1H), 7.31 (t, J=7.3 Hz, 2H), 6.81 (t, J=7.3 Hz, 1H), 6.65 (t, J=8.2 Hz, 2H), 5.40 (AB system, 2H), 4.51 (m, 1H), 4.36 (t, J=7.7 Hz, 1H), 4.17 (m, 1H), 3.83 (t, J=7.7 Hz, 1H), 3.71 (t, J=9 Hz, 1H), 3.54 (t, J=8.5 Hz, 1H). $^{13}$C NMR (100 MHz, CDCl$_3$): δ (ppm) 146.88, 142.27, 130.76, 129.70, 129.25, 128.40, 127.18, 126.36, 117.59, 111.58, 78.33, 65.21, 58.93, 47.96, 46.86. HR-MS calc for M+Na: 341.1378, obs: 341.1386.

Example 46

(5a,8a-trans)-7-(4,6-dichloropyrimidin-2-y)-4,5a,6,7,8,8a-hexahydro pyrrolo[3,4-b][1,2,3]triazolo[1,5-d][1,4]oxazine (Compound [46])

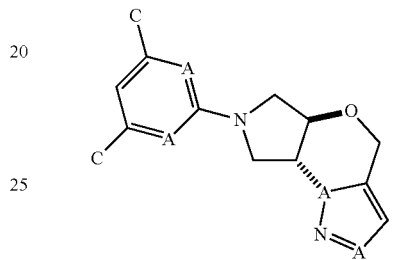

A mixture of (5a,8a-trans)-7-benzyl-4,5a,6,7,8,8a-hexahydropyrrolo[3,4-b][1,2,3] triazolo[1,5-d][1,4]oxazine (130 mg, 0.50 mmol), and 2,4,6-trichloropyrimidine (130 mg, 0.70 mmol) in 1,2-dimethoxyethane (0.2 ml) was heated by microwave at 150° C. for 30 minutes. The reaction mixture was cooled at room temperature and a solid appeared that was filtered. Purification by flash chromatography, silica gel, DCM:THF (97:3) afforded the title compound, (95 mg, 60% yield) as white solid.

$^1$H NMR (400 MHz, CDCl3): δ (ppm) 7.62 (s, 1H), 6.72 (s, 1H), 5.20 (AB system, 2H), 4.83 (dd, J1=7.4 Hz, J2=9.3 Hz, 1H), 4.45 (m, 1H), 4.27 (m, 1H), 4.11 (m, 1H), 3.78 (t, J=9.6 Hz, 1H), 3.62 (t, J=9.6 Hz, 1H). $^{13}$C NMR (100 MHz, CDCl$_3$): δ (ppm) 161.85, 159.65, 130.52, 128.96, 109.50, 77.92, 64.01, 58.02, 46.96, 46.06. HR-MS calc for M+H: 313.0371, obs: 313.0372.

Example 47

(5a,8a-trans)-7-(4,6-dichloropyrimidin-2-yl)-3-phenyl-4,5a,6,7,8,8a-hexahydro pyrrolo[3,4-b][1,2,3]triazolo[1,5-d][1,4]oxazine (Compound [47])

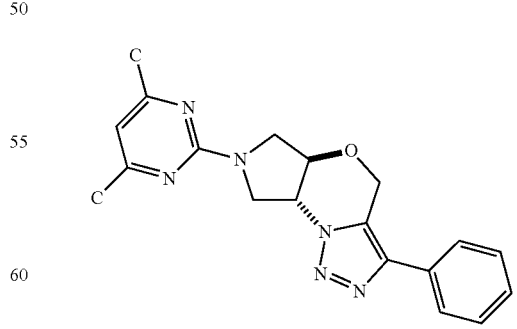

A mixture of (5a,8a-trans)-7-benzyl-3-phenyl-4,5a,6,7,8,8a-hexahydropyrrolo[3,4-b][1,2,3]triazolo[1,5-d][1,4]oxazine (300 mg, 0.90 mmol), and 2,4,6-trichloropyrimidine (231 mg, 0.70 mmol) in 1,2-dimethoxyethane (0.5 ml) was heated by microwave at 150° C. for 30 minutes. The reaction mixture was cooled at room temperature and a solid appeared that was filtered. Purification by flash chromatography, silica gel, DCM:THF (99:1) afforded the title compound, (245 mg, 70% yield) as white solid.

$^1$H NMR (400 MHz, CDCl$_3$): δ (ppm) 7.69 (m, 2H), 7.49 (m, 2H), 7.40 (m, 1H), 6.72 (s, 1H), 5.40 (AB system, 2H), 4.86 (dd, J1=7.4 Hz, J2=9.3 Hz, 1H), 4.49 (m, 1H), 4.29 (m, 1H), 4.17 (m, 1H), 3.81 (t, J=9.6 Hz, 1H), 3.64 (t, J=9.6 Hz, 1H). $^{13}$C NMR (100 MHz, CDCl$_3$): δ (ppm) 161.99, 159.65, 142.10, 130.45, 129.06, 128.25, 126.74, 126.13, 109.50, 77.63, 65.02, 58.22, 46.99, 46.11. HR-MS calc for M+H: 389.0684, obs: 389.0674.

Example 48

(5a,8a-trans)-7-(4-chloropyrimidin-2-yl)-3-phenyl-4, 5a,6,7,8,8a-hexahydro pyrrolo[3,4-b][1,2,3]triazolo [1,5-d][1,4]oxazine (Compound [48])

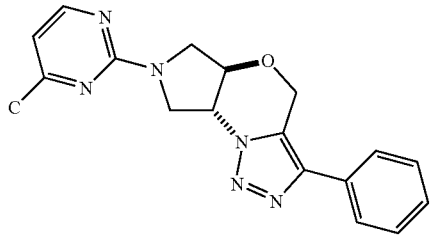

A mixture of (5a,8a-trans)-7-benzyl-3-phenyl-4,5a,6,7,8,8a-hexahydropyrrolo[3,4-b][1,2,3]triazolo[1,5-d][1,4]oxazine (309 mg, 0.92 mmol), and 2,4-dichloropyrimidine (231 mg, 0.70 mmol) in 1,2-dimethoxyethane (0.5 ml) was heated by microwave at 150° C. for 30 minutes. The reaction mixture was cooled at room temperature and a solid appeared that was filtered. Purification by flash chromatography, silica gel, DCM:THF (99:1) afforded the title compound, (210 mg, 64% yield) as white solid.

$^1$H NMR (400 MHz, CDCl$_3$): δ (ppm) 8.28 (d, J=5.0 Hz, 1H), 7.71 (m, 2H), 7.50 (m, 2H), 7.40 (m, 1H), 6.69 (s, 1H), 5.40 (AB system, 2H), 4.86 (dd, J1=7.5 Hz, J2=10.8 Hz, 1H), 4.51 (m, 1H), 4.29 (m, 1H), 4.19 (m, 1H), 3.82 (t, J=10.2 Hz, 1H), 3.64 (t, J=10.2 Hz, 1H). $^{13}$C NMR (100 MHz, CDCl$_3$): δ (ppm) 142.06, 130.52, 129.06, 128.27, 126.81, 126.14, 111.15, 78.13, 65.13, 58.36, 46.82, 45.89. HR-MS calc for M+Na: 377.0894, obs: 377.0905.

Example 49

(5a,8a-trans)-7-(4-chloropyrimidin-2-yl)-4,5a,6,7,8, 8a-hexahydro pyrrolo[3,4-b][1,2,3]triazolo[1,5-d][1, 4]oxazine (Compound [49])

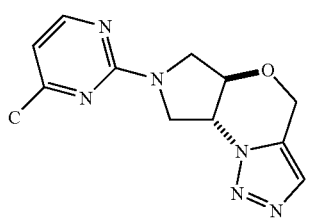

A mixture of (5a,8a-trans)-7-benzyl-4,5a,6,7,8,8a-hexahydropyrrolo[3,4-b][1,2,3]triazolo[1,5-d][1,4]oxazine (150 mg, 0.58 mmol), and 2,4-dichloropyrimidine (231 mg, 0.70 mmol) in 1,2-dimethoxyethane (0.2 ml) was heated by microwave at 150° C. for 30 minutes. The reaction mixture was cooled at room temperature and a solid appeared that was filtered. Purification by flash chromatography, silica gel, DCM:THF (97:3) afforded the title compound, (140 mg, 86% yield) as white solid.

$^1$H NMR (400 MHz, CDCl$_3$): δ (ppm) 8.26 (d, J=5.0 Hz, 1H), 7.61 (s, 1H), 6.68 (s, 1H), 5.20 (AB system, 2H), 4.82 (dd, J1=7.5 Hz, J2=10.8 Hz, 1H), 4.44 (m, 1H), 4.25 (m, 1H), 4.13 (m, 1H), 3.76 (t, J=10.2 Hz, 1H), 3.61 (t, J=10.2 Hz, 1H). $^{13}$C NMR (100 MHz, CDCl$_3$): δ (ppm) 160.27, 158.94, 130.58, 128.92, 110.42, 78.10, 63.99, 58.17, 46.78, 45.82. HR-MS calc for M+H: 279.0761, obs: 279.0760.

Example 50

2-((5a,8a-trans)-5a,6,7,8,8a-tetrahydropyrrolo[3,4-b][1,2,3]triazolo[1,5-d][1,4]oxazin-7(4H)-yl)pyrimidin-4-amine (Compound [50])

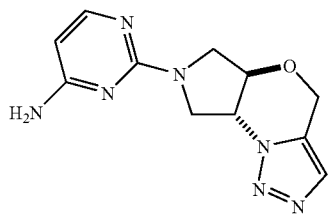

Step 1

A mixture of (5a,8a-trans)-7-(4-chloropyrimidin-2-yl)-4,5a,6,7,8,8a-hexahydro pyrrolo[3,4-b][1,2,3]triazolo[1,5-d][1,4]oxazine (185 mg, 0.66 mmol), 2,4-dimethoxybenzylamine (135 mg, 0.79 mmol) and diisopropylethylamine (0.17 ml, 0.99 mmol) in 2-propanol (4 ml) was heated by microwave at 150° C. for 60 minutes. The reaction mixture was cooled at room temperature and the solvent was removed under vacuum.

Step 2

To a solution of the product obtained in step 1 (170 mg, 0.41 mmol) in DCM (15 ml), trifluoroacetic acid (3.5 ml) was added and the mixture was stirred at rt for 6 hours. The reaction mixture was washed with KOH 1M solution, the organic phase was separated and the solvent removed under vacuum. Purification by flash chromatography, silica gel, DCM:MeOH (97:3) afforded the title compound, (30 mg, 27% yield).

$^1$H NMR (400 MHz, CDCl$_3$): δ (ppm) 7.99 (d, J=5.6 Hz, 1H), 7.60 (s, 1H), 5.87 (d, J=5.6 Hz, 1H), 5.20 (AB system, 2H), 4.77 (dd, J1=7.4 Hz, J2=10.6 Hz, 1H), 4.68 (bs, 2H), 4.41 (m, 1H), 4.20 (m, 1H), 4.08 (m, 1H), 3.67 (t, J=10.2 Hz, 1H), 3.54 (t, J=10.2 Hz, 1H). $^{13}$C NMR (100 MHz, CDCl$_3$): δ (ppm) 163.30, 160.57, 156.96, 130.66, 128.84, 95.49, 78.39, 63.93, 58.39, 46.47, 45.43. HR-MS calc for M+H: 260.1260, obs: 260.1249.

Example 51

2-((5a,8a-trans)-3-phenyl-5a,6,7,8,8a-tetrahydropyrrolo[3,4-b][1,2,3]triazolo[1,5-d][1,4]oxazin-7(4H)-yl)pyrimidin-4-amine (Compound [51])

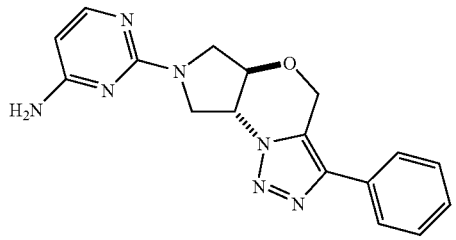

Step 1

A mixture of (5a,8a-trans)-7-(4-chloropyrimidin-2-yl)-3phenyl-4,5a,6,7,8,8a-hexahydro pyrrolo[3,4-b][1,2,3]triazolo[1,5-d][1,4]oxazine (95 mg, 0.26 mmol), 2,4-dimethoxybenzylamine (54 mg, 0.32 mmol) and diisopropylethylamine (0.070 ml, 0.40 mmol) in 2-propanol (4 ml) was heated by microwave at 150° C. for 60 minutes. The reaction mixture was cooled at room temperature and the solvent was removed under vacuum.

Step 2

To a solution of the product obtained in step 1 (83 mg, 0.17 mmol) in DCM (8 ml), trifluoroacetic acid (0.7 ml) was added and the mixture was stirred at rt for 6 hours. The reaction mixture was washed with KOH 1M solution, the organic phase was separated and the solvent removed in vacuum. Purification by flash chromatography, silica gel, ethyl acetate, afforded the title compound, (31 mg, 54% yield).

$^1$H NMR (400 MHz, CDCl$_3$): δ (ppm) 8.01 (d, J=5.6 Hz, 1H), 7.70 (m, 2H), 7.49 (m, 2H), 7.38 (m, 1H), 5.89 (d, J=5.6 Hz, 1H), 5.40 (AB system, 2H), 4.81 (dd, J1=7.4 Hz, J2=10.6 Hz, 1H), 4.69 (bs, 2H), 4.48 (m, 1H), 4.24 (m, 1H), 4.15 (m, 1H), 3.74 (t, J=10.2 Hz, 1H), 3.57 (t, J=10.2 Hz, 1H). $^{13}$C NMR (100 MHz, CDCl$_3$): δ (ppm) 160.46, 156.81, 156.48, 130.56, 129.02, 128.15, 126.95, 126.13, 78.06, 64.95, 58.56, 46.46, 45.48. HR-MS calc for M+H: 336.1573, obs: 336.1581.

Example 52

6-((5a,8a-trans)-3-phenyl-5a,6,8,8a-tetrahydropyrrolo[3,4-b][1,2,3]triazolo[1,5-d][1,4]oxazin-7(4H)-yl)-1,3,5-triazine-2,4-diamine (Compound [52])

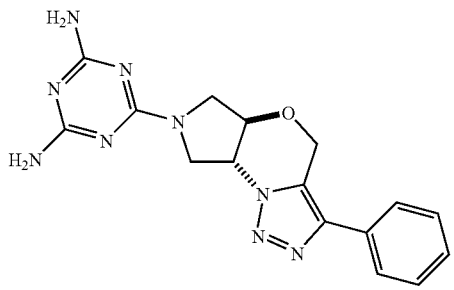

Step 1

To a solution of (5a,8a-trans)-7-benzyl-3-phenyl-4,5a,6,7,8,8a-hexahydropyrrolo[3,4-b][1,2,3]triazolo[1,5-d][1,4]oxazine (300 mg, 0.90 mmol), and LiCl (58 mg, 1.35 mmol) in THF (5 ml), a solution of cyanuric chloride (200 mg, 1.08 mmol) in THF (4 ml) was added and the mixture was stirred at rt for 1 hour. A solid of the dichlorotriazine derivative appeared that was filtered and used in the next reaction without further purification.

The solid obtained before was suspended in 2-propanol (1.5 ml), DIPEA (0.054 ml, 0.30 mmol)) and 2,4-dimethoxybenzylamine (47 mg, 0.28 mmol) were added and the mixture was heated by microwaves at 110° C. for 20 minutes. The reaction mixture was cooled at room temperature, water was added and extracted with DCM, the organic phase was washed with NaCl saturated solution, dried (Na$_2$SO$_4$), filtered and concentrated under vacuum.

Step 2

To a solution of the product obtained in step 1 (46 mg, 0.07 mmol) in DCM (1 ml), trifluoroacetic acid (2 ml) was added and the mixture was stirred at rt for 16 hours. Water was added and the mixture was stirred at rt for 30 min. The resulting solid was filtered, suspended in DCM (0.5 ml) and triethylamine (2 ml) was added. The solvent was removed under vacuum and the residue triturated with methanol and filtered to afford the title compound, (25 mg, quant. yield).

$^1$H NMR (400 MHz, DMSO-d$_6$): δ (ppm) 7.69 (m, 2H), 7.49 (m, 2H), 7.37 (m, 1H), 6.28 (bs, 4H), 5.44 (AB system, 2H), 4.61 (m, 1H), 4.50 (m, 1H), 4.28 (m, 1H), 4.00 (m, 1H), 3.53 (m, 1H), 3.35 (m, 1H). HR-MS calc for M+H: 352.1634, obs: 352.1650.

Scheme 2. Synthesis of compounds (If')

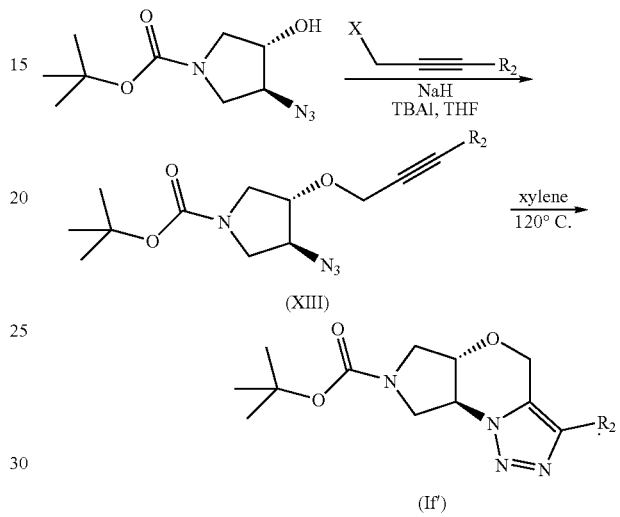

General Procedure for the Synthesis of Enantiomerically Pure (5aS,8aS)-tert-butyl-5a,6,8,8a-tetrahydropyrrolo[3,4-b][1,2,3]triazolo[1,5-d][1,4]oxazine-7(4H)-carboxylate Derivatives (Formula If')

Example 53

(5aS,8aS)-tert-butyl 5a,6,8,8a-tetrahydropyrrolo[3,4-b][1,2,3]triazolo[1,5-d][1,4]oxazine-7(4H)-carboxylate (Compound [53])

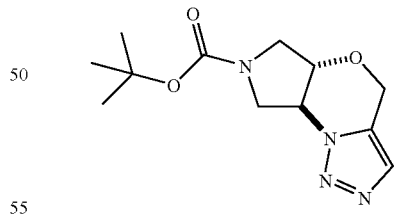

A solution of (3S,4S)-tert-butyl 3-azido-4-(prop-2-ynyloxy)pyrrolidine-1-carboxylate (77 mg, 0.29 mmol) in toluene (5 ml) was heated at 120° C. for 16 hours or until TLC analysis shows completed reaction. The solvent was removed under reduced pressure and the residue was purified by flash chromatography, silica gel, gradient hexane:ethyl acetate (3:1) to neat ethyl acetate, to afford the titled compound (74 mg, 96%) as white solid. M.p. 155-157° C.

$^1$H NMR (400 MHz, CDCl$_3$): mixture of two rotamers, δ (ppm) 7.49 (m, 1H), 5.11 (AB system, 2H), 4.37 (m, 1H), 4.25 (m, 1H), 3.90 (m, 2H), 3.46 (m, 1H), 3.31 (m, 1H), 1.43 (s, 9H). $^{13}$C NMR (100 MHz, CDCl$_3$): δ (ppm) 154.21, 130.59, 128.84, 80.63, 78.02, 77.61, 63.93, 58.19, 57.84, 46.23, 45.58, 45.29, 44.58, 28.41. HR-MS calc for M+Na: 289.1277, obs: 289.1274. [α]$^{20}_D$+64.3 (c=1, CHCl$_3$).

Example 54

(5aS,8aS)-tert-butyl 3-methyl-5a,6,8,8a-tetrahydropyrrolo[3,4-b][1,2,3]triazolo[1,5-d][1,4]oxazine-7(4H)-carboxylate (Compound [54])

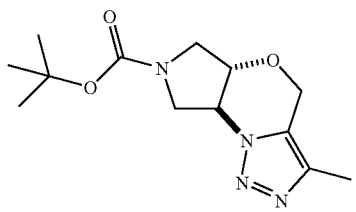

Example 54 can be prepared in the same manner as example 46 from (3S,4S)-tert-butyl 3-azido-4-(but-2-ynyloxy)pyrrolidine-1-carboxylate (115 mg, 0.41 mmol) and xylene (10 ml), afforded the titled compound (55 mg, 47%) as white solid. M.p. 195-196° C.

$^1$H NMR (400 MHz, CDCl$_3$): mixture of two rotamers, δ (ppm) 5.03 (AB system, 2H), 4.37 (m, 1H), 4.21 (m, 1H), 3.88 (m, 2H), 3.47 (m, 1H), 3.31 (m, 1H), 2.23 (s, 3H), 1.45 (s, 9H). $^{13}$C NMR (100 MHz, CDCl$_3$): δ (ppm) 154.14, 137.74, 126.92, 80.57, 80.47, 77.81, 77.46, 63.70, 58.13, 57.78, 46.16, 45.49, 45.22, 44.47, 28.28, 10.04. HR-MS calc for M+Na: 303.1433, obs: 303.1437. [α]$^{20}_D$+126.5 (c=1, CHCl$_3$).

Example 55

(5aS,8aS)-tert-butyl 3-phenyl-5a,6,8,8a-tetrahydropyrrolo[3,4-b][1,2,3]triazolo[1,5-d][1,4]oxazine-7(4H)-carboxylate (Compound [55])

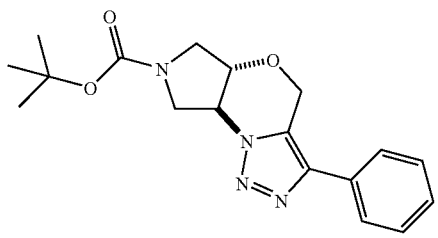

Example 55 can be prepared in the same manner as example 46 from (3S,4S)-tert-butyl 3-azido-4-(3-phenyl-prop-2-ynyloxy)pyrrolidine-1-carboxylate (120 mg, 0.35 mmol) and xylene (6 ml), afforded the titled compound (68 mg, 57%) as white solid. M.p. 236-237° C.

$^1$H NMR (400 MHz, CDCl$_3$): mixture of two rotamers, δ (ppm) 7.60 (d, J=7.3 Hz, 2H), 7.42 (t, J=7.3 Hz, 2H), 7.32 (t, J=7.3 Hz, 1H), 5.28 (AB system, 2H), 4.42 (m, 1H), 4.28 (m, 1H), 3.90 (m, 2H), 3.52 (m, 1H), 3.35 (m, 1H), 1.48 (s, 9H). $^{13}$C NMR (100 MHz, CDCl$_3$): δ (ppm) 154.24, 141.93, 130.43, 129.02, 128.21, 126.81, 126.08, 80.75, 77.65, 77.28, 64.86, 58.31, 57.97, 46.29, 45.62, 45.35, 44.66, 28.45. HR-MS calc for M+Na: 365.1590, obs: 365.1591. [α]$^{20}_D$+82.2 (c=1, CHCl$_3$).

Example 56

(5aS,8aS)-tert-butyl 3-(3-fluorophenyl)-5a,6,8,8a-tetrahydropyrrolo[3,4-b][1,2,3]triazolo[1,5-d][1,4]oxazine-7(4H)-carboxylate (Compound [56])

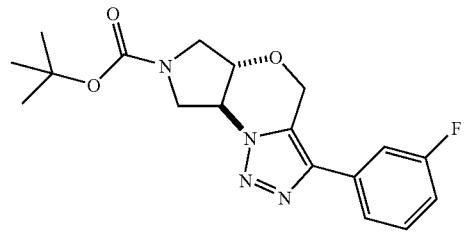

Example 56 can be prepared in the same manner as example 53 from (3S,4S)-tert-butyl 3-azido-4-(3-(3-fluorophenyl)prop-2-ynyloxy)pyrrolidine-1-carboxylate (143 mg, 0.39 mmol) and toluene (12 ml), afforded the titled compound (124 mg, 86%) as white solid. M.p. 249-250° C.

$^1$H NMR (400 MHz, CDCl$_3$): mixture of two rotamers, δ (ppm) 7.39 (m, 3H), 7.04 (m, 1H), 5.32 (AB system, 2H), 4.41 (m, 2H), 3.97 (m, 2H), 3.55 (m, 1H), 3.39 (m, 1H), 1.49 (s, 9H). $^{13}$C NMR (100 MHz, CDCl$_3$): δ (ppm) 163.21 (d, J$_{CF}$=245 Hz), 154.19, 140.94, 132.60, 130.59 (d, J$_{CF}$=8 Hz), 127.18, 121.59, 115.10 (d, J$_{CF}$=20 Hz), 113.00 (d, J$_{CF}$=23 Hz), 80.81, 77.70, 64.74, 58.36, 58.03, 46.21, 45.58, 45.30, 44.59, 28.35. HR-MS calc for M+H: 361.1676, obs: 361.1673. [α]$^{20}_D$+69.7 (c=1, CHCl$_3$).

Example 57

(5aS,8aS)-tert-butyl-3-(4-(trifluoromethyl)phenyl)-5a,6,8,8a-tetrahydropyrrolo[3,4-b][1,2,3]triazolo[1,5-c][1,4]oxazine-7(4H)-carboxylate (Compound [57])

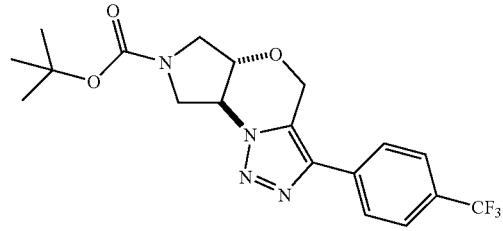

Example 57 can be prepared in the same manner as example 53 from (3S,4S)-tert-butyl 3-azido-4-(3-(4-(trifluoromethyl)phenyl)prop-2-ynyloxy)pyrrolidine-1-carboxylate (72 mg, 0.17 mmol) and toluene (12 ml), afforded the titled compound (57 mg, 79%) as white solid. M.p. 238-239° C.

$^1$H NMR (400 MHz, CDCl$_3$): mixture of two rotamers, δ (ppm) 7.71 (AB system, 4H), 5.34 (AB system, 2H), 4.42 (m, 2H), 3.98 (m, 2H), 3.56 (m, 1H), 3.39 (m, 1H), 1.49 (s, 9H). $^{13}$C NMR (100 MHz, CDCl$_3$): δ (ppm) 154.19, 140.69, 133.88, 127.75, 126.14, 126.25 (q, J$_{CF}$=270 Hz), 125.94 (q, J$_{CF}$=4 Hz), 80.81, 80.71, 77.70, 64.71, 58.36, 58.02, 46.17, 45.52, 45.23, 44.52, 28.31. HR-MS calc for M+H: 411.1644, obs: 411.1648. $[\alpha]^{20}_D$ +129.5 (c=1, CHCl$_3$).

General Procedure for the Synthesis of Compounds of General Formula (Ib') from Compounds of General Formula (1f')

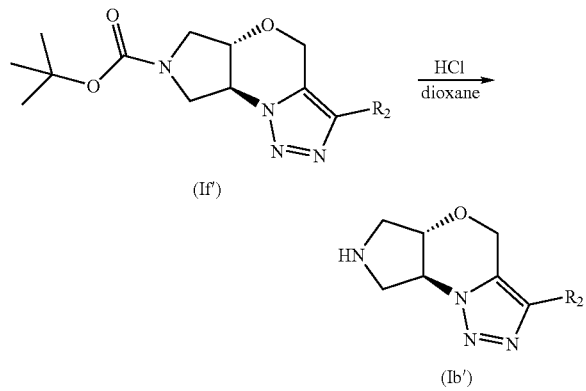

Example 58

(5aS,8S)-4,5a,6,7,8,8a-hexahydropyrrolo[3,4-b][1,2,3]triazolo[1,5-d][1,4]oxazine (Compound [58])

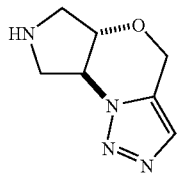

(5aS,8a5)-tert-butyl-5a,6,8,8a-tetrahydropyrrolo[3,4-b][1,2,3]triazolo[1,5-d][1,4]oxazine-7(4H)-carboxylate (100 mg, 0.37 mmol) was suspended in a solution of HCl in dioxane 4M (1 ml, 4.0 mmol) and stirred at r.t. for 5 hours. The reaction mixture was concentrated to dryness to give the titled compound (85 mg, 95%) as dihydrochloride.

$^1$H NMR (400 MHz, CD$_3$OD): δ (ppm) 7.94 (s, 1H), 5.38 (AB system, 2H), 4.77 (m, 1H), 4.45 (m, 1H), 4.37 (m, 2H), 3.91 (m, 1H), 3.78 (m, 1H), 3.52 (m, 1H).

Pharmacological Study

Brain membrane preparation and binding assays for the σ1-receptor were performed as described (DeHaven-Hudkins, D. L., L.C. Fleissner, and F. Y. Ford-Rice, 1992, Characterization of the binding of [$^3$H](+)pentazocine to σ recognition sites in guinea pig brain, Eur. J. Pharmacol. 227, 371-378) with some modifications. Guinea pig brains were homogenized in 10 vols. (w/v) of Tris-HCl 50 mM 0.32 M sucrose, pH 7.4, with a Kinematica Polytron PT 3000 at 15000 r.p.m. for 30 s. The homogenate was centrifuged at 1000 g for 10 min at 4° C. and the supernatants collected and centrifuged again at 48000 g for 15 min at 4° C. The pellet was resuspended in 10 volumes of Tris-HCl buffer (50 mM, pH 7.4), incubated at 37° C. for 30 min, and centrifuged at 48000 g for 20 min at 4° C. Following this, the pellet was resuspended in fresh Tris-HCl buffer (50 mM, pH 7.4) and stored on ice until use.

The radioligand used was [$^3$H]-(+)-pentazocine at 5.0 nM and the final volume was 200 μl. The incubation was initiated with the addition of 100 μA of membrane at a final tissue concentration of approximately 5 mg tissue net weight/mL and the incubation time was 150 m. at 37° C. After incubation, the membranes were collected onto pretreated glass fiber filterplate (MultiScreen-FC, Millipore), with polyethylenimine 0.1%. The filters were washed two times with 200 μA of washing buffer (50 mM Tris Cl, pH=7.4) and then 25 μA of Ecoscint H liquid scintillation cocktail were added. Microplates were allowed to set for several hours and then quantified by liquid scintillation spectrophotometry (1450 Microbeta, Wallac). Nonspecific binding was determined with 1 μM haloperidol.

| Compound | Name | Ki (nM) | % Displacement (10$^{-6}$ M) |
|---|---|---|---|
|  | trans-7-benzyl-4,5a,6,7,8,8a-hexahydropyrrolo[3,4-b][1,2,3]triazolo[1,5-d][1,4]oxazine |  | <50 |
|  | trans-7-benzyl-3-(4-chlorophenyl)-4,5a,6,7,8,8a-hexahydropyrrolo[3,4-b][1,2,3]triazolo[1,5-d][1,4]oxazine |  | 87 |

-continued

| Compound | Name | Ki (nM) | % Displacement (10⁻⁶ M) |
|---|---|---|---|
| | trans-7-(4-methoxybenzyl)-3-methyl-4,5a,6,7,8,8a-hexahydropyrrolo[3,4-b][1,2,3]triazolo[1,5-d][1,4]oxazine | >1000 | |
| | trans-3-ethyl-7-(4-methoxybenzyl)-4,5a,6,7,8,8a-hexahydropyrrolo[3,4-b][1,2,3]triazolo[1,5-d][1,4]oxazine | 298 ± 76.2 | |
| | trans-7-benzyl-3-methyl-4,5a,6,7,8,8a-hexahydropyrrolo[3,4-b][1,2,3]triazolo[1,5-d][1,4]oxazine | >1000 | |
| | trans-7-benzyl-3-(4-(trifluoromethyl)phenyl)-4,5a,6,7,8,8a-hexahydropyrrolo[3,4-b][1,2,3]triazolo[1,5-d][1,4]oxazine | 31.3 ± 8.7 | |
| | trans-7-benzyl-3-(2-fluorophenyl)-4,5a,6,7,8,8a-hexahydropyrrolo[3,4-b][1,2,3]triazolo[1,5-d][1,4]oxazine | 27.4 ± 4.9 | |
| | trans-7-benzyl-3-ethyl-4,5a,6,7,8,8a-hexahydropyrrolo[3,4-b][1,2,3]triazolo[1,5-d][1,4]oxazine | 375 ± 1.6 | |
| | trans-7-benzyl-3-(3-fluorophenyl)-4,5a,6,7,8,8a-hexahydropyrrolo[3,4-b][1,2,3]triazolo[1,5-d][1,4]oxazine | 15.8 ± 0.3 | |

-continued

| Compound | Name | Ki (nM) | % Displacement (10⁻⁶ M) |
|---|---|---|---|
| 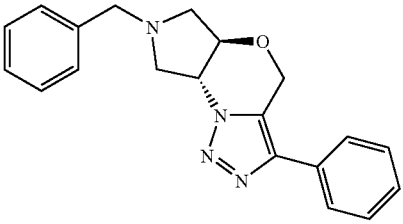 [SMILES: c1ccc(CN2C[C@@H]3[C@@H](C2)OCc2c(-c4ccccc4)nnn23)cc1] | trans-7-benzyl-3-phenyl-4,5a,6,7,8,8a-hexahydropyrrolo[3,4-b][1,2,3]triazolo[1,5-d][1,4]oxazine | 26.9 ± 4.4 | |
| 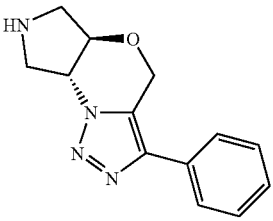 [SMILES: c1ccc(-c2nnn3c2CO[C@@H]2CNC[C@H]23)cc1] | trans-3-phenyl-4,5a,6,7,8,8a-hexahydropyrrolo[3,4-b][1,2,3]triazolo[1,5-d][1,4]oxazine | 283.48 261.81 | |
| 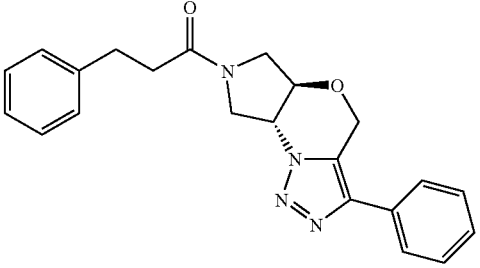 [SMILES: O=C(CCc1ccccc1)N1C[C@@H]2[C@@H](C1)OCc1c(-c3ccccc3)nnn12] | trans-3-phenyl-1-(3-phenyl-5a,6,8,8a-tetrahydropyrrolo[3,4-b][1,2,3]triazolo[1,5-d][1,4]oxazin-7(4H)-yl)propan-1-one | 563.34 | |
| 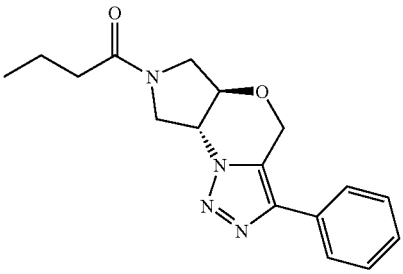 [SMILES: CCCC(=O)N1C[C@@H]2[C@@H](C1)OCc1c(-c3ccccc3)nnn12] | trans-1-(3-phenyl-5a,6,8,8a-tetrahydropyrrolo[3,4-b][1,2,3]triazolo[1,5-d][1,4]oxazin-7(4H)-yl)butan-1-one | 334.09 341.23 | |
| 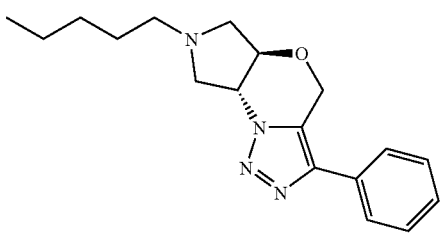 [SMILES: CCCCCN1C[C@@H]2[C@@H](C1)OCc1c(-c3ccccc3)nnn12] | trans-7-pentyl-3-phenyl-4,5a,6,7,8,8a-hexahydropyrrolo[3,4-b][1,2,3]triazolo[1,5-d][1,4]oxazine | 5.47 6.79 | |

The invention claimed is:
1. A compound of formula (I)

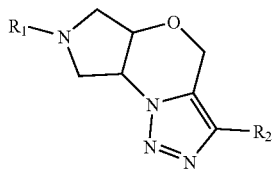

wherein
R$_1$ represents an hydrogen atom; —COR$_3$, —C(O)OR$_3$, —C(O)NR$_3$R$_4$, —C=NR$_3$, —CN, —OR$_3$, —OC(O)R$_3$, —S(O)$_n$—R$_3$, —NR$_3$R$_4$, —NR$_3$C(O)R$_4$, —NO$_2$, —N=CR$_3$R$_4$, or an halogen atom;
a branched or unbranched, saturated or unsaturated, optionally at least mono-substituted, aliphatic radical C$_{1-10}$;
a substituted or unsubstituted cycloalkyl radical C$_{3-9}$; a branched or unbranched cycloalkyl-alkyl radical C$_{1-10}$ group in which either the alkyl group and/or the cycloalkyl group is optionally at least mono-substituted; a substituted or unsubstituted cycloalkyl C$_{3-9}$ or cycloalkylalkyl C$_{1-10}$ group in which the cycloalkyl group is condensed with another substituted or unsubstituted mono- or polycyclic ring system;
a substituted or unsubstituted aryl radical; a substituted or unsubstituted, branched or unbranched arylalkyl radical C$_{1-10}$, at least mono-substituted benzhydryl group;
a substituted or unsubstituted heteroaryl radical; a substituted or unsubstituted, branched or unbranched heteroarylalkyl radical C$_{1-10}$; a substituted or unsubstituted non-aromatic heterocyclyl radical C$_{3-9}$; a substituted or unsubstituted, branched or unbranched heterocyclylalkyl radical C$_{3-9}$;
a substituted or unsubstituted heterocyclyl C$_{3-9}$ or heterocycloalkyl radical C$_{1-10}$ group in which the heterocyclyl group is condensed with another substituted or unsubstituted mono- or polycyclic ring system;
R$_2$ represents an hydrogen atom; —COR$_3$, —C(O)OR$_3$, —C(O)NR$_3$R$_4$, —C=NR$_3$, —CN, —OR$_3$, —OC(O)R$_3$, —S(O)$_n$—R$_3$, —NR$_3$R$_4$, —NR$_3$C(O)R$_4$, —NO$_2$, —N=CR$_3$R$_4$, or an halogen atom;
a branched or unbranched, saturated or unsaturated, optionally at least mono-substituted, aliphatic radical C$_{1-10}$;
a substituted or unsubstituted cycloalkyl radical C$_{3-9}$; a branched or unbranched cycloalkyl-alkyl radical C$_{1-10}$ group in which either the alkyl group and/or the cycloalkyl group is optionally at least mono-substituted; a substituted or unsubstituted cycloalkyl C$_{3-9}$ or cycloalkylalkyl C$_{1-10}$ radical group in which the cycloalkyl group is condensed with another substituted or unsubstituted mono- or polycyclic ring system;
a substituted or unsubstituted aryl radical; a substituted or unsubstituted, branched or unbranched arylalkyl radical C$_{1-10}$, at least mono-substituted benzhydryl group;
a substituted or unsubstituted heteroaryl radical; a substituted or unsubstituted, branched or unbranched heteroarylalkyl radical C$_{1-10}$; a substituted or unsubstituted non-aromatic heterocyclyl radical C$_{3-9}$; a substituted or unsubstituted, branched or unbranched heterocyclylalkyl radical C$_{3-9}$;
a substituted or unsubstituted heterocyclyl C$_{3-9}$ or heterocycloalkyl C$_{1-10}$ radical group in which the heterocyclyl group is condensed with another substituted or unsubstituted mono- or polycyclic ring system;
R$_3$ and R$_4$ are each independently selected from hydrogen or halogen;
a branched or unbranched, saturated or unsaturated, optionally at least mono-substituted, aliphatic radical C$_{1-10}$;
a substituted or unsubstituted cycloalkyl radical C$_{3-9}$; branched or unbranched cycloalkyl-alkyl radical C$_{1-10}$ group in which either the alkyl group and/or the cycloalkyl group is optionally at least mono-substituted;
a substituted or unsubstituted aryl radical; a substituted or unsubstituted arylalkyl radical C$_{1-10}$ an optionally, at least mono-substituted benzhydryl group;
a substituted or unsubstituted heteroaryl radical; a substituted or unsubstituted, branched or unbranched heteroarylalkyl radical C$_{1-10}$; a substituted or unsubstituted non-aromatic heterocyclyl radical C$_{3-9}$; a substituted or unsubstituted, branched or unbranched heterocyclylalkyl radical C$_{3-9}$;
a substituted or unsubstituted heterocyclyl C$_{3-9}$ or heterocycloalkyl C$_{1-10}$ radical group in which the heterocyclyl group is condensed with another substituted or unsubstituted mono- or polycyclic ring system;
wherein the substituents for the alkyl, cycloalkyl, aryl and heteroaryl radicals are independently selected from the group consisting of C$_{1-4}$ alkyl, linear or branched C$_{1-6}$alkoxy, F, Cl, I, Br, CF$_3$, CH$_2$F, CHF$_2$, CN, OH, SH, NH$_2$, oxo, (C=O)R', SR', SOR', SO$_2$R', NHR', NR'R" whereby R' and optionally R" for each substituent independently represents a linear or branched C$_{1-6}$-alkyl group; and
wherein the substituents for the arylalkyl radical is selected from the group consisting of F, Cl, Br, I, NH$_2$, SH, OH, SO$_2$, CF$_3$, carboxy, amido, cyano, carbamyl, nitro, phenyl, benzyl, —SO$_2$NH$_2$, C$_{1-6}$ alkyl and C$_{1-6}$-alkoxy; and
n is 0, 1 or 2;
or a pharmaceutically acceptable salt or isomer thereof.

2. A compound according to claim 1 where R$_1$ is an hydrogen atom; —COR$_3$, —C(O)OR$_3$, —C(O)NR$_3$R$_4$, —C=NR$_3$, —CN, —OR$_3$, —OC(O)R$_3$, —S(O)$_n$—R$_3$, —NR$_3$R$_4$, —NR$_3$C(O)R$_4$, —N=CR$_3$R$_4$, an halogen atom;
a branched or unbranched, saturated or unsaturated, optionally at least mono-substituted, aliphatic radical C$_{1-10}$; a substituted or unsubstituted cycloalkyl radical C$_{3-9}$; a substituted or unsubstituted aryl radical; a substituted or unsubstituted, branched or unbranched arylalkyl radical C$_{1-10}$, at least mono-substituted benzhydryl group;
a substituted or unsubstituted heteroaryl radical; a substituted or unsubstituted, branched or unbranched heteroarylalkyl radical C$_{1-10}$; a substituted or unsubstituted non-aromatic heterocyclyl radical C$_{3-9}$; a substituted or unsubstituted, branched or unbranched heterocyclylalkyl radical C$_{3-9}$; or a pharmaceutically acceptable salt or isomer thereof.

3. A compound according to claim 1 where R$_2$ is an hydrogen atom or —COR$_3$, —C(O)OR$_3$, —C(O)NR$_3$R$_4$, —C=NR$_3$, —CN, —OR$_3$, —OC(O)R$_3$, —S(O)$_n$—R$_3$, —NR$_3$R$_4$, —NR$_3$C(O)R$_4$, —NO$_2$, —N=CR$_3$R$_4$, an halogen atom; a substituted or unsubstituted cycloalkyl radical C$_{3-9}$; a substituted or unsubstituted aryl radical; a substituted or unsubstituted arylalkyl radical C$_{1-10}$; a substituted or unsubstituted heteroaryl radical; an unbranched or branched, saturated or unsaturated, optionally at least mono-substituted aliphatic radical $C_{1-10}$; an unsubstituted heteroarylalkyl radical $C_{1-10}$ or a pharmaceutically acceptable salt or isomer thereof.

4. A compound according to claim 1 where $R_3$ and $R_4$ are each independently selected from hydrogen or halogen; a substituted or unsubstituted cycloalkyl radical $C_{3-9}$; a substituted or unsubstituted aryl radical; a substituted or unsubstituted arylalkyl radical $C_{1-10}$; a substituted or unsubstituted heteroaryl radical; an unbranched or branched, saturated or unsaturated, optionally at least mono-substituted aliphatic radical $C_{1-10}$; an unsubstituted heteroarylalkyl radical $C_{1-10}$ or a pharmaceutically acceptable salt or isomer thereof.

5. A compound according to claim 1 where $R_1$ is an hydrogen atom; an halogen atom; —$COR_3$; —$C(O)OR_3$; —$C(O)NR_3R_4$; —$S(O)_n$—$R_3$; a substituted or unsubstituted cycloalkyl radical $C_{3-9}$; a substituted or unsubstituted aryl radical; a substituted or unsubstituted arylalkyl radical $C_{1-10}$; a substituted or unsubstituted heteroaryl radical; an unbranched or branched, saturated or unsaturated, optionally at least mono-substituted aliphatic radical $C_{1-10}$;
  $R_2$ hydrogen atom or halogen; a substituted or unsubstituted cycloalkyl radical $C_{3-9}$; a substituted or unsubstituted aryl radical; a substituted or unsubstituted heteroaryl radical; an unbranched or branched, saturated or unsaturated, optionally at least mono-substituted, aliphatic radical $C_{1-10}$; and
  $R_3$ and $R_4$ are each independently selected from hydrogen or halogen; a substituted or unsubstituted aryl radical; a substituted or unsubstituted heteroaryl radical; an unbranched or branched, saturated or unsaturated, optionally at least mono-substituted, aliphatic radical $C_{1-10}$ or a substituted; an unsubstituted alkylaryl $C_{1-10}$ or heteroarylalkyl radical $C_{1-10}$ or a pharmaceutically acceptable salt or isomer thereof.

6. A compound according to claim 1 where $R_1$ is an hydrogen atom; a halogen; —$COR_3$; —$C(O)OR_3$; —$C(O)NR_3R_4$; —$S(O)_n$—$R_3$; a substituted or unsubstituted cycloalkyl radical $C_{3-9}$; a substituted or unsubstituted aryl radical; a substituted or unsubstituted arylalkyl radical $C_{1-10}$; a substituted or unsubstituted heteroaryl radical; an unbranched or branched, saturated or unsaturated, optionally at least mono-substituted aliphatic radical $C_{1-10}$;
  $R_2$ is an hydrogen atom or an halogen atom; a substituted or unsubstituted aryl radical; an unbranched or branched, saturated or unsaturated, optionally at least mono-substituted, aliphatic radical $C_{1-10}$; and
  $R_3$ and $R_4$ are each independently selected from hydrogen or halogen; an unbranched or branched, saturated or unsaturated, optionally at least mono-substituted aliphatic radical $C_{1-10}$; an unsubstituted alkylaryl or heteroarylalkyl radical $C_{1-10}$ or a pharmaceutically acceptable salt or isomer thereof.

7. A pharmaceutical composition comprising a compound according to claim 1 and a pharmaceutically acceptable carrier.

8. A method for the treatment of a sigma receptor mediated disease or condition is pain or for the treatment of a sigma receptor mediated disease or condition wherein said disease or condition is selected from diarrhea, lipoprotein disorders, hyperlipidemia, hypertriglyceridemia, hypercholesterolemia, obesity, migraine, hypertension, arrhythmia, ulcer, glaucoma, demyelinating diseases, addiction to drugs and chemical substances, tardive diskinesia, ischemic stroke, epilepsy, stroke, and stress, comprising administering to a patient in need of such treatment a therapeutically effective amount of a compound according to claim 1.

9. A method according to claim 8 wherein the disease or condition is selected from diarrhea, lipoprotein disorders, hyperlipidemia, hypertriglyceridemia, hypercholesterolemia, obesity, migraine, arthritis, hypertension, arrhythmia, ulcer, glaucoma, learning, memory and attention deficits, cognition disorders, neurodegenerative diseases, demyelinating diseases, addiction to drugs and chemical substances, tardive dyskinesia, ischemic stroke, epilepsy, stroke, stress.

10. A method according to claim 8 wherein the disease or condition is pain.

11. A process for the preparation of a compound of formula (Ia):

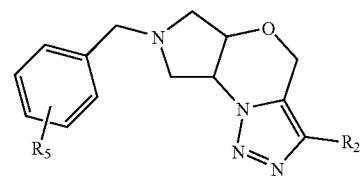

comprising the heating of a compound of formula (II):

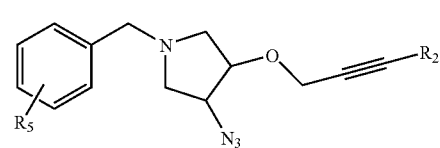

in toluene or xylene to a temperature of 100-130° C.,
where $R_2$ has the meaning as in claim 1 and $R_5$ is a hydrogen, a halogen or an $C_1$-$C_{10}$ alkyloxy.

12. A process for the preparation of a compound of formula (Ib):

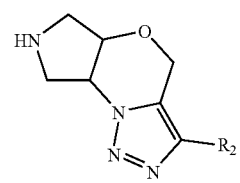

comprising the hydrogenolysis of compound (Ia):

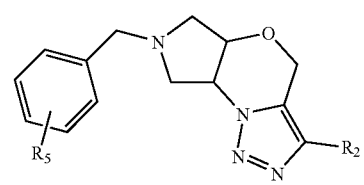

wherein $R_2$ has the same meanings as in claim 1, and $R_5$ is a hydrogen, a halogen or a $C_1$-$C_{10}$ alkoxy in the presence of hydrogen and a catalyst in an organic solvent.

13. A process for the preparation of compound of formula (Ie):

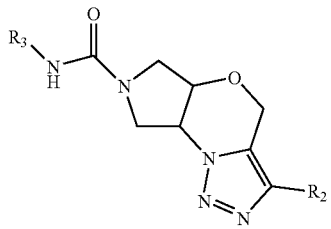
(Ie)

comprising the reaction between a compound of formula (Ib):

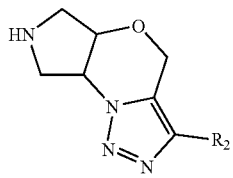
(Ib)

with an isocyanate of formula (III):

   (III)

in an organic solvent and optionally in the presence of a supported amine, and
wherein $R_2$ and $R_3$ have the meanings as in claim 1.

14. A process for the preparation of a compound of formula (I):

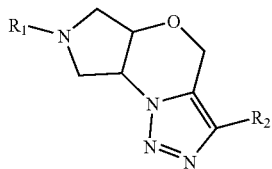
(I)

comprising the reaction between a compound of formula (Ib):

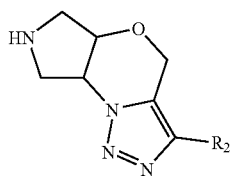
(Ib)

with a compound of formula (IV):

   (IV)

in an organic solvent and optionally in the presence of a base and/or a catalyst,
wherein $R_1$ and $R_2$ have the meanings as in claim 1 and X is a halogen.

15. A process according to claim 14 where compound (IV) may be represented by formula (IV'):

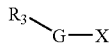   (IV')

where $R_3$ is selected from hydrogen
a branched or unbranched, saturated or unsaturated, optionally at least mono-substituted, aliphatic radical $C_{1-10}$;
a substituted or unsubstituted cycloalkyl radical $C_{3-9}$; branched or unbranched cycloalkyl-alkyl radical $C_{1-10}$ group in which either the alkyl group and/or the cycloalkyl group is optionally at least mono-substituted;
a substituted or unsubstituted aryl radical; a substituted or unsubstituted arylalkyl radical $C_{1-10}$ an optionally, at least mono-substituted benzhydryl group;
a substituted or unsubstituted heteroaryl radical; a substituted or unsubstituted, branched or unbranched heteroarylalkyl radical $C_{1-10}$; substituted or unsubstituted non-aromatic heterocyclyl radical $C_{3-9}$; a substituted or unsubstituted, branched or unbranched heterocyclylalkyl radical $C_{3-9}$;
a substituted or unsubstituted heterocyclyl $C_{3-9}$ or heterocycloalkyl $C_{1-10}$ radical group in which the heterocyclyl group is condensed with another substituted or unsubstituted mono- or polycyclic ring system,
X is as defined in claim 14 and G represents —$SO_2$—, —CO—, or —COO—.

16. A process for the preparation of enantiomerically pure compound (I) comprising:
a) the reaction of compound of formula (XII) or its enantiomer:

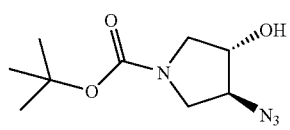
(XII)

with a compound of formula (Z) in an organic solvent:

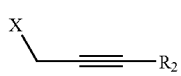
(Z)

b) heating the resulting compound of formula (XIII), or its enantiomer, in xylene or toluene:

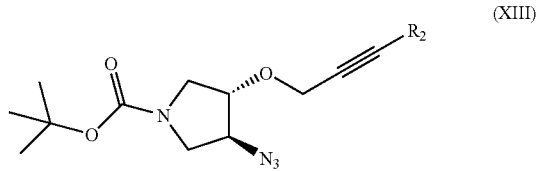
(XIII)

c) hydrolyzing the resulting compound of formula (If'), or its enantiomer, in an acidic medium:

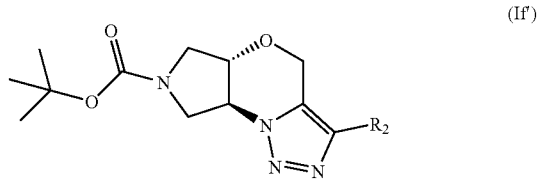
(If')

d) reacting the resulting compound with compound (IV) as defined in claim 14 in an organic solvent and optionally in the presence of a base and a catalyst, or with compound (III) in an organic solvent and optionally in the presence of a supported amine, and wherein $R_1$, $R_2$ and $R_3$ have the meanings as in claim 1 and X is a halogen.

17. A pharmaceutical composition which comprises a compound as defined in claim 1 or a pharmaceutically acceptable salt or isomer thereof, and at least a pharmaceutically acceptable carrier, additive, adjuvant or vehicle.

18. A method according to claim 9 wherein the drugs and chemical substances are selected from cocaine, amphetamine, ethanol and nicotine.

19. A method according to claim 8 wherein the disease is neuropathic pain or inflammatory pain.

20. A method according to claim 8 wherein the disease is a pain condition involving allodynia or hyperalgesia or both.

21. A compound selected from the group consisting of:
- [1] (5a,8a-trans)-7-(4-methoxybenzyl)-4,5a,6,7,8,8a-hexahydropyrrolo[3,4-b][1,2,3]triazolo[1,5-d][1,4]oxazine,
- [2] (5a,8a-trans)-7-(4-methoxybenzyl)-3-methyl-4,5a,6,7,8,8a-hexahydropyrrolo[3,4-b][1,2,3]triazolo[1,5-d][1,4]oxazine,
- [3] (5a,8a-trans)-3-ethyl-7-(4-methoxybenzyl)-4,5a,6,7,8,8a-hexahydropyrrolo[3,4-b][1,2,3]triazolo[1,5-d][1,4]oxazine,
- [4] (5a,8a-trans)-7-benzyl-4,5a,6,7,8,8a-hexahydropyrrolo[3,4-b][1,2,3]triazolo[1,5-d][1,4]oxazine,
- [5] (5a,8a-trans)-7-benzyl-3-methyl-4,5a,6,7,8,8a-hexahydropyrrolo[3,4-b][1,2,3]triazolo[1,5-d][1,4]oxazine,
- [6] (5a,8a-trans)-7-benzyl-3-(4-(trifluoromethyl)phenyl)-4,5a,6,7,8,8a-hexa hydropyrrolo[3,4-b][1,2,3]triazolo[1,5-d][1,4]oxazine,
- [7] (5a,8a-trans)-7-benzyl-3-(2-fluorophenyl)-4,5a,6,7,8,8a-hexahydropyrrolo[3,4-b][1,2,3]triazolo[1,5-d][1,4]oxazine,
- [8] (5a,8a-trans)-7-benzyl-3-ethyl-4,5a,6,7,8,8a-hexahydropyrrolo[3,4-b][1,2,3]triazolo[1,5-d][1,4]oxazine,
- [9] (5a,8a-trans)-7-benzyl-3-(4-chlorophenyl)-4,5a,6,7,8,8a-hexahydropyrrolo [3,4-b][1,2,3]triazolo[1,5-d][1,4]oxazine,
- [10] (5a,8a-trans)-7-benzyl-3-(3-fluorophenyl)-4,5a,6,7,8,8a-hexahydropyrrol[3,4-b][1,2,3]triazolo[1,5-d][1,4]oxazine,
- [11] (5a,8a-trans)-7-benzyl-3-phenyl-4,5a,6,7,8,8a-hexahydropyrrolo[3,4-b][1,2,3]triazolo[1,5-d][1,4]oxazine,
- [12] (5a,8a-trans)-4,5a,6,7,8,8a-hexahydropyrrolo[3,4-b][1,2,3]triazolo[1,5-d][1,4]oxazine,
- [13] (5a,8a-trans)-3-phenyl-4,5a,6,7,8,8a-hexahydropyrrolo[3,4-b][1,2,3]triazolo[1,5-d][1,4]oxazine,
- [14] (5a,8a-trans)-7-(methylsulfonyl)-4,5a,6,7,8,8a-hexahydropyrrolo[3,4-b][1,2,3]triazolo[1,5-d][1,4]oxazine,
- [15] (5a,8a-trans)-7-(4-bromophenylsulfonyl)-4,5a,6,7,8,8a-hexahydropyrrolo[3,4-b][1,2,3]triazolo[1,5-d][1,4]oxazine,
- [16] (5a,8a-trans)-7-(phenylsulfonyl)-4,5a,6,7,8,8a-hexahydropyrrolo[3,4-b][1,2,3]triazolo[1,5-d][1,4]oxazine,
- [17] (5a,8a-trans)-7-(2-fluorophenylsulfonyl)-4,5a,6,7,8,8a-hexahydropyrrolo [3,4-b][1,2,3]triazolo[1,5-d][1,4]oxazine,
- [18] (5a,8a-trans)-7-(4-fluorophenylsulfonyl)-4,5a,6,7,8,8a-hexahydropyrrolo [3,4-b][1,2,3]triazolo[1,5-d][1,4]oxazine,
- [19] (5a,8a)-7-(methylsulfonyl)-3-phenyl-4,5a,6,7,8,8a-hexahydropyrrolo[3,4-b][1,2,3]triazolo[1,5-d][1,4]oxazine,
- [20] (5a,8a-trans)-7-(4-fluorophenylsulfonyl)-3-phenyl-4,5a,6,7,8,8a-hexa hydropyrrolo[3,4-b][1,2,3]triazolo[1,5-d][1,4]oxazine,
- [21] (2-fluorophenyl)((5a,8a-trans)-5a,6,8,8a-tetrahydropyrrolo[3,4-b][1,2,3]triazolo[1,5-d][1,4]oxazin-7(4H)-yl)methanone,
- [22] phenyl((5a,8a-trans)-5a,6,8,8a-tetrahydropyrrolo[3,4-b][1,2,3]triazolo[1,5-d][1,4]oxazin-7(4H)-yl)methanone,
- [23] (2,4-dichlorophenyl)((5a,8a-trans)-5a,6,8,8a-tetrahydropyrrolo[3,4-b][1,2,3]triazolo[1,5-d][1,4]oxazin-7(4H)-yl)methanone,
- [24] 3-phenyl-1-((5a,8a-trans)-5a,6,8,8a-tetrahydropyrrolo[3,4-b][1,2,3]triazolo[1,5-d][1,4]oxazin-7(4H)-yl)propan-1-one,
- [25] 1-((5a,8a-trans)-5a,6,8,8a-tetrahydropyrrolo[3,4-b][1,2,3]triazolo[1,5-d][1,4]oxazin-7(4H)-yl)butan-1-one,
- [26] ((5a,8a-trans)-5a,6,8,8a-tetrahydropyrrolo[3,4-b][1,2,3]triazolo[1,5-d][1,4]oxazin-7(4H)-yl)(thiophen-2-yl)methanone,
- [27] phenyl((5a,8a-trans)-3-phenyl-5a,6,8,8a-tetrahydropyrrolo[3,4-b][1,2,3]triazolo[1,5-d][1,4]oxazin-7(4H)-yl)methanone,
- [28] 3-phenyl-1-((5a,8a-trans)-3-phenyl-5a,6,8,8a-tetrahydropyrrolo[3,4-b][1,2,3]triazolo[1,5-d][1,4]oxazin-7(4H)-yl)propan-1-one,
- [29] 1-((5a,8a-trans)-3-phenyl-5a,6,8,8a-tetrahydropyrrolo[3,4-b][1,2,3]triazolo[1,5-d][1,4]oxazin-7(4H)-yl)butan-1-one,
- [30] ((5a,8a-trans)-3-phenyl-5a,6,8,8a-tetrahydropyrrolo[3,4-b][1,2,3]triazolo [1,5-d][1,4]oxazin-7(4H)-yl)(thiophen-2-yl)methanone,
- [31] (5a,8a-trans)-N-butyl-5a,6,8,8a-tetrahydropyrrolo[3,4-b][1,2,3]triazolo[1,5-d][1,4]oxazine-7(4H)-carboxamide,
- [32] (5a,8a-trans)-N-phenyl-5a,6,8,8a-tetrahydropyrrolo[3,4-b][1,2,3]triazolo [1,5-d][1,4]oxazine-7(4H)-carboxamide,
- [33] (5a,8a-trans)-N,3-diphenyl-5a,6,8,8a-tetrahydropyrrolo[3,4-b][1,2,3] triazolo[1,5-d][1,4]oxazine-7(4H)-carboxamide,
- [34] (5a,8a-trans)-benzyl 3-phenyl-5a,6,8,8a-tetrahydropyrrolo[3,4-b][1,2,3]triazolo[1,5-d][1,4]oxazine-7(4H)-carboxylate,
- [35] (5a,8a-trans)-7-(pyrimidin-2-yl)-4,5a,6,7,8,8a-hexahydropyrrolo[3,4-b][1,2,3]triazolo[1,5-d][1,4]oxazine,
- [36] (5a,8a-trans)-7-ethyl-4,5a,6,7,8,8a-hexahydropyrrolo[3,4-b][1,2,3]triazolo[1,5-d][1,4]oxazine,
- [37] (5a,8a-trans)-7-pentyl-4,5a,6,7,8,8a-hexahydropyrrolo[3,4-b][1,2,3]triazolo[1,5-d][1,4]oxazine,
- [38] (5a,8a-trans)-7-(4-fluorobenzyl)-4,5a,6,7,8,8a-hexahydropyrrolo[3,4-b][1,2,3]triazolo[1,5-d][1,4]oxazine,
- [39] (5a,8a-trans)-7-(pyridin-2-ylmethyl)-4,5a,6,7,8,8a-hexahydropyrrolo[3,4-b][1,2,3]triazolo[1,5-d][1,4]oxazine,
- [40] (5a,8a-trans)-3-phenyl-7-(pyrimidin-2-yl)-4,5a,6,7,8,8a-hexahydropyrrolo[3,4-b][1,2,3]triazolo[1,5-d][1,4]oxazine,
- [41] (5a,8a-trans)-7-pentyl-3-phenyl-4,5a,6,7,8,8a-hexahydropyrrolo[3,4-b][1,2,3]triazolo[1,5-d][1,4]oxazine,
- [42] (5a,8a-trans)-7-phenyl-4,5a,6,7,8,8a-hexahydropyrrolo[3,4-b][1,2,3]triazolo[1,5-d][1,4]oxazine,
- [43] (5a,8a-trans)-7-(4-chlorophenyl)-4,5a,6,7,8,8a-hexahydropyrrolo[3,4-b][1,2,3]triazolo[1,5-d][1,4]oxazine,
- [44] (5a,8a-trans)-7-(pyridin-2-yl)-4,5a,6,7,8,8a-hexahydropyrrolo[3,4-b][1,2,3]triazolo[1,5-d][1,4]oxazine,
- [45] (5a,8a-trans)-3,7-diphenyl-4,5a,6,7,8,8a-hexahydropyrrolo[3,4-b][1,2,3]triazolo[1,5-d][1,4]oxazine,

[46] (5a,8a-trans)-7-(4,6-dichloropyrimidin-2-yl)-4,5a,6,7,8,8a-hexahydropyrrolo[3,4-b][1,2,3]triazolo[1,5-d][1,4]oxazine,

[47] (5a,8a-trans)-7-(4,6-dichloropyrimidin-2-yl)-3-phenyl-4,5a,6,7,8,8a-hexahydropyrrolo[3,4-b][1,2,3]triazolo[1,5-d][1,4]oxazine,

[48] (5a,8a-trans)-7-(4-chloropyrimidin-2-yl)-3-phenyl-4,5a,6,7,8,8a-hexahydropyrrolo[3,4-b][1,2,3]triazolo[1,5-d][1,4]oxazine,

[49] (5a,8a-trans)-7-(4-chloropyrimidin-2-yl)-4,5a,6,7,8,8a-hexahydropyrrolo[3,4-b][1,2,3]triazolo[1,5-d][1,4]oxazine,

[50] 2-((5a,8a-trans)-5a,6,7,8,8a-tetrahydropyrrolo[3,4-b][1,2,3]triazolo[1,5-d][1,4]oxazin-7(4H)-yl)pyrimidin-4-amine,

[51] 2-((5a,8a-trans)-3-phenyl-5a,6,7,8,8a-tetrahydropyrrolo[3,4-b][1,2,3]triazolo[1,5-d][1,4]oxazin-7(4H)-yl)pyrimidin-4-amine,

[52] 6-((5a,8a-trans)-3-phenyl-5a,6,8,8a-tetrahydropyrrolo[3,4-b][1,2,3]triazolo[1,5-d][1,4]oxazin-7(4H)-yl)-1,3,5-triazine-2,4-diamine,

[53] (5aS,8aS)-tert-butyl 5a,6,8,8a-tetrahydropyrrolo[3,4-b][1,2,3]triazolo[1,5-d][1,4]oxazine-7(4H)-carboxylate,

[54] (5aS,8aS)-tert-butyl 3-methyl-5a,6,8,8a-tetrahydropyrrolo[3,4-b][1,2,3]triazolo[1,5-d][1,4]oxazine-7(4H)-carboxylate,

[55] (5aS,8aS)-tert-butyl 3-phenyl-5a,6,8,8a-tetrahydropyrrolo[3,4-b][1,2,3]triazolo[1,5-d][1,4]oxazine-7(4H)-carboxylate,

[56] (5aS,8aS)-tert-butyl 3-(3-fluorophenyl)-5a,6,8,8a-tetrahydropyrrolo[3,4-b][1,2,3]triazolo[1,5-d][1,4]oxazine-7(4H)-carboxylate,

[57] (5aS,8aS)-tert-butyl 3-(4-(trifluoromethyl)phenyl)-5a,6,8,8a-tetrahydropyrrolo[3,4-b][1,2,3]triazolo[1,5-d][1,4]oxazine-7(4H)-carboxylate, and

[58] (5aS,8S)-4,5a,6,7,8,8a-hexahydropyrrolo[3,4-b][1,2,3]triazolo[1,5-d][1,4]oxazine.

\* \* \* \* \*

UNITED STATES PATENT AND TRADEMARK OFFICE
CERTIFICATE OF CORRECTION

PATENT NO. : 8,362,011 B2
APPLICATION NO. : 12/746635
DATED : January 29, 2013
INVENTOR(S) : Miguel Angel Pericas-Brondo et al.

Page 1 of 1

It is certified that error appears in the above-identified patent and that said Letters Patent is hereby corrected as shown below:

On the title page,
Item (73): The name of the assignee should read: Laboratorios del Dr. Esteve, S.A.

Signed and Sealed this
Twelfth Day of March, 2013

Teresa Stanek Rea
*Acting Director of the United States Patent and Trademark Office*

UNITED STATES PATENT AND TRADEMARK OFFICE
CERTIFICATE OF CORRECTION

PATENT NO. : 8,362,011 B2 Page 1 of 1
APPLICATION NO. : 12/746635
DATED : January 29, 2013
INVENTOR(S) : Pericas-Brondo et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 264 days.

Signed and Sealed this
First Day of September, 2015

Michelle K. Lee
*Director of the United States Patent and Trademark Office*